United States Patent [19]

Martel et al.

[11] Patent Number: 4,833,163
[45] Date of Patent: May 23, 1989

[54] NOVEL CYCLOPROPANE CARBOXYLIC ACID DERIVATIVES

[75] Inventors: Jacques Martel, Bondy; Jean Tessier, Vincennes; André Teche, Paris, all of France

[73] Assignee: Roussel Uclaf, Paris, France

[21] Appl. No.: 120,869

[22] Filed: Nov. 16, 1987

Related U.S. Application Data

[60] Continuation of Ser. No. 922,733, Oct. 23, 1986, abandoned, which is a continuation of Ser. No. 745,654, Jun. 17, 1985, abandoned, which is a division of Ser. No. 520,118, Aug. 3, 1983, abandoned, which is a continuation-in-part of Ser. No. 266,164, May 22, 1981, abandoned.

[30] Foreign Application Priority Data

Jan. 17, 1983 [FR] France .................... 83 00614

[51] Int. Cl.$^4$ .................... C07C 69/743; A01N 53/00
[52] U.S. Cl. .................... 514/531; 560/124
[58] Field of Search .................... 560/124; 514/531

[56] References Cited

U.S. PATENT DOCUMENTS

| | | | |
|---|---|---|---|
| 4,024,163 | 5/1977 | Elliott | 560/124 |
| 4,183,950 | 1/1980 | Naumann | 560/124 |
| 4,318,922 | 3/1982 | Fuchs | 560/124 |
| 4,423,066 | 12/1983 | Fuchs | 560/124 |

FOREIGN PATENT DOCUMENTS 1078511 8/1967 United Kingdom .................... 560/124

OTHER PUBLICATIONS

Elliott, ACS Symposium Series, 42, pp. 1–28 (1977).
Elliott, Chem. Soc. Rev., 1, pp. 473–504 (1978).
Elliott, Pest. Sci., 7, pp. 499–502 (1976).

*Primary Examiner*—Michael L. Shippen
*Attorney, Agent, or Firm*—Bierman and Muserlian

[57] ABSTRACT

Novel isomers and mixtures thereof of cyclopropane carboxylic acid derivatives with a 3-unsaturated side chain of Z geometry of the formula

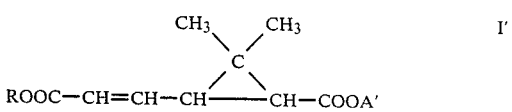

wherein A' is

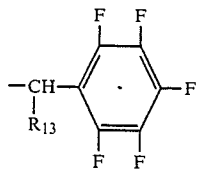

wherein $R_{13}$ is selected from the group consisting of hydrogen and CN and R is an optionally unsaturated alkyl of 1 to 18 carbon atoms having insecticidal and nematocidal activity as well as plant and animal acaricidal activity and their preparation.

11 Claims, No Drawings

NOVEL CYCLOPROPANE CARBOXYLIC ACID DERIVATIVES

PRIOR APPLICATION

This application is a continuation of U.S. patent application Ser. No. 922,733 filed Oct. 23, 1986, now abandoned which is a continuation of U.S. patent application Ser. No. 745,654 filed June 17, 1985, now abandoned, which is a division of copending commonly assigned U.S. patent application Ser. No. 520,118 filed Aug. 3, 1983, now abandoned which in turn is a continuation-in-part of our copending, commonly assigned U.S. patent application Ser. No. 266,164 filed May 22, 1981, now abandoned.

STATE OF THE ART

Certain derivatives of cyclopropane carboxylic acid derivatives are known having in the 3-position the group ROOC—CH=CH— having essentially E geometry. Examples of such prior art are French Pat. No. 2,185,612 as well as J. Chem. Soc., Perkin I (1974), p. 2470 and Pest. Sci. Vol. 7 (1976), p. 499. All the side chains of these compounds have predominantly E geometry. The processes used to prepare the derivatives lead almost exclusively to the E geometry for example (Agr. Biol. Chem. Vol. 34 (1970) p. 1119). Furthermore, for these compounds with the side chain geometry in the E state, it has not been possible to make evident any remarkable properties.

OBJECTS OF THE INVENTION

It is an object of the invention to provide the novel Z isomers of the compounds of formula I' as well as a novel process and novel intermediates for their preparation.

It is another object of the invention to provide pesticidal compositions and a novel method of killing insects, nematodes and vegetable and animal acariens.

It is a further object of the invention to provide novel compositions and method of combatting gales and to provide anthelmintic activity.

These and other objects and advantages of the invention will become obvious from the following detailed description.

THE INVENTION

The novel compounds of the invention are the isomers and mixtures thereof of cyclopropane carboxylic acid derivatives with a 3-unsaturated side chain of Z geometry of the formula

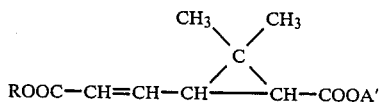

wherein A' is selected from the group consisting of (1) alkyl of 1 to 18 carbon atoms, (2) benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy and halogens,

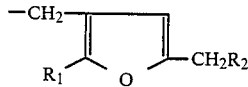

wherein $R_1$ is selected from the group consisting of hydrogen and methyl and $R_2$ is selected from the group consisting of —CH—C≡CH and monocyclic aryl,

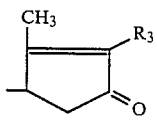

wherein $R_3$ is an aliphatic group of 2 to 6 carbon atoms containing at least one carboncarbon unsaturation,

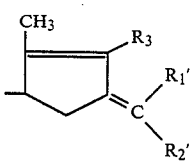

wherein $R_3$ has the above definition and $R_1'$ and $R_2'$ are individually selected from the group consisting of hydrogen, halogen, alkyl or 1 to 6 carbon atoms, aryl of 6 to 10 carbon atoms, cyano and alkoxycarbonyl of 2 to 5 carbon atoms

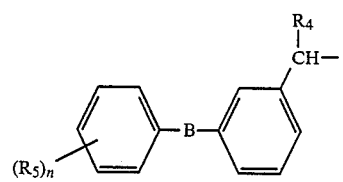

wherein B is selected from the group consisting of —CH$_2$—,

—O— and —S—, $R_4$ is selected from the group consisting of hydrogen, —CH$_3$, —CONH$_2$, —CSNH$_2$ and —C≡CH, n is an integer from 0, 1 or 2 and $R_5$ is selected from the group consisting of halogen and —CH$_3$

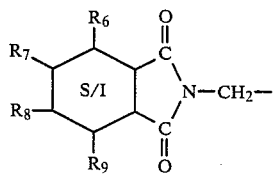

wherein $R_6$, $R_7$, $R_8$ and $R_9$ are selected from the group consisting of hydrogen, chlorine and methyl and S/I symbolizes an aromatic ring or dihydro or tetrahydro ring,

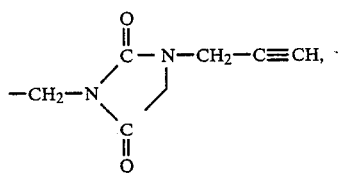    (9)

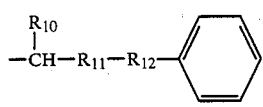    (10)

wherein $R_{10}$ is selected from the group consisting of hydrogen and CN, $R_{12}$ is selected from the group consisting of —$CH_2$— and —O— and $R_{11}$ is selected from the group consisting of thiazolyl and thiadiazolyl of which the bond with

can be found at any one of the available position $R_{12}$ being bonded to $R_{11}$ by the carbon atom included between the sulfur atom and a nitrogen atom,

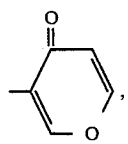    (11)

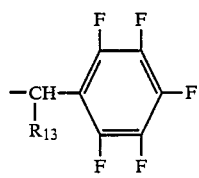    (12)

wherein $R_{13}$ is selected from the group consisting of hydrogen and CN,

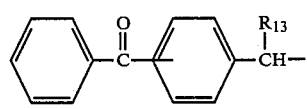    (13)

wherein $R_{13}$ has the above definition and the benzoyl is in the 3- or 4-position,

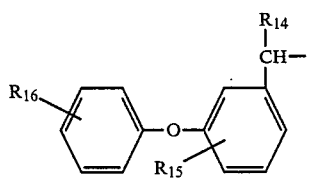    (14)

wherein $R_{14}$ is selected from the group consisting of hydrogen, methyl, ethynyl and —CN and $R_{15}$ and $R_{16}$ are individually selected from the group consisting of hydrogen, bromine and fluorine and

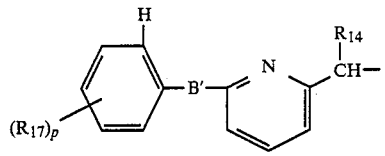    (15)

wherein $R_{14}$ has the above definition p is 0, 1 or 2, each $R_{17}$ is selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, —$CF_3$, 3,4-methylenedioxy, chlorine, bromine and fluorine, B' is selected from the group consisting of —O— and —S— and R is an optionally unsaturated alkyl of 1 18 carbon atoms.

Example of $R_2$ as monocyclic aryl is 5-benzyl-3-furyl-methyl and examples of $R_3$ are —$CH_2$—CH=$CH_2$, —$CH_2$—CH=CH—$CH_3$, —$CH_2$—CH=CH—$CH_2$—$CH_3$ and —$CH_2$—CH=CH—CH=$CH_2$. Examples of substituent (6) are 3-phenoxy-benzyl, α-ethynyl-3-phenoxy-benzyl, 3-benzoyl-benzyl, 1-(3-phenoxyphenyl)-ethyl and α-thiamido-3-phenoxy-benzyl.

The compounds of formula I' exist in isomeric forms due to the presence of asymmetric carbon atoms in the 1- and 2-positions of the ring and may also possess other asymetric centers in the alcohol portion thereof.

Examples of A' are alkyl such as methyl, ethyl, n-propyl isopropyl and n-butyl; benzyl optionally substituted with at least one alkyl such as methyl or ethyl; benzyl optionally substituted with at least one alkenyl such as vinyl, allyl, 2-methylallyl and isobutenyl; and benzyl substituted with at least one alkenyloxy such as vinyloxy, allyloxy, 2-methylallyloxy and isobutenyloxy; and benzyl substituted with at least one halogen such as chlorine, bromine or fluorine.

Examples of R are saturated alkyl such as methyl, ethyl, n-propyl, isopropyl, n-butyl, sec.-butyl, tert.-butyl, isobutyl, n-pentyl, n-hexyl, tert.-pentyl and neopentyl; cycloalkyl such as cyclopropyl, cyclobutyl, cyclopentyl and cyclohexyl; saturated alkyl substituted with at least one of the above cycloalkyl radicals; cycloalkyl such as cyclopropyl cyclobutyl, cyclopentyl or cyclohexyl substituted with at least one alkyl, and bonded to —COO— by anyone of its apices, such as 1-methycyclobutyl, 1-methylcyclopentyl, 1-methylcyclohexyl or 2,2,3,3-tetramethylcyclopropyl; alkenyl such as vinyl or 1,1-dimethylallyl; alkynyl such as ethynyl or propynyl.

A particular group of compounds with the double bond of the Z geometry have the formula

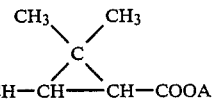    I wherein A is selected from the group consisting of (1) alkyl of 1 to 18 carbon atoms, (2) benzyl optionally substituted as before,

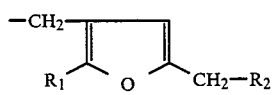    (3)

wherein $R_1$ and $R_2$ have the above definition,

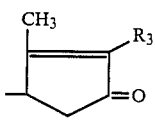

(4)

wherein R₃ has the above definition,

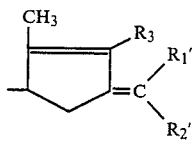

(5)

wherein R₃, R₁' and R₂' have the above definition,

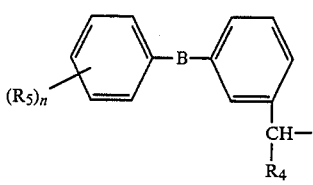

(6)

wherein B, R₄, R₅ and n' have the above definitions,

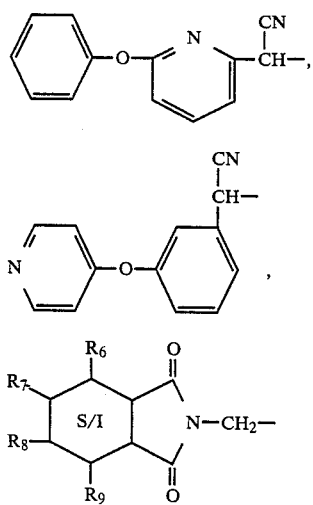

(7)

(8)

(9)

wherein S/I, R₆, R₇, R₈ and R₉ have the above definitions and

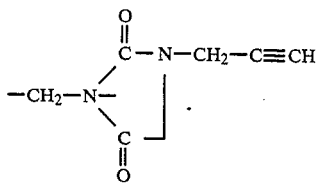

(10)

and R has the above definition as well as mixtures thereof.

The compounds of formula I or I' have the cyclopropane carboxylic acid in the 1R, cis or 1R, trans structure. R is preferably methyl as well as ethyl, n-propyl, isopropyl, tert. butyl and cyclopropylmethyl. Especially preferred for A are (4S) 3-methyl-2-(2-propenyl)-1-oxo-cyclopent-2-en-4-yl, (1,3,4,5,6,7-hexahydro-1,3-dioxo-2H-isoindol-2-yl)-methyl, (RS) cyano (6-phenoxy-2-pyridinyl)-methyl, 5-benzyl-3-furanyl-methyl 1-(3-propargyl-2,5-dioxo-imidazolidinyl)-methyl and (R) 3-phenoxy-phenyl-ethyl.

Examples of preferred compounds of formula I' are (1S) 2-methyl-4-oxo-3-(2-propenyl)-2-cyclopenten-1-yl (1R,cis) 2,2-dimethyl-3[(Z) 3-methoxy-3-oxo-1-propenyl)-cyclopropane-carboxylate, 1-(3-propargyl-2,5-dioxo-imidazolidinyl)-methyl (1R,cisΔZ) 2,2-dimethyl-3-(3-tert.-butoxy-3-oxo-1-propenyl)-cyclopropane-carboxylate, 1-(3-propargyl-2,5-dioxo-imidazolidinyl)-methyl (1R,cisΔZ) 2,2-dimethyl-3-(3-cyclopropylmethoxy-3-oxo-1-propenyl)-cyclopropane-carboxylate, 1(R)-(3-phenoxy-phenyl)-ethyl (1R,cis,ΔZ) 2,2-dimethyl-3-(3-isopropoxy-3-oxo-1-propenyl)-cyclopropane-carboxylate, 1-(3-propargyl)-2,5-dioxo-imidazolidinyl)-methyl (1R,cis,ΔZ) 2,2-dimethyl-3-(3-isopropoxy-3-oxo-1-propenyl)cyclopropane-carboxylate and 1(R)-(3-phenoxy-phenyl)-ethyl (1R,cis,ΔZ) 2,2-dimethyl-3-(3-isopropoxy-3-oxo-1-propenyl)-cyclopropane-carboxylate.

Examples of additional preferred compounds of the invention are (RS) 1,1,1-trifluoro-2-(6-phenoxy-pyridyl)-ethyl: (1R,cis,ΔZ) 2,2-dimethyl-3-[3-oxo-3-methoxy-1-propenyl]-cyclopropane-carboxylate; (RS) 1,1,1-trifluoro-2-(6-phenoxy-pyridyl)-ethyl (1R,cis,ΔZ) 2,2-dimethyl-3-[3-oxo-3-terbutoxy-1-propenyl]-cyclopropane-carboxylate; (R) metaphenoxy-phenyl ethyl (1R,cis,ΔZ) 2,2-dimethyl-3-[3-oxo-3-cyclopropyloxy-1-propenyl]cyclopropane-carboxylate; (RS) α-(trifluoromethyl)-3-phenoxy-benzyl (1R,cis,ΔZ) 2,2-dimethyl-3-[3-oxo-3-methoxy-1-propenyl]-cycloproane carboxylate; (RS) α-(trifluoromethyl)-metaphenoxy-benzyl (1R,cis,ΔZ) 2,2-dimethyl-3[-3-oxo-3-tertbutoxy-1-propenyl]-cyclopropane-carboxylate; (RS) trifluoromethyl-3-phenoxy-4-fluoro-benzyl (1R,cisΔZ) 2,2-dimethyl-3-[3-oxo-3-methoxy-propenyl]-cyclopropane-carboxylate; (RS)1,1,1-trifluoro-3-phenoxy-4-fluoro-phenyl-ethyl (1R,cis,ΔZ) 2,2-dimethyl-3-[3-oxo-3-tertbutoxy-1-propenyl]-cyclopropane-carboxylate; (RS) α-cyano-2-(6-phenoxy-pyridyl)-methyl (1R,cis,ΔZ)2,2-dimethyl-3-[3-oxo-3-cyclopropyloxy-1-propenyl]-cyclopropane-carboxylate; 3-phenoxy-benzyl (1R,cis,ΔZ) 2,2-dimethyl-3-[3-oxo-3-cyclobutyloxy-1-propenyl]-cyclopropane-carboxylate; 3-phenoxy-benzyl (1R,cis,ΔZ) 2,2-dimethyl-3-[3-oxo-3-cyclopropyloxy-1-propenyl]-cyclopropane-carboxylate; (1R) (3-phenoxy-phenyl)propyne (1R,cis,ΔZ) 2,2-dimethyl-3-[3-oxo-3-cyclopropyloxy-1-propenyl]-cyclopropane-carboxylate; (RS)α-cyano-3-benzyloxy-benzyl (1R,cis,ΔZ) 2,2-dimethyl-3[3-methoxy-3-oxo-1-propenyl]-cyclopropane-carboxylate; (RS)cyano-2-phenoxy-2-propenyl-(1Rcis,ΔZ)-2,2-dimethyl 3-/3-oxo-3-methoxy-propenyl/cyclopropane carboxylate; 4-indolyl-methyl (1R,cis,ΔZ)2,2-dimethyl-3[3-oxo-3-methoxy-1-propenyl]-cyclopropane-carboxylate; (RS)α-cyano-(4-indolyl)-methyl (1R,cis,ΔZ)2,2-dimethyl-3-[3-oxo-3-methoxy-1-propenyl]-cyclopropane-carboxylate; (RS) 4-chromanol (1R,cis,ΔZ) 2,2-dimethyl-3-[3-oxo-3-methoxy-1-propenyl]-cyclopropane-carboxylate; 2-phenoxy 2-propenyl (1R,cis,ΔZ) 2,2-dimethyl-3-[3-oxo-3-methoxy-1-propenyl]-cyclopropane-carboxylate; (RS) α-cyano-2-phenoxy-2-propenyl (1R,cis,ΔZ) 2,2-dimethyl-3-[3-oxo-3-tertbutoxy-1-propenyl]-cyclopropane-carboxylate; (RS) 1-(5-phenyl-isoxazol-3-yl)-ethyl (1R,cis,ΔZ)2,2-dimethyl-3-[-3-methoxy-3-oxo-1-propenyl]-cyclopropane-carboxylate; 1R (3-phenoxy-phenyl)-ethyl (1R,cis,ΔZ)2,2-dimethyl-3-[3-oxo-3- teramyloxy-1-propenyl]-cyclopropane-carboxylate; 1R (3-phenoxy-phenyl)-ethyl (1R,cis,ΔZ) 2,2-dimethyl-3-[1-methyl-cyclobutoxy-3-oxo-1-propenyl]-cyclopropane-carboxylate; (S)α-cyano (3-phenoxy-4-fluoro-benzyl) (1R,cis,ΔZ) 2,2-dimethyl-3-[3-oxo-3-propoxy-1-propenyl]-cyclopropane-carboxylate; (S)α-cyano-3-phenoxy-4-fluoro-benzyl (1R,cis,ΔZ) 2,2-dimethyl-3-[3-oxo-3-RS)-2-butoxy-1-propenyl]-cyclopropane-carboxylate; (S)α-cyano-(3-phenoxy-4-fluoro-benzyl) (1R,cis,ΔZ) 2,2-dimethyl-3-[3-oxo-3-teramyloxy-1-propenyl]-cyclopropane-carboxylate; 3-phenoxybenzyl (1R,cis,ΔZ) 2,2-dimethyl-3-[3-oxo-3-(1-methyl-cyclobutyloxy)-1-propenyl]-cyclopropane-carboxylate; benzyl (1R,cis,ΔZ) 2,2-dimethyl-3-[3-oxo-3-ethoxy-1-propenyl]-cyclopropane-carboxylate and 4-cyano-benzyl (1R,cis,ΔZ) 2,2-dimethyl-3-[3-oxo-3-methoxy-1-propenyl]-cyclopropane-carboxylate.

The novel process of the invention for the preparation of the compounds of formula I' comprises reacting a compound of the formula

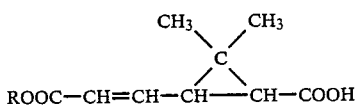

with the double bond having the Z geometry and R has the above definition or a functional derivative thereof with an alcohol of the formula

   III wherein A' has the above definition to obtain the corresponding compound of formula I'.

The preferred functional acid derivative is the acid chloride and the esterification is effected by known methods such as reacting the acid of the formula II with the alcohol of formula III in the presence of dicyclohexylcarbodiimide or diisopropylcarbodiimide.

The compounds of formula II are novel chemical products and may be prepared by reacting a compound of the formula

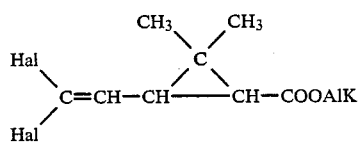

wherein Hal is a halogen and Alk is alkyl of 1 to 20 carbon atoms in a first step with an alkaline agent capable of taking off the halogen atom and in a second step either with an agent capable of introducing a carboxylic acid group to obtain a compound of the formula.

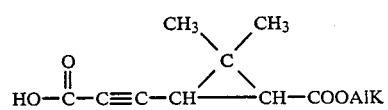

and reacting the latter with an esterification agent to obtain a compound of the formula

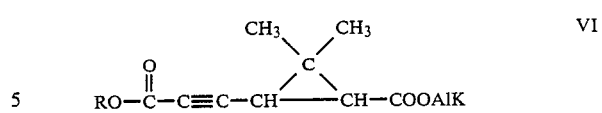

wherein R has the above definition or with an alkyl chloroformate of the formula

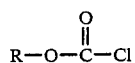   V' to obtain directly the corresponding compound of formula VI, reacting the compound of formula VI with a hydrogenation agent to obtain a compound of the formula

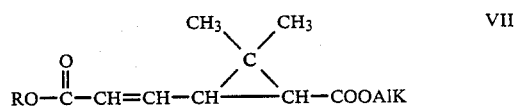

with the group —COOR being in the Z position, subjecting the latter to an acid hydrolysis agent capable of selectively cleaving the branched ester formation on the 1-position to obtain the compound of formula II.

The process for the preparation of a compound of formula I' comprises reacting a compound of the formula

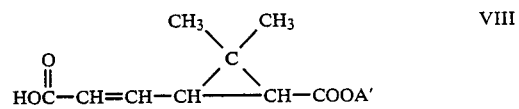

wherein A' has the above definition with an esterification agent to obtain the corresponding compound of formula I'.

The process for the preparation of a compound of formula VIII comprises reacting a compound of the formula

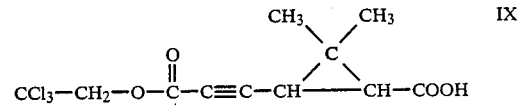

with a compound of formula III to obtain a compound of the formula

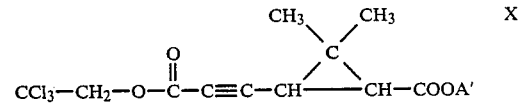

and reacting the latter with a cleaving agent for the ester group on the acetylenic side chain to obtain a compound of the formula

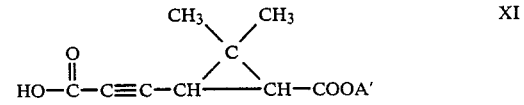

and subjecting the latter to a hydrogenation agent to obtain a compound of formula VIII.

In a preferred mode of the latter process, the esterification of the compound of formula IX with the alcohol of formula III is effected in the presence of dicyclohexylcarbodiimide or diisopropylcarbodiimide and the cleavage of the ester of formula X is effected with a metallic powder such as powdered zinc in an acid medium. The hydrogenation agent is preferably hydrogen in the presence of a catalyst such as palladium in the presence of traces of quinoline. The hydrogenation and esterification steps may be reversed.

Another embodiment of the process of the invention comprises reacting a compound of the formula

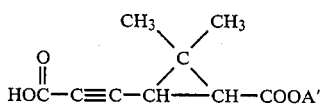

wherein A' has the above definition with an esterification agent to obtain a compound of the formula

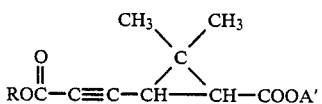

wherein A' and R have the above definition and reacting the latter with a hydrogenation agent to obtain the corresponding compound of formula I'. The preferred conditions are as discussed above.

The compound of formula IX may be prepared by reacting an acid of the formula

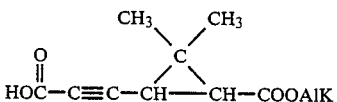

wherein AlK is alkyl of 1 to 18 carbon atoms with 2,2,2-trichloroethanol and subjecting the resulting ester to an acid hydrolysis agent.

The novel intermediate products of the invention are the compounds of formulae VIII, X, XI and XII.

The alcohol of formula III used in the process of the invention are generally know products. Horvever, some of the alcohols, that is to say the products of formula

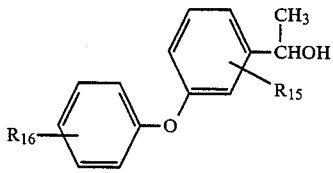

in which $R_{15}$ and $R_{16}$ are defined as herein before, are new chemical products and allow to obtain esters particularly remarkable from a biologic point of view.

The subject of the invention is also these alcohols as new industrial products and especially as intermediate product necessary for carrying out the invention.

Among these alcohols, there may be mentioned, in particular, the 3-phenoxy 4-fluro α-methyl-benzylic alcohol.

These alcohols can be prepared as indicated here in after in the experimental position, by reaction of an organo metallic product, for example, a methyl-magnesium halide, with the aldehydes corresponding to the desired alcohols.

The novel pesticidal compositions of the invention are comprised of a pesticidally effective amount of at least one compound of formula I' and an inert carrier. The compositions are useful to combat pests such as parasites of vegetables and of warm-blooded animals as well as domestic parasites and are particularly useful to combat insects, nematodes and parastic acariens which attack warm-blooded animals and vegetables.

The compositions of the invention are particularly useful to combat insects in the argicultural field for example to control aphides and larvae of lepidoptear and coleoptera and are usually used at a dose of 10 to 300 g of the compounds of formula I' per hectare. The compositions are also useful to control insects in the household, for example to combat flies, mosquitoes and bettles.

Certain of the compounds of formula I' possess an excellent knock-down power and the product of Example 1 is particularly remarkable on this point. The products of formula I' have the advantages of being very photostable and not being toxic to mammals. The various properties of the compounds of formula I' correspond perfectly to those required for modern agrochemical use permitting the protection of crops without damage to the environment.

The pesticidal compositions of the invention are useful to combat vegetable parasitic acariens and nematodes as well as to combat animal parasitic acariens such as ticks, especially ticks of Boophilus species, Hyalomnia species, Amblyomnia species and Rhipicephalus species and to combat all sorts of scabies such as sarcoptic scabies, psoroptic scabies and chorioptic scabies.

Particularly preferred pesticidal compositions of the invention are those wherein the active compound is (1S) 2-methyl-4-oxo-3-(2-propenyl)-2-cyclopenten-1-yl (1R, cis) 2,2-dimethyl-3-[(Z) 3-methoxy-3-oxo-1-propenyl]-cyclopropane-carboxylate, 1-(3-proparyl-2,5-dioxo-imidazolidinyl)-methyl (1R, cis, ΔZ) 2,2-dimethyl-3-(3-tert.-butoxy-3-oxo-1-propenyl)-cyclopropane-carboxylate, 1-(3-propargyl-2,5-dioxo-imidazolidinyl)-methyl (1R, cis, ΔZ)-2,2-dimethyl-3-(3-cyclopropylmethoxy-3-oxo-1-propenyl)-cyclopropane-carboxylate, 1(R)-(3-phenoxy-phenyl)-ethyl (1R, cis, ΔZ) 2,2-dimethyl-3-(3-isopropoxy-3-oxo-1-propenyl)-cyclopropane-carboxylate, 1-(3-propargyl-2,5-dioxo-imidazolidinyl)-methyl (1R, cis, ΔZ) 2,2-dimethyl-3-(3-isopropoxy-3-oxo-1-propenyl)-cyclopropane-carboxylate and 1(R)-(3-phenoxy-phenyl)-ethyl (1R, cis, ΔZ) 2,2-dimethyl-3-(3-isopropoxy-3-oxo-1-propenyl)-cyclopropane-carboxylate.

For the compositions intended for household or agricultural use, the compositions may also contain one or more other pesticidal agents. The compositions may be in the form of powders, granules, suspensions, emulsions, solutions, aerosol solutions, combustible bands and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I'.

In an advantageous operation for domestic use, the compositions are in the form of fumigants. These compositions advantageously have for their inactive portion a combustible serpentine or coil base or an incombustile fibrous substrate. In the latter case, the fumigant obtained after incorporation of the active ingredient of formula I' is placed in a heating apparatus such as an electromosquitoe destroyer. The usual active dose in this case is 0.03 to 95% by weight, preferably.

In the case of a serpentine insecticide, the inert support may be made, for example, of pyrethrum marc, Tabu powder (or *Machilus Thumbergii* leaf powder), powder of pyrethrum stems, cedar needle powder, sawdust such as pine sawdust starch and powder of coconut shells. The active dose in this case is preferably 0.03 to 1% by weight.

The compositions of the invention for household use may be prepared as a spraying oil containing the active ingredient and the oil may soak the wick of a lamp which is then subjected to combustion. The concentration of the compound of formula I' in the oil is preferably 0.03 to 95% by weight.

The insecticidal compositions as well as the acaricidal and nematocial compositions of the invention may also contain one or more other pesticides and are in the usual powder, granules, suspension, emulsions or solution form. For acaricide use, the compositions are preferably wettable powders for foliar spraying containing 1 to 80% of liquids for foliar spraying containing 1 to 500 g/l of the active ingredient. Also useful are powders for foliar powdering containing 0.5 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylenedioxy-benzene (piperonyl butoxide) or N-(2-ethylheptyl)-bicyclo-[2,2]5-heptene-2,3-dicarboximide or piperonylbis-2-(2'-n-butoxy-ethoxy)-ethyl acetal (tropital).

When the compositions are to be used to combat animal parasitic acariens, the active compounds of formula I' are very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, meal of animal origin such as fish meal, synthetic amino acids, mineral salts, vitamins and antioxidants.

The compositions of the invention show an excellent general tolerance and are equally useful as medicaments for treating affections created by ticks and scabies. The compositions may be used in veterinary and human medicines. In human medicine, the compositions may be used to combat lice as well as prevent or treat scabies. The compositions may also be used as anthelmintics.

The said medicaments may be administered externally by vaporization, by painting or by bathing. For veterinary usage, the compositions may also be administered by painting the dorsal spine by the "pour on" method as well as being administered digestively or parenterally.

The compositions of the invention are also useful as biocides or to regulate growth.

Another feature of the invention are insecticidal, acaricidal or nematocidal compositions containing as an active ingredient at least one compound of formula I' and as a second active ingredient at least one pyrethrinoid ester selected from the group consisting of esters of allethrolone, of 3,4,5,6-tetrahydrophthaliminomethyl alcohol, of 5-benzyl-3-furylmethyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols and 2,2-dimethyl-3-(2,2-dichlorovinyl)-cyclopropene-1-carboxylic acids, esters of α-cyano-3-phenoxybenzyl alcohols and 2,2-dimethyl-3-(2,2-dibromovinyl)-cyclopropane-1-carboxylic acids, esters of 3-phenoxy-benzyl alcohol and 2-p-chlorophenyl-2-isopropyl-acetic acids, esters of allethrolones, 3,4,5,6-tetrahydrophthalimidomethyl alcohol, 5-benzyl-3-furyl-methyl alcohol, 3-phenoxy-benzyl alcohol or α-cyano-3-phenoxy-benzyl alcohols and 2,2-dimethyl-3-(1,2,2,2-tetrahaloethyl)-cyclopropane-1-carboxylic acids where halo is fluorine, chlorine or bromine wherein the compounds of formula I are in all possible stereoisomer forms of the acids and alcohols of the pyrethrinoid esters.

The latter associated compositions of the invention are of particular interest for combatting by the polyvalence of their action a larger range of parasites or by manifesting a synergistic action in some cases.

The novel method of the invention for combatting parasites such as insects, nematodes and acariens comprises contacting the parasites with a pesticidally effective amount of at least one compound of formula I'.

In the following examples there are described several preferred embodiments to illustrate the invention. However, it should be understood that the invention is not intended to be limited to the specific embodiments.

EXAMPLE 1

(1S) 2-methyl-4-oxo-3-(2-propenyl)-2-cyclopenten-1-yl (1R, cis, ΔZ) 2,2-dimethyl-3-(3-methoxy-3-oxo-1-propenyl)-cyclopropane-carboxylate STEP A: Tert.-butyl (1R, cis) 2,2-dimethyl-3-(3-methoxy-3-oxo-1-propynyl)-cyclopropane-carboxylate 132 ml of a 20% solution of butyllithium in cyclohexane were added at −70° C. over 40 minutes to a mixture of 55 g of tert.-butyl (1R,cis) 2,2-dimethyl-3-(2,2-dibromovinyl)-cyclopropane-carboxylate and 550 ml of tetrahydrofuran and the mixture was stirred at −65° C. for 30 minutes after which 12.5 g of methyl chloroformate were added thereto. The mixture was stirred at −70° for 2 hours and then the temperature was allowed to rise to −20° C. The mixture was poured into an aqueous monosodium phosphate solution and the mixture was extracted with ether. The organic phase was washed, dried and evaporated to dryness under reduced pressure to obtain 38.3 g of residue. The latter was chromatographed over silica gel and was eluted with an 8-2 cyclohexane-ethyl acetate mixture to obtain 17.2 g of tert.-butyl (1R,cis) 2,2-dimethyl-3-(3-methoxy-3-oxo-1-propynyl)-cyclopropane-carboxylate.

STEP B: Tert.-butyl (1R,cis, 6ξZ) 2,2-dimethyl-3-(3-methoxy-3-oxo-1-propenyl)-cyclopropane-carboxylate A mixture of 12 g of the product of Step A, 240 ml of ethyl acetate, 2.4 g of 10% palladium hydroxide on barium sulfate and 2.4 ml of quinoline was hydrogenated and the mixture was filtered. The filtrate was dried and evaporated to dryness to obtain 11 g of tert.-butyl (1R, cis, ΔZ) 2,2-dimethyl-3-(3-methoxy-3-oxo-1-propenyl)-cyclopropane-carboxylate.

STEP C: (1R, cis, ΔZ) 2,2-dimethyl-3-(3-methoxy-3-oxo-1-propenyl)-cyclopropane-carboxylic acid A solution of 13.5 g of the product of Step B; 100 ml of toluene and 400 mg of p-toluene sulfonic acid was refluxed for 3 hours and was evaporated to dryness under reduced pressure to obtain 11.2 g of residue. The latter was chromatographed over silica gel and was eluted with a 60-39-1 cyclohexane-ethyl acetate-acetic acid mixture. The eluate was evaporated to dryness under reduced pressure to obtain 9.6 g of (1R, cis, ΔZ) 2,2-dimethyl-3-(3-methoxy-3-oxo-1-propenyl)-cyclopropane-carboxylic acid melting at 110° C. and having a specific rotation of $[\alpha]_D^{20} = +75.5° \pm 2°$ (c=1% in $CHCl_3$).

NMR Spectrum (deuterochloroform): Peaks at 1.3 ppm (hydrogens of geminal methyls); at 1.86–2 ppm (1-hydrogen of cyclopropyl); at 3.1–3.28–3.43 ppm (3-hydrogen of cyclopropyl); at 5.8–5.99 ppm (ethylenic hydrogen α to —COOCH$_3$); at 6.42–6.58 ppm and 6.61–6.77 ppm (ethylenic hydrogen β to COOCH$_3$); at 8.63 ppm (hydrogen of COOH); at 3.71 ppm (hydrogen of CH$_3$O).

STEP D: (1R, cis, ΔZ) 2,2-dimethyl-3-(3-methoxy-3-oxo-1-propenyl)-cyclopropane-carboxylic acid chloride 1 ml of thionyl chloride was added at 0° C. to a mixture of 1.8 g of the product of Step C and 10 ml of isoprene and the mixture was stirred at 0° C. for 30 minutes and at 20° C. for 4 hours. The mixture was evaporated to dryness under reduced pressure to obtain (1R, cis, ΔZ) 2,2-dimethyl-3-(3-methoxy-3-oxo-1-propenyl)-cyclopropane-carboxylic acid chloride which was used as is for the next step.

STEP E: (1S) 2-methyl-4-oxo-3-(2-propenyl)-2-cyclopenten-1-yl (1R, cis, ΔZ) 2,2-dimethyl-3-(3-oxo-3-methoxy-1-propenyl)-cyclopropane-carboxylate A solution of 888 mg of the product of Step D in 9 ml of benzene was added at 10° C. to a mixture of 761 mg of (4S) hydroxy-3-methyl-2-(2-propenyl)-2-cyclopenten-1-one, 5 ml of benzene and 0.4 ml of pyridine and the mixture was stirred for 16 hours and was then poured into water. The decanted organic phase was washed with water, dried and filtered and the filtrate was evaporated to dryness. The 1.9 g of residue was chromatographed over silica gel and was eluted with a 95-5 benzene-ethyl acetate mixture to obtain 1.06 g of (1S) 2-methyl-4-oxo-3-(2-propenyl)-2-cyclopenten-1-yl (1R, cis, ΔZ) 2,2-dimethyl-3-(3-oxo-3-methoxy-1-propenyl)-cyclopropane-carboxylate with a specific rotation of $[\alpha]_D = +71.5° \pm 2.5°$ (c=0.5% in CHCl$_3$).

NMR Spectrum (deuterochloroform): Peaks at 1.3 and 1.32 ppm (hydrogens of geminal methyls); at 1.9–2.05 ppm (1-hydrogen of cyclopropyl); at 31–3.3–3.4 (3-hydrogen of cyclopropyl); at 6.5 to 6.8 ppm (hydrogen of 1-carbon of ethenyl); at 5.8–6.04 ppm (hydrogen of 2-carbon of ethenyl); at 3.7 ppm (hydrogen of methoxy); at 5.6 to 5.8 ppm (4-hydrogen of (4S) 3-methyl-1-oxo-cyclopent-2-en-4-yl); at 2.95 to 3 ppm (1-hydrogen of propenyl); at 5.5 to 6.2 ppm (2-hydrogen of propenyl); at 4.8 to 5.2 ppm (3-hydrogen of propenyl).

EXAMPLE 2

(1S) 2-methyl-4-oxo-3-(2-propenyl)-2-cyclopenten-1-yl (1R, cis, ΔZ) 2,2-dimethyl-3-(3-ethoxy-3-oxo-1-propenyl)-cyclopropane-carboxylate STEP A: Tert.-butyl (1R,cis) 2,2-dimethyl-3-(3-hydroxy-3-oxo-1-propynyl)-cyclopropane-1-carboxylate 60 ml of a 20% solution of butyllithium in cyclohexane were added at −65° C. to a mixture of 26 g of tert.-butyl (1R, cis) 2,2-dimethyl-3-(2,2-dibromovinyl)-cyclopropane-carboxylate and 175 ml of anhydrous tetrahydrofuran and the mixture was stirred at −60° C. for one hour. A current of carbon dioxide was bubbled through the mixture for 90 minutes and the mixture was poured into an ice-water mixture containing N sodium hydroxide. The alkaline aqueous phase was acidified to a pH of 4 and was extracted with ether. The organic phase was dried and evaporated to dryness under reduced pressure. The residue was crystallized from petroleum ether (b.p.=60°–80° C. to obtain 8.3 g of tert.-butyl (1R,cis) 2,2-dimethyl-3-(3-hydroxy-3-oxo-1-propynyl)-cyclopropane-1-carboxylate melting at 144° C.

NMR Spectrum (deuterochloroform): Peaks at 1.22 and 1.37 ppm (hydrogens of geminal methyls); at 1.78 ppm (1- and 3-hydrogens of cyclopropyl); at 1.47 ppm (hydrogens of tert.-butyl) at 8.25 ppm (hydrogen of —COOH).

STEP B: Tert.-butyl (1R,cis) 2,2-dimethyl-3-(3-ethoxy-3-oxo-1-propynyl)-cyclopropane-carboxylate 1.5 ml of ethanol were added to a mixture of 4 g of the product of Step A, 3.4 g of dicyclohexylcarbodiimide, 6 mg of 4-dimethylamino-pyridine and 30 ml of methylene chloride and the mixture was stirred at 20° C. for 16 hours and was filtered. The filtrate was evaporated to dryness under reduced pressure and the 5.5 g of residue was chromatographed over silica gel. Elution with a 9-1 cyclohexane-ethyl acetate mixture yielded 4.25 g of tert.-butyl (1R,cis) 2,2-dimethyl-3-(3-ethoxy-3-oxo-1-propynyl)-cyclopropane-carboxylate.

NMR Spectrum (deuterochloroform): Peaks at 1.18–1.21 ppm and 1.36–1.47 ppm (hydrogens of geminal methyls); at 1.73 and 1.82 ppm (1- and 3-hydrogens of cyclopropyl); at 1.47 ppm (hydrogens of tert.-butyl); at 1.27–1.38–1.5 ppm and 4.0–4.13–4.25–4.36 ppm (hydrogens of ethyl).

STEP C: Tert.-butyl (1R,cis, ΔZ) 2,2-dimethyl-3-(3-ethoxy-3-oxo-1-propenyl)-cyclopropane-carboxylate A mixture of 4.3 g of the product of Step B, 100 ml of ethyl acetate, 800 mg of palladium hydroxide on barium sulfate and 0.8 ml of quinoline was hydrogenated and was filtered. The filtrate was acidified with 2N hydrochloric acid and was washed with water, dried and evaporated to dryness under reduced pressure. The 4.6 g of residue was chromatographed over silica gel and eluted with a 95-5 cyclohexaneethyl acetate mixture to obtain 2.5 g of tert.-butyl (1R,cis, ΔZ) 2,2-dimethyl-3-(3-ethoxy-3-oxo-1-propenyl)-cyclopropane-carboxylate.

NMR Spectrum (deuterochloroform): Peaks at 1.25 and 1.28 ppm (hydrogens of geminal methyls); at 1.78-1.93 ppm (1-hydrogen of cyclopropyl); at 2.98-3.1-3.2 ppm (3-hydrogen of cyclopropyl); at 6.4-6.6-6.8 ppm (ethylenic hydrogen α to cyclopropyl ring); at 5.7-5.9 ppm (ethylenic hydrogen on carbon attached to ethoxycarbonyl); at 4.0-4.13-4.25-4.36 ppm (hydrogen of methylene of ethoxy).

STEP D: (1R, cis ΔZ) 2,2-dimethyl-3-(3-ethoxy-3-oxo-1-propenyl)-cyclopropane-carboxylic acid A mixture of 2.3 g of the product of Step C, 20 mg of hydrated p-toluene sulfonic acid and 20 ml of toluene was refluxed for 40 minutes and was then evaporated to dryness under reduced pressure. The 2.1 g of residue were chromatographed over silica gel and eluted with a 60-39-1 cyclohexane-ethyl acetate-acetic acid mixture to obtain 1.7 g of product which was crystallized from cyclohexane to obtain 1.5 g of (1R, cis ΔZ) 2,2-dimethyl-3-(3-ethoxy-3-oxo-1-propenyl)-cyclopropane-carboxylic acid melting at 96° C.

NMR Spectrum (deuterochloroform): Peaks at 1.3 and 1.32 ppm (hydrogens of geminal methyls); at 1.86-2.02 ppm (1-hydrogen of cyclopropyl); at 3.15-3.28 ppm and 3.3-3.45 ppm (3-hydrogen of cyclopropyl); at 6.38-6.53 ppm and 6.55-6.73 ppm (hydrogen of branched ethylenic carbon on cyclopropyl); at 5.78-5.96 ppm (hydrogen of ethylenic carbon attached to ethoxy carbonyl); at 1.18-1.3-1.41 ppm (hydrogens of

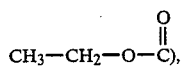

at 4.0-4.13 ppm and 4.25-4.36 ppm (hydrogens of

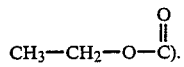

STEP E: (1S) 2-methyl-4-oxo-3-(2-propenyl)-2-cyclopenten-1-yl (1R, cis, ΔZ) 2,2-dimethyl-3-(3-ethoxy-3-oxo-1-propenyl)-cyclopropane-carboxylate A solution of 900 mg (4S) 4-hydroxy-3-methyl-2-(2-propenyl)-2-cyclopenten-1-one in 1 ml of methylene chloride was added to a mixture of 1 g of dicyclohexylcarbodiimide, 6 mg of 4-dimethylamino-pyridine, 12 ml of methylene chloride and 1.1 g of the product of Step D in a balloon flask and the mixture was stirred at room temperature for 16 hours and was filtered. The filtrate was evaporated to dryness under reduced pressure and the 2.4 g of residue was chromatographed over silica gel. Elution with a 6-4 n-hexane-isopropyl ether mixture yielded 1.3 g of (1S) 2-methyl-4-oxo-3-(2-propenyl)-2-cyclopenten-1-yl (1R, cis, ΔZ) 2,2-dimethyl-3-(3-ethoxy-3-oxo-1-propenyl)-cyclopropane-carboxylate with a specific rotation of $[\alpha]_D^{20} = +34° \pm 2°$ (c=0.6% in benzene).

NMR Spectrum (deuterochloroform): Peaks at 1.27 ppm (hydrogens of geminal methyls); at 3.1 to 3.4 ppm (3-hydrogen of cyclopropyl); at 6.4 to 6.8 ppm (1-hydrogen of ethenyl); at 1.17, 1.28, 1.4 and 4 to 4.4 ppm (hydrogen of ethoxy); at 4.7 to 5.2 ppm (3-hydrogen of propenyl).

EXAMPLE 3

(1S) 2-methyl-4-oxo-3-(2-propenyl)-2-cyclopenten-1-yl (1R, cis, ΔZ) 2,2-dimethyl-3-(3-oxo-3-propoxy-1-propenyl)-cyclopropane-carboxylate STEP A: Tert.-butyl (1R, cis) 2,2-dimethyl-3-(3-propoxy-3-oxo-1-propynyl)-cyclopropane-carboxylate 55 ml of a 20% solution of butyllithium in cyclohexane were added at −60° C. to a mixture of 22.8 g of tert.-butyl (1R, cis) 2,2-dimethyl-3-(2,2-dibromovinyl)-cyclopropane-carboxylate and 250 ml of tetrahydrofuran and the mixture was stirred at −65° C. for one hour. Then, 8 ml of n-propyl chloroformate were added thereto at −65° C. over 15 minutes and the mixture was stirred at −65° C. for one hour after which the temperature was allowed to rise to room temperature. The mixture was stirred at room temperature for one hour and was poured into aqueous saturated monosodium phoshate solution with stirring. The mixture was extracted with ether and the organic phase was washed with water, dried and evaporated to dryness under reduced pressure to obtain 19.5 g of an oil. The latter was chromatographed over silica gel and was eluted with a 9-1 cyclohexane-ethyl acetate mixture to obtain 11.5 g of tert.-butyl (1R, cis) 2,2-dimethyl-3-(3-propoxy-3-oxo-1-propynyl)-cyclopropane-carboxylate.

NMR Spectrum (deuterochloroform): Peaks at 1.17 and 1.37 ppm (hydrogens of geminal methyls); at 1.72 ppm (1- and 3-hydrogens of cyclopropyl); at 1.44 ppm (hydrogens of tert.-butyl); at 4.0-4.12-4.23 ppm (hydrogen of 1-methylene of propoxycarbonyl); at 0.83-0.95-1.06 ppm (hydrogens of

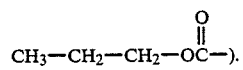

STEP B: Tert.-butyl (1R, cis, ΔZ) 2,2-dimethyl-3-(3-propoxy-3-oxo-1-propenyl)-cyclopropane-carboxylate A mixture of 7 g of the product of Step A, 140 ml of ethyl acetate, 1.4 g of 10% palladium hydroxide or barium sulfate and 1.4 ml of quinoline was hydrogenated and was filtered. The filtrate was washed with 2N hydrochloric acid, then with water, was dried and evaporated to dryness under reduced pressure. The 7.2 g of residue were chromatographed over silica gel and eluted with a 95-5 cyclohexane-ethyl acetate mixture to obtain 6.1 g of tert.-butyl (1R, cis, ΔZ) 2,2-dimethyl-3-(3-propoxy-3-oxo-1-propenyl)-cyclopropane-carboxylate.

NMR Spectrum (deuterochloroform): Peaks at 1.25 and 1.29 ppm (hydrogens of geminal methyls); at 1.5 to 2.03 ppm (1-hydrogen of cyclopropyl); at 3.03 to 3.35 ppm (3-hydrogen of cyclopropyl); at 6.5-6.66 ppm and 6.69-6.85 ppm (hydrogen of ethylenic carbon attached to cyclopropyl); at 5.82-6.0 ppm (hydrogen of ethylenic carbon attached to propoxycarbonyl); at 4.02-4.12-4.23 ppm (hydrogen of 1-methylene of propoxycarbonyl); at 0.86-0.98-1.1 ppm (hydrogen of methyl of propoxycarbonyl).

STEP C: (1R, cis, ΔZ) 2,2-dimethyl-3-(3-propoxy-3-oxo-1-propenyl)-cyclopropane-carboxylic acid A mixture of 5.8 g of the product of Step B, 200 mg of hydrated p-toluene sulfonic acid and 60 ml of toluene was refluxed for one hour and was then evaporated to dryness under reduced pressure. The 5 g of residue were chromatographed over silica gel and eluted with a 70-29-1 cyclohexane-ethyl acetate-acetic acid mixture to obtain 4.2 g of (1R, cis, ΔZ) 2,2-dimethyl-3-(3-propoxy-3-oxo-1-propenyl)-cyclopropane-carboxylic acid.

NMR Spectrum (deuterochloroform): Peaks at 1.27 and 1.29 ppm (hydrogens of geminal methyls); at 1.86–2 ppm (1-hydrogen of cyclopropyl); at 3.13 to 3.45 ppm (3-hydrogen of cyclopropyl); at 5.8–6 ppm (hydrogen of ethylenic carbon attached to propoxycarbonyl); at 6.4–6.56–6.59 ppm hydrogen of ethylenic carbon attached to cyclopropyl); at 3.98–4.08–4.18 ppm (hydrogen of 1-methylene of propoxycarbonyl); at 0.83–0.95–1.06 ppm (hydrogens of methyls of propoxy carbonyl).

STEP D: (1S) 2-methyl-4-oxo-3-(2-propenyl)-2-cyclopenten-1-yl (1R, cis, ΔZ) 2,2-dimethyl-3-(3-oxo-3-propoxy-1-propenyl)-cyclopropane-carboxylate Using the procedure of Step E of Example 2, 1.5 g of the product of Step C and 1.1 g of (4S) 4-hydroxy-3-methyl-2-(2-propenyl)-2-cyclopenten-1-one were reacted to obtain 3.1 g of product which were chromatographed over silica gel. Elution with a 7-3 hexane-isopropyl ether mixture and evaporation of the eluate to dryness yielded 1.7 g of (1S) 2-methyl-4-oxo-3-(2-propenyl)-2-cyclopenten-1-yl (1R, cis, ΔZ) 2,2-dimethyl-3-(3-oxo-3-propoxy-1-propenyl)-cyclopropane-carboxylate with a specific rotation of $[\alpha]_D^{20} = +39.5° \pm 2.5°$ (c=0.5% in benzene).

NMR Spectrum (deuterochloroform): Peaks at 1.3 and 1.31 ppm (hydrogens of geminal methyls); at 3.1 to 3.42 ppm (3-hydrogen of cyclopropyl); at 6.4 to 6.8 ppm (1-hydrogen of ethenyl); at 5.8–6 ppm (2-hydrogen of ethenyl); at 4.08–4.2 ppm (hydrogen of propoxy γ to COO−); at 0.83–0.95–1.06 ppm (hydrogen of propoxy γ to COO−); at 5.6 to 5.7 ppm (4-hydrogen of (4S)-methyl-2-(2-propenyl)-1-oxo-cyclopent-2-en-yl); at 4.7 to 5.2 ppm (3-hydrogen of propenyl).

EXAMPLE 4

(1S) 2-methyl-4-oxo-3-(2-propeyl)-2-cyclopenten-1-yl (1R, cis, ΔZ) 2,2-dimethyl-3-[3-isopropoxy-3-oxo-1-propenyl]-cyclopropane-carboxylate STEP A: Tert.-butyl (1R, cis, ΔZ) 2,2-dimethyl-3-[3-hydroxy-3-oxo-1-propenyl]-cyclopropane-carboxylate A mixture of 2 g of tert.-butyl (1R, cis) 2,2-dimethyl-3-[3-hydroxy-3-oxo-1-propynyl]-cyclopropane-carboxylate, 40 ml of ethyl acetate, 0.38 g of 10% palladium hydroxide on barium sulfate and 0.4 ml of quinoline was hydrogenated and was then filtered. The filtrate was washed with 0.5N hydrochloric acid then with water until the wash water was neutral, was dried and evaporated to dryness under reduced pressure to obtain 2 g of tert-butyl (1R, cis, ΔZ) 2,2-dimethyl-3-[3-hydroxy-3-oxo-1-propenyl]-cyclopropane-carboxylate melting at 94° C.

STEP B: Tert.-butyl (1R, cis, ΔZ) 2,2-dimethyl-3-[3-isopropoxy-3-oxo-1-propenyl]-cyclopropane-carboxylate 2 g of O-isopropyl-N,N'-diisopropyl-isourea were added to a mixture of 2.7 g of the product of Step A in 10 ml of ethyl acetate and the mixture was stirred at room temperature for one hour, refluxed for 90 minutes and then was cooled to 20° C. The mixture was filtered and the filtrate was evaporated to dryness under reduced pressure to obtain 3.5 g of an oil which was chromatographed over silica gel. Elution with a 7-3 benzene-cyclohexane mixture yielded 1 g of tert.-butyl (1R, cis ΔZ) 2,2-dimethyl-3-[2-isopropoxy-3-oxo-1-propenyl]-cyclopropane carboxylate which was used as is for the next step.

STEP C: (1R, cis, ΔZ) 2,2-dimethyl-3-(3-isopropoxy-3-oxo-1-propenyl)-cyclopropane-carboxylic acid A mixture of 1.4 g of the product of Step B, 100 mg of p-toluene sulfonic acid and 14 ml of toluene was heated with stirring at 120° C. for 2½ hours and was then evaporated to dryness under reduced pressure. The residue was crystallized from isopropyl ether and the mixture was iced and vacuum filtered. The product was dried to obtain 900 mg of (1R, cis, ΔZ) 2,2-dimethyl-3-(3-isopropoxy-3-oxo-1-propenyl)-cyclopropane-carboxylic acid melting at 98° C.

STEP D: (1R, cis, ΔZ) 2,2-dimethyl-3-(3-isopropoxy-3-oxo-1-propenyl)-cyclopropane-carboxylic acid chloride A mixture of 900 mg of the product of Step C, 9 ml of isoprene and 1 ml of thionyl chlorid was stirred at room temperature for 4 hours and was then evaporated to dryness under reduced pressure to obtain 1.4 g of (1R, cis, ΔZ) 2,2-dimethyl-3-(3-isopropoxy-3-oxo-1-propenyl)-cyclopropane-carboxylic acid chloride which was used as is for the next step.

STEP E: (1S) 2-methyl-4-oxo-3-(2-propenyl)-cyclopenten-1-yl (1R, cis, ΔZ) 2,2-dimethyl-3-(3-isopropoxy-3-oxo-1-propenyl)-cyclopropane-carboxylate A mixture of 1.4 g of the product of Step D, 10 ml of benzene, 750 mg of (4S) 4-hydroxy-3-methyl-2-(2-propenyl)-cyclopent-2-ene-1-one and 1.5 ml of pyridine was stirred for 3 hours and was then poured into a mixture of 100 ml of ice water and 20 ml of 2N hydrochloric acid. The mixture was extracted with ethyl acetate and the organic phase was washed with water until the wash water was neutral, was dried, and filtered. The filtrate was evaporated to dryness under reduced pressure and the 2.3 g of residue was chromatographed over silica gel. Elution with an 8-2 cyclohexane-ethyl acetate mixture yielded 486 mg of (1S) 2-methyl-4-oxo-3-(2-propenyl)-cyclopenten-1-yl (1R, cis, ΔZ) 2,2-dimethyl-3-(3-isopropoxy-3-oxo-1-propenyl)-cyclopropane-carboxylate with a specific rotation of $[\alpha]_D^{20} = +26° \pm 2°$ (c=0.5% in benzene).

NMR Spectrum (deuterochloroform): Peaks at 1.28 and 1.32 ppm (hydrogens of geminal methyls); at 1.88–2 ppm (1-hydrogen of cyclopropyl); at 3.11–3.4 ppm (3-hydrogen of cyclopropyl); at 6.4 to 6.8 ppm (1-hydrogen of ethenyl); at 5.8–6 ppm (2-hydrogen of ethenyl); at 5 ppm (hydrogen of carbon of isopropyl α to —C=O); at 1.3 ppm (hydrogens of carbons of isopropyl β- to C=O); at 4.8 to 5.2 ppm (3-hydrogen of propenyl); at 5.7 ppm (4-hydrogen of (4S) 3-methyl-2-(2-propenyl)-1-oxo-cyclopent-2-en-4-yl); at 2 ppm (3-hydrogen of (4S) 3-methyl-2-(2-propenyl)-1-oxo-cyclopent-2-en-4-yl).

EXAMPLE 5

(RS) cyano-(6-phenoxy-2-pyridinyl)-methyl (1R, cis ΔZ)
2,2-dimethyl-3-(3-methoxy-3-oxo-1-propenyl)-cyclopropane-carboxylate 2 ml of pyridine and then 5.2 g of dicyclohexylcarbodiimide were added to a mixture of 4.96 g of (1R, cis ΔZ) 2,2-dimethyl-3-(3-methoxy-3-oxo-1-propenyl)-cyclopropane-carboxylic acid in 75 ml of methylene chloride and after stirring the mixture for a few minutes, 5.9 g of (RS) α-hydroxy-6-phenoxy-2-pyridine-acetonitrile and then 0.1 g of 4-dimethylamino pyridine were added to the mixture. The mixture was stirred for one hour and was then filtered and the filtrate was evaporated to dryness. The residue was chromatographed over silica gel and was eluted with an 85-15 cyclohexane-ethyl acetate-mixture to obtain 7.7 g of (RS) cyano-(6-phenoxy-2-pyridinyl) methyl (1R, cis, ΔZ) 2,2-dimethyl-3(3-methoxy-3-oxo-1-propenyl)-cyclopropane-carboxylate with a specific rotation of $[\alpha]_D^{20} = +59° \pm 2.5°$ (c=0.5% in chloroform).

NMR Spectrum (deuterochloroform): Peaks at 6.3 ppm (hydrogen on carbon attached to —CN); at 1.22–1.27 ppm and 1.3 ppm (hydrogens of geminal methyls); at 3.17 to 3.5 ppm (3-hydrogen of cyclopropyl); at 3.7 ppm (hydrogens of methoxy); at 5.8 to 6.0 ppm (ethylenic hydrogen α to COO⁻); at 6.3 to 6.6 ppm (ethylenic hydrogen β to COO⁻); at 6.9 to 7 ppm (3- and 5-hydrogens of pyridine); at 7.7–7.8–7.9 ppm (4-hydrogen of pyridine).

EXAMPLE 6

(1,3,4,5,6,7-hexahydro-1,3-dioxo-2H-isoindol-2-yl)-methyl (1R, cis,ΔZ)
2,2-dimethyl-3-(3-methoxy-3-oxo-1-propenyl)-cyclopropane-carboxylate Using the procedure of the last Step of Example 1, 1.5 g of (1R, cis, ΔZ) 2,2-dimethyl-3-(3-oxo-3-methoxy-1-propenyl)-cyclohexane-carboxylic acid chloride and 1.4 g of 1,3,4,5,6,7-hexahydro-2-hydroxymethyl-1H-isoindole-1,3-(2H)-dione were reacted to obtain 3 g of a product which was chromatographed over silica gel. Elution with an 8-2 cyclohexane-ethyl acetate mixture and evaporation of the elute yielded 1.86 g of (1,3,4,5,6,7-hexahydro-1,3-dioxo-2H-isoindol-2-yl)-methyl (1R, cis, ΔZ) 2,2-dimethyl-3-(3-methoxy-3-oxo-1-propenyl)-cyclopropane-carboxylate.

NMR Spectrum (deuterochloroform): Peaks at 1.27 and 1.3 ppm (hydrogens of geminal methyls); at 1.78–1.93 ppm (1-hydrogen of cyclopropyl); at 3.06–3.53 ppm (3-hydrogen of cyclopropyl); at 5.8–6 ppm and 6.4 to 6.8 ppm (2-hydrogen of ethenyl); at 3.7 ppm (hydrogens of C₃O—); at 1.6 to 2 ppm (4-, 5-6 and 7-hydrogens of indole); at 5.5 ppm (hydrogens of —CH₂—α to COO attached to 1-position of cyclopropyl.

EXAMPLE 7

(5-benzyl-3-furanyl) methyl (1R, cis, ΔZ)
2,2-dimethyl-3-(3-methoxy-3-oxo-1-propenyl)-cyclopropane-carboxylate Using the procedure of the last Step of Example 1, 3.22 g of (1R, cis, ΔZ) 2,2-dimethyl-3-(3-methoxy-3-oxo-1-propenyl)-cyclopropane-carboxylic acid chloride and 2.8 g of 5-benzyl-Δ³-furanyl-methanol were reacted to obtain 6.3 g of a product which was chromatographed over silica gel. Elution with an 8-2 cyclohexane-ethyl acetate mixture yielded 2.33 g of (5-benzyl-3-furanyl)-methyl (1R, cis, ΔZ) 2,2-dimethyl-3-(3-methoxy-3-oxo-1-propenyl)-cyclopropane-carboxylate with a specific rotation of $[\alpha]_D^{20} = +48° \pm 1.5°$ (c=0.7% in chloroform).

NMR Spectrum (deuterochloroform): Peaks at 1.26–1.28 ppm (hydrogens of geminal methyls); at 1.86–2.02 ppm (1-hydrogen of cyclopropyl); at 3.0 to 3.3 ppm (3-hydrogen of cyclopropyl); at 6.4 to 6.8 ppm (1-hydrogen of ethenyl); at 5.8–5.9 ppm (2-hydrogen of ethenyl); at 3.7 ppm (hydrogens of CH₃O—); at 4.9 ppm (hydrogens of —CH₂— to —COO attached to 1-position of cyclopropyl); at 7.3 ppm (2-hydrogen of furanyl); at B 6 ppm (4-hydrogen of furanyl); at 7.2 ppm (aromatic hydrogens).

EXAMPLE 8

[1-(2-propenyl)-2,4-dioxo-imidazolidin-3-yl]-methyl (1R, cis, ΔZ)
2,2-dimethyl-3-(3-propoxy-3-oxo-1-propenyl)-cyclopropane-carboxylate 1 g of dicyclohexylcarbodiimide was added to a solution of 1.2 g of (1R, cis, ΔZ) 2,2-dimethyl-3-(3-propoxy-3-oxo-1-propenyl)-cyclopropane-carboxylic acid, 20 ml of methylene chloride and 100 ml of 4-dimethylamino-pyridine and then 900 mg of 3-hydroxymethyl-1-(2-propynyl)-2,4-dioxo-imidazolidine were added thereto with stirring. The mixture was stirred at 20° C. for 16 hours and was then filtered. The filtrate was washed with N hydrochloric acid and then with water until the wash water was neutral, dried and evaporated to dryness under reduced pressure. The oil residue was chromatographed over silica gel and was eluted with an 8-2 benzene-ethyl acetate mixture to obtain 1.2 g of [1-(2-propenyl)-2,4-dioxo-imidazolidin-3-yl]-methyl (1R, cis, ΔZ) 2,2-dimethyl-3-(3-propoxy-3-oxo-1-propenyl)-cyclopropane-carboxylate with a specific rotation of $[\alpha]_D^{20} = +2° \pm 1°$ (c=0.5% in benzene).

NMR Spectrum (deuterochloroform): Peaks at 1.25 and 1.28 ppm (hydrogens of geminal methyls); at 1.83–1.97 ppm (1-hydrogen of cyclopropyl); at 3.0 to 3.4 ppm (3-hydrogen of cyclopropyl); at 6.4 to 6.7 ppm (1-hydrogen of ethenyl); at 5.6–5.8 ppm (2-hydrogen of ethenyl); at 4–4.1–4.2 ppm (hydrogen of propoxy α to C=O); at 0.83–0.95–1.07 ppm (hydrogen of propoxy α to C=O); at 2.33–2.37–2.41 ppm (3-hydrogens of propynyl); at 4 ppm (3-hydrogen of 2,5-dioxo-imidazolidinyl); at 4.2–4.3 ppm (hydrogens of —CH₂—α to triple bond).

EXAMPLE 9 m-phenoxy-benzyl (1R, cis, ΔZ)
2,2-dimethyl-3-(3-methoxy-3-oxo-1-propenyl)-cyclopropane-carboxylate.

A mixture of 2 g of (1R, cis, ΔZ) 2,2-dimethyl-3-(3-methoxy-3-oxo-1-propenyl)-cyclopropane-carboxylic acid, 0.9 ml of pyridine, 2.5 g of dicyclohexylcarbodiimide and 20 ml of methylenechloride was stirred for 10 minutes and then 2.48 of m-phenoxy-benzyl alcohol were added thereto. The mixture was stirred for 90 minutes and 40 mg of 4-dimethylamino-pyridine were added thereto. The mixture was stirred for 2½ hours and was filtered and the filtrate was evaporated to dryness under reduced pressure. The residue was chromatographed over silica gel and was eluted with a 9-1 cyclohexane-ethyl acetate mixture to obtain 3 g of m-phenoxy-benzyl (1R, cis, ΔZ) 2,2-dimethyl-3-(3- methoxy-3-oxo-1-propenyl)-cyclopropane-carboxylate with a specific rotation of $[\alpha]_D^{20} = +48°\pm1.2°$ (c=1% in chloroform).

Analysis: $C_{23}H_{24}O_5$; molecular weight=380.444; Calculated: %C 72.61; %H 6.36; Found: 72.7; 6.4.

EXAMPLE 10

α(R,S) cyano-[3-(4-bromophenoxy)-phenyl]-methyl (1R, cis, ΔZ) 2,2-dimethyl-3-(3-methoxy-3-oxo-1-propenyl)-cyclopropane-carboxylate Using the procedure of Example 9, (1R, cis, ΔZ) 2,2-dimethyl-3-(3-methoxy-3-oxo-1-propenyl)-cyclopropane-carboxylic acid and α(RS) cyano-[3-(4-bromophenoxy)-phenyl]-methanol were reacted to obtain α(R,S) cyano-[3-(4-bromophenoxy)-phenyl]-methyl (1R, cis, ΔZ) 2,2-dimethyl-3-(3-methoxy-3-oxo-1-propenyl)-cyclpropane-carboxylate.

Analysis: $C_{24}H_{22}BrNO_5$; molecular weight=484.342; Calculated: %C 59.51; %H 4.58; %N 2.89; %Br 16.50; Found: 59.7; 4.6; 2.8; 16.2.

NMR Spectrum (deuterochloroform): Peaks at 1.26 to 1.34 ppm (hydrogens of geminal methyls); at 1.97–2.06 ppm and 3.22 to 3.48 ppm (1- and 3-hydrogens of cyclopropyl); at 3.7–3.73 ppm (hydrogens of $CH_3$—COO); at 5.85–5.98 ppm and 5.9–6.03 ppm (ethylenic hydrogens of ester side chain); at 6.33 ppm hydrogen of —CH—CN); at 6.43 to 6.67 ppm (ethylenic hydrogens of cyclopropyl); at 6.85 to 7.52 ppm (hydrogens of bromophenyl); at 6.94 to 7.55 ppm (aromatic hydrogens).

EXAMPLE 11

4-oxo-4(H)-pyran-3-yl (1R, cis, ΔZ) 2,2-dimethyl-3-(3-methoxy-3-oxo-1-propenyl)-cyclopropane-carboxylate Using the procedure of Example 9, (1R, cis, ΔZ) 2,2-dimethyl-3-(3-methoxy-3-oxo-1-propenyl)-cyclopropane-carboxylic acid and 4-oxo-(4H)-pyran-3-yl alcohol were reacted to obtain 4-oxo-4(H)-pyran-3-yl (1R, cis, ΔZ) 2,2-dimethyl-3-(3-methoxy-3-oxo-1-propenyl)-cyclopropane-carboxylate melting at 106° C. and having a specific rotation of $[\alpha]_D^{20} = +153°\pm2.5°$ (c=0.8% in benzene).

EXAMPLE 12

1(R)-(3-phenoxyphenyl)-ethyl (1R, cis, ΔZ) 2,2-dimethyl-3-(3-isopropoxy-3-oxo-1-propenyl)-cyclopropane-carboxylate Using the procedure of Example 9, (1R, cis, ΔZ) 2,2-dimethyl-3-(3-isopropoxy-3-oxo-1-propenyl)-cyclopropane-carboxylic acid and 1-(R) (3-phenoxyphenyl)-ethanol were reacted to obtain 1(R)-(3-phenoxyphenyl)-ethyl (1R, cis, ΔZ) 2,2-dimethyl-3-(3-isopropoxy-3-oxo-1-propenyl)-cyclopropane-carboxylate with a specific rotation of $[\alpha]_D^{20} = +140°\pm2.5°$ (c=1% in benzene).

EXAMPLE 13

1(R)-(3-phenoxyphenyl)-ethyl (1R, cis, ΔZ) 2,2-dimethyl-3-(3-ethoxy-3-oxo-1-propenyl)-cyclopropane-carboxylate Using the procedure of Example 9, (1R, cis, ΔZ) 2,2-dimethyl-3-(3-ethoxy-3-oxo-1-propenyl)-cyclopropane-carboxylic acid and 1(R)-(3-phenoxyphenyl)-ethanol were reacted to obtain 1(R)-(3-phenoxyphenyl)-ethyl (1R, cis, ΔZ) 2,2-dimethyl-3-(3-ethoxy-3-oxo-1-propenyl)-cyclopropane-carboxylate with a specific rotation of $[\alpha]_D^{20} = +145°\pm2.5°$ (c=1% in benzene).

EXAMPLE 14

1(R) (3-phenoxyphenyl)-ethyl (1R, cis, ΔZ) 2,2-dimethyl-3-(3-methoxy-3-oxo-1-propenyl)-cyclopropane-carboxylate Using the procedure of Example 9, (1R, cis, ΔZ) 2,2-dimethyl-3-(3-methoxy-3-oxo-1-propenyl)-cyclopropane-carboxylic acid and 1(R) (3-phenoxyphenyl)-ethanol were reacted to obtain 1(R) (3-phenoxyphenyl)-ethyl (1R, cis, ΔZ) 2,2-dimethyl-3-(3-methoxy-3-oxo-1-propenyl)-cyclopropane-carboxylate having a specific rotation of $[\alpha]_D^{20} = +130.5°\pm2.5°$ (c=1% in chloroform).

EXAMPLE 15

(RS) α-cyano-(3-benzoyl-phenyl)-methyl (1R, cis, ΔZ) 2,2-dimethyl-3-(3-methoxy-3-oxo-1-propenyl)-cyclopropane-carboxylate Using the procedure of Example 9, (1R, cis ΔZ) 2,2-dimethyl-3-(3-methoxy-3-oxo-1-propenyl)-cyclopropane-carboxylic acid and (RS) α-cyano-(3-benzoyl-phenyl)-methanol were reacted to obtain (RS) α-cyano-(3-benzoyl-phenyl)-methyl (1R, cis ΔZ) 2,2-dimethyl-3-(3-methoxy-3-oxo-1-propenyl)-cyclopropane-carboxylate with a specific rotation of $[\alpha]_D^{20} = +43°\pm1°$ (c=1% in toluene).

EXAMPLE 16

(3-benzoyl-phenyl)-methyl (1R, cis, ΔZ) 2,2-dimethyl-3-(3-methoxy-3-oxo-1-propenyl)-cyclopropane-carboxylate Using the procedure of Example 9, (1R, cis, ΔZ) 2,2-dimethyl-3-(3-methoxy-3-oxo-1-propenyl)-cyclopropane-carboxylic acid and (3-benzoyl-phenyl)-methanol were reacted to obtain (3-benzoyl-phenyl)-methyl (1R, cis, Z) 2,2-dimethyl-3-(3-methoxy-3-oxo-1-propenyl)-cyclopropane-carboxylate with a specific rotation of $[\alpha]_D^{20} = +52°\pm1.5°$ (c=1% in chloroform).

EXAMPLE 17

(2,3,4,5,6,-pentafluoro-phenyl)-methyl (1R, cis, ΔZ) 2,2-dimethyl-3-(3-methoxy-3-oxo-1-propenyl)-cyclopropane-carboxylate Using the procedure of Example 9, (1R, cis, ΔZ) 2,2-dimethyl-3-(3-methoxy-3-oxo-1-propenyl)-cyclopropane-carboxylic acid and (2,3,4,5,6-pentafluoro-phenyl)-methanol were reacted to obtain (2,3,4,5,6-pentafluoro-phenyl)methyl (1R, cis, ΔZ) 2,2-dimethyl-3-(3-methoxy-3-oxo-1-propenyl)-cyclopropane-carboxylate with a specific rotation of $[\alpha]_D^{20} = +29.5°\pm2°$ (c=0.8% in chloroform).

EXAMPLE 18

(RS) cyano (2,3,4,5,6-pentafluoro-phenyl)-methyl (1R, cis, ΔZ) 2,2-dimethyl-3-(3-methoxy-3-oxo-1-propenyl)-cyclopropane-carboxylate Using the procedure of Example 9, (1R, cis, ΔZ)-2,2-dimethyl-3-(3-methoxy-3-oxo-1-propenyl)-cyclopropane-carboxylic acid and (RS) cyano (2,3,4,5,6-pentafluoro-phenyl)methanol were reacted to obtain (RS) cyano (2,3,4,5,6-pentafluoro-phenyl)-methyl (1R, cis, ΔZ) 2,2-dimethyl-3-(3-methoxy-3-oxo-1-propenyl)-cyclopropane-carboxylate.

Analysis: $C_{18}H_{14}F_5NO_4$; molecular weight=403.31; Calculated: %C 53.61; %H 3.50; %N 3.47; %F 23.55; Found: 53.9; 3.5; 3.4; 23.7.

EXAMPLE 19

(RS) cyano 2-(6-phenoxy-pyridyl)-methyl (1R, cis, ΔZ) 2,2-dimethyl-3-(3-propoxy-3-oxo-1-propenyl)-cyclopropane-carboxylate Using the procedure of Example 9, (1R, cis, ΔZ) 2,2-dimethyl-3-(3-propoxy-3-oxo-1-propenyl)-cyclopropane-carboxylic acid and (RS) cyano 2-(6-phenoxy-pyridyl)-methanol were reacted to obtain (RS) cyano 2-(6-phenoxy-pyridyl)-methyl (1R, cis, ΔZ) 2,2-dimethyl-3-(3-propoxy-3-oxo-1-propenyl)-cyclopropane-carboxylate with a specific rotation of $[\alpha]_D^{20} = +55° \pm 2.5°$ (c=0.5% in chloroform).

EXAMPLE 20

Using the procedure of Example 9, (1R, cis, ΔZ) 2,2-dimethyl-3-(3-propoxy-3-oxo-1-propenyl)-cyclopropane-carboxylic acid and 1R-(3-phenoxy-phenyl)-ethanol were reacted to obtain 1R-(3-phenoxy-phenyl)-ethyl (1R, cis, ΔZ) 2,2-dimethyl-3-(3-propoxy-3-oxo-1-propenyl)-cyclopropane-carboxylate with a specific rotation of $[\alpha]_D^{20} = +123° \pm 2°$ (c=0.9% in chloroform).

EXAMPLE 21

Using the procedure of Example 9, (1R, cis, ΔZ) 2,2-dimethyl-3-(3-methoxy-3-oxo-1-propenyl)-cyclopropane-carboxylic acid and 1(R)-(3-phenoxy-phenyl)-2-propyn-1-yl alcohol were reacted to form 1(R) (3-phenoxy-phenyl)-2-propyn-1-yl (1R, cis, ΔZ) 2,2-dimethyl-3-(3-methoxy-3-oxo-1-propenyl)-cyclopropane-carboxylate with a specific rotation of $[\alpha]_D^{20} = +55.5° \pm 1.5°$ (c=1.0% in chloroform).

EXAMPLE 22

Using the procedure of Example 9, (1R, cis, ΔZ) 2,2-dimethyl-3-(3-isopropxy-3-oxo-1-propenyl)-cyclopropane-carboxylic acid and 1(R) (3-phenoxy-phenyl)-2-propyn-1-yl alcohol were reacted to obtain 1(R) (3-phenoxy-phenyl)-2-propyn-1-yl (1R, cis, ΔZ) 2,2-dimethyl-3-(3-isopropoxy-3-oxo-1-propenyl)-cyclopropane-carboxylate with a melting point of 66° C. and a specific rotation of $[\alpha]_D^{20} = +47° \pm 1°$ (c=1.2% in chloroform).

EXAMPLE 23

Using the procedure of Example 9, (1R, cis, ΔZ) 2,2-dimethyl-3-(3-propoxy-3-oxo-1-propenyl)-cyclopropane-carboxylic acid and 1R (3-phenoxy-phenyl)-2-propyn-1-yl alcohol were reacted to obtain 1R (3-phenoxy-phenyl)-2-propyn-1-yl (1R, cis, ΔZ) 2,2-dimethyl-3-(3-propoxy-3-oxo-1-propenyl)-cyclopropane-carboxylate with a specific roation of $[\alpha]_D^{20} = +48° \pm 2°$ (c=1% in chloroform).

EXAMPLE 24

Using the procedure of Example 9, (1R, cis, ΔZ) 2,2-dimethyl-3-(3-methoxy-3-oxo-1-propenyl)-cyclopropane-carboxylic acid and (4-benzoyl-phenyl)-methanol were reacted to obtain (4-benzoyl-phenyl)-methyl (1R, cis, ΔZ) 2,2-dimethyl-3-(3-methoxy-3-oxo-1-propenyl)-cyclopropane-carboxylate with a specific rotation of $[\alpha]_D^{20} = +46° \pm 2°$ (c=1% in chloroform).

EXAMPLE 25

(RS) cyano 2-(6-phenoxy-pyridyl)methyl (1R, cis, ΔZ) 2,2-dimethyl-3-(3-tert.-butoxy-3-oxo-1-propenyl)-cyclopropane-carboxylate STEP A: Methyl (1R, cis) 2,2-dimethyl-3-(3-hydroxy-3-oxo-1-propynyl)-cyclopropane-carboxylate 100 ml of a suspension of 20% butyllithium in cyclohexane were added at −70° C. to a mixture of 36.5 g of methyl (1R, cis) 2,2-dimethyl-3-(2,2-dibromoethenyl)-cyclopropane-carboxylate and 360 ml of tetrahydrofuran and the mixture was stirred for 10 minutes after which carbon dioxide was bubbled therethrough for 30 minutes. The temperature was allowed to rise to −20° C. and the mixture was poured into a mixture of ice, water and sodium bicarbonate. The mixture was extracted with ether and the organic phase was washed with water, dried and evaporated to dryness under reduced pressure. The residue was chromatographed over silica gel and was eluted with a 6-4 cyclohexane-ethyl acetate mixture containing 1% acetic acid to obtain 6.8 g of methyl (1R, cis) 2,2-dimethyl-3-(3-hydroxy-3-oxo-1-propynyl)-cyclopropane-carboxylate.

STEP B: Methyl (1R, cis) 2,2-dimethyl-3-(3-tert.-butoxy-3-oxo-1-propynyl)-cyclopropane-carboxylate 13.5 g of 0-tert.-butyl-N,N′-diisopropyl-urea were added at 15° C. to a mixture of 6.8 g of the product of Step A in 10 ml of ethyl acetate and the mixture was stirred for 2 hours and was filtered. The filtrate was evaporated to dryness and the residue was chromatographed over silica gel. Elution with an 85-15 cyclohexane-ethyl acetate mixture yielded 7 g of methyl (1R, cis) 2,2-dimethyl-3-(3-tert.-butoxy-3-oxo-1-propynyl-cyclopropane-carboxylate.

STEP C: Methyl (1R, cis, ΔZ) 2,2-dimethyl-3-(3-tert.-butoxy-3-oxo-1-propenyl)-cyclopropane-1-carboxylate A mixture of 7 g of the product of Step B, 149 ml of ethyl acetate, g of 10% palladium hydroxide on barium sulfate and 1.4 ml of quinoline was hydrogenated and was then filtered. The filtrate was washed with N hydrochloric acid, with water, was dried and evaporated to dryness under reduced pressure to obtain 5.8 g of methyl (1R, cis, ΔZ) 2,2-dimethyl-3-(3-tert.-butoxy-3-oxo-1-propenyl)-cyclopropane-1-carboxylate.

STEP D: (1R, cis, ΔZ) 2,2-dimethyl-3-(3-tert.-butoxy-3-oxo-1-propenyl)-cyclopropane-carboxylic acid A mixture of 2.5 g of the product of Step C, 25 ml of methanol and 9.8 ml of N aqueous sodium hydroxide solution was stirred at 50° C. for 3 hours and was then cooled to −75° C. and poured into water. The mixture was extracted with ether and the aqueous phase was acidified to a pH of 1 with hydrochloric acid. The mixture was extracted with ether and the organic phase was evaporated to dryness under reduced pressure. The residue was chromatographed over silica gel and was eluted with a 7-3 cyclohexane-ethyl acetate mixture containing 1% acetic acid to obtain 1.576 g of (1R, cis, ΔZ) 2,2-dimethyl-3-(3-tert.-butoxy-3-oxo-1-propenyl)-cyclopropane-carboxylic acid.

IR Spectrum ($CHCl_3$):

Absorption at 3500 $cm^{-1}$ (acid OH- monomer and dimer); at 1730 and 1695 $cm^{-1}$ (acid C═0 and ester); at 1628 $cm^{-1}$ (conjugated C═C); at 1390 and 1377 $cm^{-1}$ (geminal methyls); at 1368 $cm^{-1}$ (tert.-butyl).

STEP E: (RS) cyano 2-(6-phenoxy-pyridyl)-methyl (1R, cis, ΔZ) 2,2-dimethyl-3-(3-tert.-butoxy-3-oxo-1-propenyl)-cyclopropanecarboxylate Using the procedure of Example 9, the product of Step D and (RS) cyano 2-(6-phenoxy-pyridyl)-methanol were reacted to obtain (RS) cyano 2-(6-phenoxy-pyridyl)-methyl (1R, cis, ΔZ) 2,2-dimethyl-3-(3-tert.-butoxy-3-oxo-1-propenyl)-cyclopropane-carboxylate with a specific rotation of $[\alpha]_D^{20} = +68° \pm 1.5°$ (c=1% in chloroform).

EXAMPLE 26

Using the procedure of Example 9, (1R, cis, ΔZ) 2,2-dimethyl-3-(3-methoxy-3-oxo-1-propenyl)-cyclopropane-carboxylic acid and (RS) cyano-(4-benzoyl-phenyl)-methanol were reacted to obtain (RS) cyano (4-benzoyl-phenyl)-methyl (1R, cis, ΔZ) 2,2-dimethyl-3-(3-methoxy-3-oxo-1-propenyl)-cyclopropane-carboxylate.

Analysis: $C_{25}H_{23}O_5N$; molecular weight=417.466; Calculated: %C 71.93; %H 5.85; %N 3.35; Found: 71.9; 5.8; 3.2.

EXAMPLE 27

Using the procedure of Example 9, (1R, cis, ΔZ) 2,2-dimethyl-3-(3-tert.-butoxy-3-oxo-1-propenyl)-cyclopropane-carboxylic acid and (3-propyn-2-yl-2,5-dioxo-imidazolidinyl)methanol were reacted to obtain (3-propyn-2-yl-2,5-dioxoimidazolidinyl)-methyl (1R, cis, ΔZ) 2,2-dimethyl-3-(3-tert.-butoxy-3-oxo-1-propenyl)-cyclopropane-carboxylate with a specific rotation of $[\alpha]_D^{20} = +31° \pm 2°$ (c=0.5% in chloroform).

EXAMPLE 28

Using the procedure of Example 9, (1R, cis, ΔZ) 2,2-dimethyl-3-(3-isopropoxy-3-oxo-1-propenyl)-cyclopropane-carboxylic acid and (3-propyn-2-yl-2,5-dioxoimidazolidinyl)methanol were reacted to obtain (3-propyn-2-yl-2,5-dioxoimidazolidinyl)-methyl (1R, cis, ΔZ) 2,2-dimethyl-3-(3-isopropoxy-3-oxo-1-propenyl)-cyclopropane-carboxylate melting at 78° C. and having a specific rotation of $[\alpha]_D^{20} = +15.5° \pm 1°$ (c=1% in chloroform).

EXAMPLE 29

(3-propyn-2-yl)-2,5-dioxo-imidazolidinyl)-methyl (1R, cis, ΔZ)
2,2-dimethyl-3-(3-cyclobutoxy-3-oxo-1-propenyl)-cyclopropane-carboxylate STEP A: Tert.-butyl (1R, cis, ΔZ) 2,2-dimethyl-3-(3-cyclo-butoxy-3-oxo-1-propenyl)-cyclopropane-carboxylate A solution of 3.45 g of dichlorohexycarbodiimide and 28 mg 4-dimethylamino-pyridine in 20 ml of methylene chloride were added at 0° to 5° C. to a solution of 1.7 mg of cyclobutanol, 4 g of tert.-butyl (1R, cis Z) 2,2-dimethyl-3-(3-hydroxy-3-oxo-1-propenyl)-cyclopropane-carboxylate and 20 ml of methylene chloride and the mixture was stirred for 2 hours at 5° C. and 2 hours at room temperature. The mixture was filtered and the filtrate was evaporated to dryness. The residue was chromatographed over silica gel and was eluted with a 9-1 n-hexane-isopropyl ether mixture to obtain 2.3 g of tert.-butyl (1R, cis, ΔZ) 2,2-dimethyl-3-(3-cyclobutoxy-3-oxo-1-propenyl)-cyclopropane-carboxylate.

STEP B: (1R, cis, ΔZ) 2,2-dimethyl-3-(3-cyclobutoxy-3-oxo-1-propenyl)-cyclopropane-carboxylic acid A mixture of 2.3 g of the product of Step A, 25 ml of toluene and 250 mg of p-toluene sulfonic acid was refluxed for 15 minutes and was cooled. The mixture was stirred for 2 hours at 0° to 5° C. and was filtered. The filtrate was evaporated to dryness under reduced pressure to obtain 1.8 g of (1R, cis, ΔZ) 2,2-dimethyl-3-(3-cyclobutoxy-3-oxo-1-propenyl)-cyclopropane-carboxylic acid.

IR Spectrum (chloroform):

Absorptions at 3500 cm$^{-1}$ (acid OH); at 1733 cm$^{-1}$ (acid C=O); at 1702 cm$^{-1}$ (ester); at 1390 and 1390 cm$^{-1}$ (geminal dimethyls).

STEP C: (3-propyn-2-yl-2,5-dioxo-imidazolidinyl)-methyl (1R, cis, ΔZ) 2,2-dimethyl-3-(3-cycylobutoxy-3-oxo-1-propenyl)-cyclopropane-carboxylate Using the procedure of Example 9, (1R, cis, ΔZ) 2,2-dimethyl-3-(3-cyclobutoxy-3-oxo-1-propenyl)-cyclopropane-carboxylic acid and (3-propyn-2-yl-2,5-dioxo-imidazolidinyl)-methanol were reacted to obtain (3-propyn-2-yl-2,5-dioxo-imidazolidinyl)-methyl (1R, cis, ΔZ) 2,2-dimethyl-3-(3-cyclobutoxy-3-oxo-1-propenyl)-cyclopropane-carboxylate with a specific rotation of $[\alpha]_D^{20} = +18° \pm 1°$ (c=1.2% in chloroform).

EXAMPLE 30

(3-propyn-2-yl-2,5-dioxo-imidazolidinyl)-methyl (1R, cis, ΔZ)
2,2-dimethyl-3-(3-isobutoxy-3-oxo-1-propenyl)-cyclopropane-carboxylate STEP A: Terbutyl (1R, cis ΔZ) 2,2-dimethyl 3-/3-hydroxy 3-oxo 1-propenyl/cyclopropane carboxylate.

2 g of tertbutyl (1R cis) 2,2-dimethyl 3[3-hydroxy-3-oxo 1-propynyl] cyclopropane carboxylate in 40 cm³ of ethyl acetate are hydrogenated in the presence of 0.38 g of 10% palladium hydroxide on barium sulphate and 0.4 cm³ of quinoline. The whole is filtered, the filtrate is washed with 0.5N hydrochloric acid then with water until neutral, dried and concentrated to dryness under reduced pressure and 2 g of the product sought are obtained, melting at 94° C.

STEP B: Terbutyl (1R cis ΔZ) 2,2-dimethyl 3-(3-isobutoxy-3-oxo-1-propenyl) cyclopropane-1-carboxylate.

Into 10 cm3 of methylene chloride and 1 g of isobutanol are introduced 4 g of tertbutyl (1R, cis, ΔZ) 2,2-dimethyl 3-(3-hydroxy 3-oxo 1-propenyl) cyclopropane-1-carboxylate, prepared according to preparation 4 Stage A, then, at 0° C., 2.8 g of dicyclohexylcarbodiimide and 30 mg of dimethylaminopyridine in solution in 10 cm3 of methylene chloride are added, the whole is agitated for 17 hours at 60° C., the insoluble matter is eliminated by filtration, the filtrate is concentrated to dryness for distillation under reduced pressure, the residue is chromatographed on silica eluting with a mixture of cyclohexane and isopropyl ether (9:1) and 2.1 g of tertbutyl (1R cis, ΔZ) 2,2-dimethyl 3-(3-isobutoxy 3-oxo 1-propenyl) cyclopropane-1-carboxylate are obtained.

STEP C: (1R cis, ΔZ) 2,2-dimethyl 3-(3-isobutoxy 3-oxo-1-propenyl) cyclopropane-1-carboxylic acid.

Into 20 cm3 of toluene are introduced 2.1 g of tertbutyl (1R cis, ΔZ) 2,2-dimethyl 3-(3-isobutoxy 3-oxo 1-propenyl) cyclopropane-1-carboxylate and 0.1 g of paratoluene sulphonic acid, the whole is taken to reflux and maintained there for 20 minutes, concentrated to dryness by distillation under reduced pressure and chromatographed on silica eluting with a mixture of hexane and ethyl acetate (7:3) containing 1% of acetic acid and 1.53 g of (1R cis, ΔZ) 2,2-dimethyl 3-(3-isobutoxy 3-oxo-1-propenyl) cyclopropane-1-carboxylic acid are obtained.

IR Spectrum (CHCL₃): Absorption at 3300 cm⁻¹, attributed to the acid OH; Absorption at 1730 cm⁻¹, 1706 cm⁻¹, 1694 cm⁻¹ attributed to the acid C=O and conjugated ester; Absorption at 1630 cm⁻¹ attributed to C=C (ΔZ); Absorption at 1390 cm⁻¹, 1380 cm⁻¹ attributed to the geminal methyls.

STEP D: (3-propyn-2-yl-2,5-dioxo-imidazolidinyl)-methyl (1R, cis, ΔZ) 2,2-dimethyl-3-(3-isobutoxy-3-oxo-1-propenyl)-cyclopropane-carboxylate Using the procedure of Example 9, the product of Step C and (3-propyn-2-yl-2,5-dioxo-imidazolidinyl)-methanol were reacted to obtain (3-propyn-2-yl-2,5-dioxo-imidazolidinyl)-methyl (1R, cis, ΔZ) 2,2-dimethyl-3-(3-isobutoxy-3-oxo-1-propenyl)-cyclopropane-carboxylate with a specific rotation of $[\alpha]_D^{20} = +20.5° \pm 1.5°$ (c=1% in chloroform).

EXAMPLE 31

Using the procedure of Example 9, (1R, cis, ΔZ) 2,2-dimethyl-3-(3-ethoxy-3-oxo-1-propenyl)-cyclopropane-carboxylic acid and (3d-propyn-2-yl-2,5-dioxo-imidazolidinyl)-methanol were reacted to obtain (3-propyn-2-yl-2,5-dioxo-imidazolidinyl)-methyl (1R, cis, ΔZ) 2,2-dimethyl-3-(3-ethoxy-3-oxo-1-propenyl)-cyclopropane-carboxylate with a specific rotation of $[\alpha]_D^{20} = +10° \pm 4°$ (c=0.2% in CHCl₃).

EXAMPLE 32

Using the procedure of Example 9, (1R, cis, ΔZ) 2,2-dimethyl-3-(3-ethoxy-3-oxo-1-propenyl)-cycloproane-1-carboxylic acid and 1(R)-(3-phenoxy-phenyl)-2-propyn-1-yl alcohol were reacted to obtain 1(R) (3-phenoxy-phenyl)-2-propyn-1-yl (1R, cis, ΔZ) 2,2-dimethyl-3-(3-ethoxy-3-oxo-1-propenyl)-cyclopropane-carboxylate with a specific rotation of $[\alpha]_D^{20} = +48.5° \pm 2°$ (c=1% in chloroform).

EXAMPLE 33

Using the procedure of Example 9, (1R, cis, ΔZ) 2,2-dimethyl-3-(3-isopropoxy-3-oxo-1-propenyl)-cyclopropane-carboxylic acid and 5-benzyl-3-furyl-methanol was reacted to obtain 5-benzyl-3-furyl-methyl (1R, cis, ΔZ) 2,2-dimethyl-3-(3-isopropoxy-3-oxo-1-propenyl)-cyclopropane-carboxylate with a specific rotation of $[\alpha]_D^{20} = +44° \pm 2°$ (c=0.4% in chloroform).

EXAMPLE 34

Using the procedure of Example 9, (1R, cis, ΔZ) 2,2-dimethyl-3-(3-isopropoxy-3-oxo-1-propenyl)-cyclopropane-carboxylic acid and m-phenoxy-benzyl alcohol were reacted to obtain m-phenoxy-benzyl (1R, cis, ΔZ) 2,2-dimethyl-3-(3-isopropoxy-3-oxo-1-propenyl)-cyclopropane-carboxylate with a specific rotation of $[\alpha]_D^{20} = +42°$ C. $\pm 2°$ (c=0.5% in chloroform).

EXAMPLE 35

(RS) cyano 2-(6-phenoxy-pyridyl)-methyl (1R, cis ΔZ) 2,2-dimethyl-3-(3-cyclopropylmethoxy-3-oxo-1-propenyl)-cyclopropane-carboxylate STEP A: Tert.-butyl (1R, cis, ΔZ) 2,2-dimethyl-3-(3-cyclopropylmethoxy-3-oxo-1-propenyl)-cyclopropane-carboxylate 2 g of 4-dimethylamino-pyridine and a solution of 17.5 g of dicyclohexylcarbodiimide in 60 ml of methylene chloride were added to a mixture of 20 g of tert.-butyl (1R, cis, ΔZ) 2,2-dimethyl-3-(3-hydroxy-3-oxo-1-propenyl)-cyclopropane-carboxylate, 6.2 g of cyclopropyl carbinol and 150 ml of methylene chloride and the mixture was stirred for 2 hours at 20° C. and was filtered. The filtrate was evaporated to dryness under reduced pressure and the residue was chromatographed over silica gel. Elution with a 9-1 n-hexane-isopropyl ether mixture yielded 12.32 g of tert.-butyl (1R, cis ΔZ) 2,2-dimethyl-3-(3-cyclopropylmethoxy-3-oxo-1-propenyl)-cyclopropane-carboxylate.

STEP B: (1R, cis, ΔZ) 2,2-dimethyl-3-(3-cyclopropylmethoxy-3-oxo-1-propenyl)-cyclopropane-carboxylic acid A mixture of 12.32 g of the product of Step A, 0.6 g of p-toluene sulfonic acid and 120 ml of toluene was refluxed for 45 minutes and was cooled and evaporated to dryness under reduced pressure. The residue was chromatographed over silica gel and was eluted with a 7-3 n-hexane-ethyl acetate mixture containing 1% o acetic acid to obtain 8.94 g of (1R, cis, ΔZ) 2,2-dimethyl-3-(3-cyclopropylmethoxy-3-oxo-1-propenyl) cyclopropane-carboxylic acid melting at 106° C.

NMR Spectrum (deuterochloroform): Peaks at 1.29–1.31 ppm (hydrogens of geminal methyls); at 1.13 ppm (hydrogen of —CH); at 1.85–2 ppm (1-hydrogens of cyclomethyl); at 3.9–4 ppm (hydrogen of

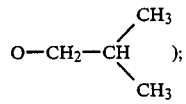

at 5.82–6.01 ppm and 6.42 to 6.77 ppm (hydrogens of cis ethylenic chain).

STEP C: (RS) cyano-2-(6-phenoxy-pyridyl)-methyl (1R, cis ΔZ) 2,2-dimethyl-3-(3-cyclopropyl-3-oxo-1-propenyl)-cyclopropane-carboxylate Using the procedure of Example 9, the acid of Step B and (RS) cyano-2-(6-phenoxy-pyridyl)-methanol were reacted to obtain (RS) cyano-2-(6-phenoxy-pyridyl)-methyl (1R, cis ΔZ) 2,2-dimethyl-3-(3-cyclopropyl-3-oxo-1-propenyl)-cyclopropanecarboxylate with a specific rotation of $[\alpha]_D^{20} = +53° \pm 2°$ (c=0.5% in chloroform).

EXAMPLE 36

Using the procedure of Example 9, (1R, cis, ΔZ) 2,2-dimethyl-3-(3-n-propoxy-3-oxo-1-propenyl)-cyclopropane-carboxylic acid and 5-benzyl-3-furyl-methanol were reacted to obtain 5-benzyl-3-furyl-methyl (1R, cis, ΔZ) 2,2-dimethyl-3-(3-n-propoxy-3-oxo-1-propenyl) cyclopropane-carboxylate with a specific rotation of $[\alpha]_D^{20} + 41° \pm 2°$ (c=0.5% in chloroform).

EXAMPLE 37

Using the procedure of Example 9, (1R, cis, ΔZ) 2,2-dimethyl-3-(3-isopropoxy-3-oxo-1-propenyl)-cyclopropane-carboxylic acid and (1,3,4,5,6,7-hexahydro-1,3-dioxo-2H-isoindol-2-yl)-methanol were reacted to obtain (1,3,4,5,6,7-hexahydro-1,3-dioxo-2H-isoindol-2-yl)-methyl (1R, cis, ΔZ) 2,2-dimethyl-3-(3-isopropoxy-3-oxo-1-propenyl)-cyclopropane-carboxylate with a melting point of 94° C. and a specific rotation of $[\alpha]_D^{20} = -22.5° \pm 2°$ (c=0.5% in CHCl₃).

EXAMPLE 38

Using the procedure of Example 9, (1R, cis, ΔZ) 2,2-dimethyl-3-(3-n-propoxy-3-oxo-1-propenyl)-cyclopropane-carboxylic acid and (1,3,4,5,6,7-hexahydro-1,3-dioxo-2H-isoindol-2-yl)-methanol were reacted to obtain (1,3,4,5,6,7-hexahydro-1,3-dioxo-2H-isoindol-2-yl)-methyl (1R, cis ΔZ) 2,2-dimethyl-3-(3-n-propoxy-3-oxo-1-propenyl)-cyclopropane-carboxylate with a melting point of 76° C. and a specific rotation of $[\alpha]_D^{20} = -15°$ (c=0.15%) in carbon tetrachloride).

EXAMPLE 39

Using the procedure of Example 9, m-phenoxy-benzyl alcohol and (1R, cis, ΔZ) 2,2-dimethyl-3-(3-n-propoxy-3-oxo-1-propenyl)-cyclopropane-carboxylic acid were reacted to obtain m-phenoxy-benzyl (1R, cis, ΔZ) 2,2-dimethyl-3-(3-n-propoxy-3-oxo-1-propenyl)-cyclopropane-carboxylate with a specific rotation of $[\alpha]_D^{20} = +40° \pm 2°$ (c=0.5% in chloroform).

EXAMPLE 40

Using the procedure of Example 9, m-phenoxy-benzyl alcohol and (1R, cis, ΔZ) 2,2-dimethyl-3-(3-cyclopropylmethoxy-3-oxo-1-propenyl)-cyclopropane-carboxylic acid were reacted to obtain m-phenoxy-benzyl (1R, cis, ΔZ) 2,2-dimethyl-3-(3-cyclopropylmethoxy-3-oxo-1-propenyl)-cyclopropane-carboxylate with a specific rotation of $[\alpha]_D^{20} = +46.5° \pm 2°$ (c=0.6% in chloroform).

EXAMPLE 41

Using the procedure of Example 9, (1R cis ΔZ) 2,2-dimethyl-3-(3-cyclobutoxy-3-oxo-1-propenyl)-cyclopropane-carboxylic acid and 1(R)-(3-phenoxy-phenyl)-ethanol were reacted to obtain 1(R)-(3-phenoxy-phenyl)-ethyl (1R, cis, ΔZ) 2,2-dimethyl-3-(3-cyclobutoxy-3-oxo-1-propenyl)-cyclopropane-carboxylate with a specific rotation of $[\alpha]_D^{20} = +125.5° \pm 2°$ (c=1% in chloroform).

EXAMPLE 42

Using the procedure of Example 9, (1R, cis, ΔZ) 2,2-dimethyl-3-(3-cycloproplymethoxy-3-oxo-propenyl)-cyclopropane-carboxylic acid and (1,3,4,5,6,7-hexahydro-1,3-dioxo-2H-isoindol-2-yl) methanol were reacted to obtain (1,3,4,5,6,7-hexahydro-1,3-dioxo-2H-isoindol-2-yl)-methyl (1R, cis, ΔZ) 2,2-dimethyl-3-(3-cyclopropylmethoxy-3-oxo-1-propenyl)-cyclopropane-carboxylate with a melting point of 102° C. and a specific rotation of $[\alpha]_D^{20} = +6.5° \pm 2°$ (c=0.3% in chloroform).

EXAMPLE 43

Using the procedure of Example 9, (1R, cis, ΔZ) 2,2-dimethyl-3-(3-cyclopropylmethoxy-3-oxo-1-propenyl)-cyclopropane-carboxylic acid and 5 benzyl-3-furyl-methanol were reacted to obtain 5-benzyl-3-furyl-methyl (1R, cis, ΔZ) 2,2-dimethyl-3-(3-cyclopropylmethoxy-3-oxo-1-propenyl)-cyclopropane-carboxylate with a specific rotation of $[\alpha]_D^{20} = +42° \pm 2°$ (c=0.7% in chloroform).

EXAMPLE 44

Using the procedure of Example 9, (1R, cis, ΔZ) 2,2-dimethyl-3-(3-cyclopropylmethoxy-3-oxo-1-propenyl)-cyclopropane-carboxylic acid and (S) 2-methyl-4-oxo-3-(2-propenyl)-2-cyclopentenyl alcohol were reacted to obtain (S) 2-methyl-4-oxo-3-(2-propenyl)-2-cyclopentenyl (1R, cis ΔZ) 2,2-dimethyl-3-(3-cyclopropylmethoxy-3-oxo-1-propenyl) cyclopropane carboxylate with a specific rotation of $[\alpha]_D^{20} = +64.5° \pm 2.5°$ (c=1% in chloroform).

EXAMPLE 45

(3-propyn-2-yl-2,5-dioxo-imidazolidinyl)-methyl (1R, cis, ΔZ) 2,2-dimethyl-3-(3-cyclopentyloxy-3-oxo-1-propenyl)-cyclopropane-carboxylate STEP A: Tert.-butyl (1R, cis, ΔZ) 2,2-dimethyl-3-(3-cyclopentyloxy-3-oxo-1-propenyl)-cyclopropane-carboxylate A solution of 3.43 g of dicyclohexylcarbodiimide, 40 mg of 4-dimethyl-pyridine and 10 ml of methylene chloride were added at 0° C. to a mixture of 4 g of tert.-butyl (1R, cis, ΔZ) 2,2-dimethyl-3-(3-hydroxy-3-oxo-1-propenyl)-cyclopropane-carboxylate, 1.43 g of cyclopentanol and 15 ml of methylene chloride and the mixture was stirred at 20° C. for 17 hours and was then filtered. The filtrate was evaporated to dryness under reduced pressure and the residue was chromatographed over silica gel. Elution with a 9-1 cyclohexane-isopropyl ether mixture yielded 1.38 g of tert.-butyl (1R, cis, ΔZ) 2,2-dimethyl-3-(3-cyclopentyloxy-3-oxo-1-propenyl)cyclopropane-carboxylate melting at 57° C.

STEP B: (1R, cis, ΔZ) 2,2-dimethyl-3-(3-cyclopentyloxy-3-oxo-1-propenyl)-cyclopropane-carboxylic acid A mixture of 2.54 g of the product of Step A, 0.1 g of p-toluene sulfonic acid and 25 ml of toluene was refluxed for 20 minutes and was then evaporated to dryness under reduced pressure. The residue was chromatographed over silica gel and was eluted with a 7-3 n-hexane-ethyl acetate mixture containing 1% of acetic acid to obtain 1.82 g of (1R, cis ΔZ) 2,2-dimethyl-3-(3-cyclopentyloxy-3-oxo-1-propenyl)-cyclopropane-carboxylic acid.

IR Spectrum (CHCl₃): Absorption at 3510 cm⁻¹ (acid —OH); at 1735 and 1702 cm⁻¹ (acid C═O and conjugated ester); at 1632 cm⁻¹ (conjugated C═C); at 1380 cm⁻¹ (geminal methyls).

STEP C: (3-propyn-2-yl-2,5-dioxo-imidazolidinyl)-methyl (1R, cis, ΔZ) 2,2-dimethyl-3-(3-cyclopentyloxy-3-oxo-1-propenyl)-cyclopropane-carboxylate Using the procedure of Example 9, the product of Step B and (3-propyn-2-yl-2,5-dioxo-imidazolidinyl)-methanol were reacted to obtain (3-propyn-2-yl-2,5-dioxo-imidazolidinyl)-methyl (1R, cis, ΔZ) 2,2-dimethyl-3-(3-cyclopentyloxy-3-oxo-1-propenyl)-cyclopropane-carboxylate with a specific rotation of $[\alpha]_D^{20} = +15.5° \pm 1.5°$ (c=1% in chloroform).

EXAMPLE 46

Using the procedure of Example 9, (1R, cis, ΔZ) 2,2-dimethyl-3-(3-cyclopentyloxy-3-oxo-1-propenyl)-cyclopropane-carboxylic acid and (RS) cyano-2-(6-phenoxy-6-pyridinyl)-methanol were reacted to obtain (RS) cyano-2-(6-phenoxy-6-pyridinyl)-methyl (1R, cis, ΔZ) 2,2-dimethyl-3-(3-cyclopentyloxy-3-oxo-1-propenyl)-cyclopropane-carboxylate with a specific rotation of $[\alpha]_D^{20} = +42° \pm 1°$ (c=0.9% in benzene).

EXAMPLE 47

Using the procedure of Example 9, (1R, cis, ΔZ) 2,2-dimethyl-3-(3-methoxy-3-oxo-1-propenyl)-cyclopropane-carboxylic acid and (3-propyn-2-yl-2,5-dioxo-imidazolidinyl)-methanol were reacted to obtain (3-propyn-2-yl-2,5-dioxo-imidazolidinyl)-methyl (1R, cis, ΔZ) 2,2-dimethyl-3-(3-methoxy-3-oxo-1-propenyl)-cyclopropane-carboxylate with a specific rotation of $[\alpha]_D^{20} \simeq +1°$ (c=0.5% in benzene).

EXAMPLE 48

Using the procedure of Example 9, (1R, cis, ΔZ) 2,2-dimethyl-3-(3-sec-butoxy-3-oxo-1-propenyl)-cyclopropane-carboxylic acid and (3-propyn-2-yl-2,5-dioxo-imidazolidinyl)-methanol were reacted to obtain (3-propyn-2-yl-2,5-dioxo-imidazolidinyl)-methyl (1R, cis, ΔZ) 2,2-dimethyl-3-(3-sec-butoxy-3-oxo-1-propenyl)-cyclopropane-carboxylate with a specific rotation of $[\alpha]_D^{20} = +16.5° \pm 1°$ (c=0.8% in chloroform).

EXAMPLE 49

Using the procedure of Example 9, (1R, cis, ΔZ) 2,2-dimethyl-3-(3-methoxy-3-oxo-1-propenyl)-cyclopropane-carboxylic acid and (S) cyano-(3-phenoxy-4-fluoro-phenyl)-methanol were reacted to obtain (S) cyano-(3-phenoxy-4-fluoro-phenyl)-methyl (1R, cis, ΔZ) 2,2-dimethyl-3-(3-methoxy-3-oxo-1-propenyl)-cyclopropane-carboxylate with a specific rotation of $[\alpha]_D^{20} = +56.5° \pm 2.5°$ (c=0.5% in benzene).

EXAMPLE 50

Using the procedure of Example 9, (1R, cis, ΔZ) 2,2-dimethyl-3-(3-methoxy-3-oxo-1-propenyl)-cyclopropane-carboxylic acid and (R, S) 1-(4-fluoro-3-phenoxy-phenyl)-2-propyn-2-yl alcohol were reacted to obtain (R, S) 1-(4-fluoro-3-phenoxy-phenyl)-2-propyn-1-yl (1R, cis, ΔZ) 2,2-dimethyl-3-(3-methoxy-3-oxo-1-propenyl)-cyclopropane-carboxylate.

NMR Spectrum (deuterochloroform): Peaks at 1.22 to 1.32 ppm (hydrogens of geminal methyls); at 1.09–2.05 ppm and 3.1 to 3.43 ppm (1- and 3-hydrogens of cyclopropyl); at 2.62 to 2.66 ppm (hydrogen of =CH—); at 3.72–3.73 ppm (hydrogens of —CO$_2$CH$_2$—); at 5.8 to 6 ppm (ethylenic hydrogen of ester side chain); at 6.38 to 6.83 ppm (ethylenic hydrogen of side chain and hydrogen of COOCH$_2$—); at 6.9 to 7.55 ppm (aromatic hydrogens).

EXAMPLE 51

Using the procedure of Example 9, (1R, cis, ΔZ) 2,2-dimethyl-3-(3-tert.-butoxy-3-oxo-1-propenyl)-cyclopropane-carboxylic acid and (RS) 1-(4-fluoro-3-phenoxy)-2-propyn-1-yl alcohol were reacted to obtain (R, S) 1-(4-fluoro-3-phenoxy-phenyl)-2-propyn-1-yl (1R, cis, ΔZ) 2,2-dimethyl-3-(3-tert.-butoxy-3-oxo-1-propenyl)-cyclopropane-carboxylate.

NMR Spectrum (deuterochloroform): Peaks at 1.22 to 1.31 ppm (hydrogens of geminal methyls); at 1.47–1.5 ppm (hydrogens of tert.-butyl); at 1.87–2.01 ppm and 3.12 to 3.43 ppm (1- and 3-hydrogens of cyclopropyl); at 2.6 to 2.65 ppm (hydrogen of =CH—); at 5.7–5.9 ppm (ethylenic hydrogen of ester side chain); at 6.28 to 6.72 ppm (ethylenic hydrogen of side chain and hydrogen of

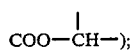

at 6.91 to 7.55 ppm (aromatic hydrogens).

EXAMPLE 52

Using the procedure of Example 9, (1R, cis, ΔZ) 2,2-dimethyl-3-(3-methoxy-3-oxo-1-propenyl)-cyclopropane-carboxylic acid and (R, S) 1-(6-phenoxy-2-pyridinyl)-2-propyn-1-yl alcohol were reacted to obtain (R, S) 1-(6-phenoxy-2-pyridinyl)-2-propyn-1-yl (1R, cis, ΔZ) 2,2-dimethyl-3-(3-methoxy-3-oxo-1-propenyl)-cyclopropane-carboxylate.

NMR Spectrum (deuterochloroform): Peaks at 1.23 to 1.31 ppm (geminal methyls); at 1.96–2.1 ppm and 3.13 to 3.47 ppm (1- and 3-hydrogens of cyclopropyl); at 2.59 to 2.63 ppm (hydrogen of =CH—); at 3.73 ppm (hydrogens of —COOCH$_3$); at 5.78 to 6.02 ppm (ethylenic hydrogen of ester side chain); at 6.3–6.34 ppm (hydrogen of —COOCH—); at 6.43 to 6.88 ppm (ethylenic hydrogen of side chain); at 6.75 to 7.9 ppm (aromatic hydrogens).

EXAMPLE 53

Using the procedure of Example 9, (1R, cis, ΔZ) 2,2-dimethyl-3-(3-tert.-butoxy-3-oxo-1-propenyl)-cyclopropane-carboxylic acid and (R, S) 1-(6-phenoxy-2-pyridinyl)-2-propyn-1-yl alcohol were reacted to obtain (R, S) 1-(6-phenoxy-2-pyridinyl)-2-propyn-1-yl (1R, cis, ΔZ) 2,2-dimethyl-3-(3-tert.-butoxy-3-oxo-1-propenyl)-cyclopropane-carboxylate.

NMR Spectrum (deuterochloroform): Peaks at 1.24 to 1.32 ppm (hydrogens of geminal methyls); at 1.5 ppm (hydrogens of tert.-butyl); at 1.93–2.07 ppm and 3.13 to 3.46 ppm (1- and 3-hydrogens of cyclopropyl); at 2.59 to 2.63 ppm (hydrogen of CHCH); at 5.68 to 5.90 ppm (ethylenic hydrogen of ester side chain); at 6.3–6.34 ppm (hydrogen of

at 6.47 to 6.86 ppm (ethylenic hydrogen of side chain); at 6.75 to 7.9 ppm (aromatic hydrogens).

EXAMPLE 54

Using the procedure of Example 9, (1R, cis, ΔZ) 2,2-dimethyl-3-(3-tert.-butoxy-3-oxo-1-propenyl)-cyclopropane-carboxylic acid and benzyl alcohol were reacted to obtain benzyl (1R, cis ΔZ) 2,2-dimethyl-3-(3-tert.butoxy-3-oxo-1-propenyl)-cyclopropane-carboxylate.

NMR Spectrum (deuterochloroform):

Peaks at 1.28 to 1.32 ppm (hydrogens of geminal methyls); at 1.5 ppm (hydrogens of tert.-butyl); at 1.9–2.04 ppm and 3.08 to 3.41 ppm (1- and 3-hydrogens of cyclopropyl); at 5.15 ppm (hydrogens of —COOCH$_2$—φ); at 5.72–5.92 ppm (ethylenic hydrogen of ester side chain); at 6.38 to 6.75 ppm (ethylenic hydrogen of side chain); at 7.4 ppm (aromatic hydrogens).

EXAMPLE 55

Using the procedure of Example 9, (1R, cis, ΔZ) 2,2-dimethyl-3-(3-tert.-butoxy-3-oxo-1-propenyl)-cyclopropane-carboxylic acid and (6-phenoxy-2-pyridinyl)-methanol were reacted to obtain (6-phenoxy-2-pyridinyl)-methyl (1R, cis ΔZ) 2,2-dimethyl-3-(3-tert.-butoxy-3-oxo-1 propenyl)-cyclopropane-carboxylate.

NMR Spectrum (deuterochloroform): Peaks at 1.3–1.32 ppm (hydrogens of geminal methyls); at 1.51 ppm (hydrogens of tert.-butyl); at 1.96–2.11 ppm and 3.13 to 3.47 ppm (1- and 3-hydrogens of cyclopropyl); at 5.13 ppm (hyrogens of —COOCH₂—); at 5.73–5.92 ppm (ethylenic hydrogen of ester side chain); at 6.37 to 6.73 ppm (ethylenic hydrogen of side chain); at 7.58–7.72–7.85 ppm (hydrogens of pyridyl).

EXAMPLE 56 using the procedure of Example 9, (1R, cis, ΔZ) 2,2-dimethyl-3-(3-methoxy-3-oxo-1-propenyl)-cyclopropane-carboxylic acid and (6-phenoxy-2-pyridinyl)-methanol were reacted to obtain (6-phenoxy-2-pyridinyl)-methyl (1R, cis, ΔZ) 2,2-dimethyl-3-(3-methoxy-3-oxo-1-propenyl)-cyclopropane-carboxylate.

NMR Spectrum (deuterochloroform): Peaks at 1.3 ppm (hydrogens of geminal methyls); at 1.98–2.13 ppm and 3.13 to 3.45 ppm (1- and 3-hydrogens of cyclopropyl); at 3.74 ppm (hydrogens of —COOCH₃—); at 5.12 ppm (hydrogens of —COOCH₂—); at 5.82–6.02 ppm and 6.5 to 6.87 ppm (ethylenic hydrogens); at 7 to 7.85 ppm (aromatic hydrogens).

EXAMPLE 57

Using the procedure of Example 9, (1R, cis, ΔZ) 2,2-dimethyl-3-(3-tert.-butoxy-3-oxo-1propenyl)-cyclopropane-carboxylic acid and (R,S) 1-(6-phenoxy-2-pyridinyl)-ethanol were reacted to obtain (R,S) 1-(6-phenoxy-2-pyridinyl)-ethyl (1R, cis, ΔZ) 2,2-dimethyl-3-(3-tert.-butoxy-3-oxo-1-propenyl)cyclopropane-carboxylate.

NMR Spectrum (deuterochloroform: Peaks at 1.25 to 1.32 ppm (hydrogens of geminal methyls); at 1.47–1.57 ppm (hydrogens of

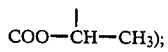

at 1.5 ppm (hydrogens of tert.-butyl); at 1.95–2.09 ppm and 3.12 to 3.43 ppm (1- and 3-hydrogens of cyclopropyl); at 5.67 to 5.92 ppm and 6.32 to 6.75 ppm (ethylenic hydrogens); at 6.67 to 7.5 ppm (aromatic hydrogens); at 7.55 to 7.83 ppm (hydrogens of pyridyl); at 5.63 to 5.97 ppm (hydrogen of

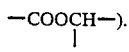

EXAMPLE 58

Using the procedure of Example 9, (1R, cis, ΔZ) 2,2-dimethyl-3-(3-methoxy-3-oxo-1-propenyl)-cyclopropane-carboxylic acid and (R,S) 1-(6-phenoxy-2-pyridinyl)-ethanol were reacted to obtain (R,S) 1-(6-phenoxy-2-pyridinyl)-ethyl (1R, cis, ΔZ) 2,2-dimethyl-3-(3-methoxy-3-oxo-1-propenyl)-cyclopropane-carboxylate.

NMR Spectrum (deuterochloroform): Peaks at 1.25 to 1.3 ppm (hydrogens of geminal methyls); at 1.43 to 1.57 ppm (hydrogens of —COOCH—CH₃); at 1.97–2.11 ppm and 3.1 to 3.42 ppm (1- and 3-hydrogens of cyclopropyl); at 5.63 to 6.08 ppm (hydrogens of —COOCH₂); at 5.78 to 6.02 ppm and 6.45 to 6.87 ppm (ethylenic hydrogens); at 6.67 to 6.8 and 7 to 7.67 ppm (aromatic hydrogens); at 7.55 to 7.83 ppm (hydrogens of pyridyl).

EXAMPLE 59

Using the procedure of Example 9, (1R, cis, ΔZ) 2,2-dimethyl-3-(3-tert.-butoxy-3-oxo-1-propenyl)-cyclopropane-carboxylic acid and 3-(phenyl carbonyl) benzyl alcohol were reacted to obtain 3-(phenylcarbonyl)-benzyl (1R, cis, ΔZ) 2,2-dimethyl-3-(3-tert.-butoxy-3-oxo-1-propenyl)-cyclopropane-carboxylate.

Analysis: $C_{27}H_{30}O_5$; molecular weight =434.537; Calculated: %C 74.63; %H 6.96; Found: 74.60; 7.00.

EXAMPLE 60

Using the procedure of Example 9, (1R, cis, ΔZ) 2,2-dimethyl-3-(3-tert.-butoxy-3-oxo-1-propenyl)-cyclopropane-carboxylic acid and 1R (3-phenoxyphenyl)-2-propyn-1-yl alcohol were reacted to obtain 1R-(3-phenoxy-phenyl)-2-propyn-1-yl (1R, cis, ΔZ) 2,2-dimethyl-3-(3-tert.-butoxy-3-oxo-1-propenyl)-cyclopropane-carboxylate with a specific rotation of $[\alpha]_D^{20}=+58°\pm1.5°$ (c=1.2% in chloroform).

EXAMPLE 61

Using the procedure of Example 9, (1R, cis, ΔZ) 2,2-dimethyl-3-(3-cyclopropymethoxy-3-oxo-1-propenyl)-cyclopropane-carboxylic acid and 1R-(3-phenoxy-phenyl)-ethanol were reacted to obtain 1R-(3-phenoxy-phenyl)-ethyl-(1R, cis, ΔZ) 2,2-dimethyl-3-(3-cyclopropylmethoxy-3-oxo-1-propenyl)-cyclopropane-carboxylate with a specific rotation of $[\alpha]_D^{20}=121°\pm3°$ (c=0.6% in chloroform.

EXAMPLE 62

Using the procedure of Example 9, (1R, cis, ΔZ) 2,2-dimethyl-3-(3-cyclopropylmethoxy-3-oxo-propenyl)-cyclopropane-carboxylic acid and (3-propyn-2-yl-2,5-dioxo-imidazolidinyl)-methanol were reacted to obtain (3-propyn-2-yl-2,5-dioxo-imidazolidinyl)-methyl (1R, cis, ΔZ) 2,2-dimethyl-3-(3-cyclopropylmethoxy-3-oxo-1-propenyl)-cyclopropane-carboxylate with a specific rotation of $[\alpha]_D^{20}=+14°\pm2°$ C. (c=0.5% in chloroform).

EXAMPLE 63

Using the procedure of Example 9, (1R, cis, ΔZ) 2,2-dimethyl-3-(3-cyclopropmethyl-3-oxo-1-propenyl)-cyclopropane carboxylic acid and 1R-(3-phenoxyphenyl)-2-propyn-1-yl alcohol were reacted to obtain 1R-(3-phenoxy-phenyl)-2-propyn-1-yl (1R, cis, ΔZ) 2,2-dimethyl-3-(3-cyclopropylmethoxy-3-oxo-1-propenyl)-cyclopropane-carboxylate with a specific rotation of $[\alpha]_D^{20}=+46°\pm2°$ (c=0.5% in chloroform).

EXAMPLE 64

(3-propyn-2-yl-2,5-dioxo-imidazolidinyl)-methyl (1R, cis, ΔZ) 2,2-dimethyl-3-(3-n-butoxy-3-oxo-1-propenyl)-cyclopropane-carboxylate STEP A: Tert.-butyl (1R, cis) 2,2-dimethyl-3-(3-n-butoxy-3-oxo-1-propynyl)-cyclopropane-carboxylate 3.4 g of dicyclohexyl-carbodiimide were added to a mixture of 4 g of tert.-butyl (1R, cis) 2,2-dimethyl-3-(3-hydroxy-3-oxo-1-propynyl)-cyclopropane-carboxylate, 40 ml of methylene chloride and 6 mg of 4-diethylamino-pyridine and the mixture was stirred for 30 minutes under an inert atmosphere. 4 ml of a 1-1 n-butanol and methylene chloride mixture were added over 5 minutes to the mixture which was then stirred at room temperature for 3 hours and was filtered. The filtrate was evaporated to dryness under reduced pressure and the residue was chromatographed over silica gel. Elution with a 9-1 cyclohexane-ethyl acetate mixture yielded 4.7 g of tert.-butyl (1R, cis) 2,2-dimethyl-3-(3-n-butoxy-3-oxo-1-propynyl)-cyclopropane-carboxylate.

STEP B: Tert.-butyl (1R, cis, ΔZ) 2,2-dimethyl-3-(n-butoxy-3-oxo-1-propenyl)-cyclopropane-carboxylate

A mixture of 800 mg of palladium hydroxide on barium sulfate and 20 ml of ethyl acetate was stirred under hydrogen for 15 minutes and then a mixture of 4.7 g of the product of Step A, 50 ml of ethyl acetate and 0.8 ml of quinoline was added thereto. The mixture was hydrogenated for 30 minutes and was then filtered. The filtrate was washed with N hydrochloric acid and then with water, dried and evaporated to dryness under reduced pressure. The residue was chromatographed over silica gel and was eluted with a 95-5 cyclohexane-ethyl acetate mixture to obtain 3.4 g of tert.-butyl (1R, cis, ΔZ) 2,2-dimethyl-3-(n-butoxy-3-oxo-1-propenyl)-cyclopropane-carboxylate.

STEP C: (1R, cis, ΔZ) 2,2-dimethyl-3-(3-n-butoxy-3-oxo-1-propenyl)-cyclopropane-carboxylic acid A mixture of 3.3 g of Step B, 350 mg of p-toluene sulfonic acid and 40 ml of toluene was refluxed until isobutylene gas evolution ceased (about 40 minutes) and was then evaporated to dryness under reduced pressure. The residue was chromatographed over silica gel and was eluted with a 75-25-1 cyclohexane-ethyl acetate-acetic acid mixture to obtain 2 g of (1R, cis, ΔZ) 2,2-dimethyl-3-(3-n-butoxy-3-oxo-1-propenyl)-cyclopropane-carboxylic acid.

NMR Spectrum (deuterochloroform): Peaks at 1.26 and 1.3 ppm (hydrogens of geminal methyls); at 1.85-1.99 ppm (1-hydrogen of cyclopropyl); at 3.13 to 3.47 ppm (3-hydrogen of cyclopropyl); at 6.4-6.57 ppm and 6.59-6.75 ppm (1-hydrogen of allyl chain); at 5.8-5.99 ppm (2-hydrogens of allyl).

STEP D: (3-propyn-2-yl-2,5-dioxo-imidazolidinyl)-methyl (1R, cis, ΔZ) 2,2-dimethyl-3-(3-n-butoxy-3-oxo-1-propenyl)-cyclopropane-carboxylate Using the procedure of Example 9, the product of Step C and (3-propyn-2-yl-2,5-dioxo-imidazolidinyl)-methanol were reacted to obtain (3-propyn-2-yl-2,5-dioxo-imidazolidinyl)-methyl (1R, cis, ΔZ) 2,2-dimethyl-2-(3-n-butoxy-3-oxo-1-propenyl)-cyclopropane-carboxylate with a specific rotation of $[\alpha]_D^{20} = +17° \pm 1°$ (c=1% in chloroform).

EXAMPLE 65

Using the procedure of Example 9, (1R, cis, Z) 2,2-dimethyl-3-(3-ethoxy-3-oxo-1-propenyl)-cyclopropane-carboxylic acid and (S) cyano-(3-phenoxy-4-fluoro-phenyl)-methanol were reacted to obtain (S) cyano-(3-phenoxy-4-fluoro-phenyl)-methyl (1R, cis, ΔZ) 2,2-dimethyl-3-(3-ethoxy-3-oxo-1-propenyl)cyclopropane-carboxylate with a specific rotation of $[\alpha]_D^{20} = +47.5° \pm 2°$ (c=0.5% in chloroform).

EXAMPLE 66

Using the procedure of Example 9, (1R, cis, ΔZ) 2,2-dimethyl-3-(3-isopropoxy-3-oxo-1-propenyl)-cyclopropane-carboxylic acid and (S) cyano-(3-phenoxy-4-fluoro-phenyl)-methanol were reacted to obtain (S) cyano-(3-phenoxy-4-fluoro-phenyl)-methyl (1R, cis, ΔZ), 2,2-dimethyl-3-(3-isopropoxy-3-oxo-1-propenyl)-cyclopropane-carboxylate with a specific rotation of $[\alpha]_D^{20} = +50° \pm 2°$ (c=0.3% in chloroform).

EXAMPLE 67

Using the procedure of Example 9, (1R, cis, ΔZ) 2,2dimethyl-3-(3-cyclopropyl-methoxy-3-oxo-1-propenyl)-cyclopropane-carboxylic acid and (S) cyano-(3-phenoxy-4-fluoro-phenyl)methanol were reacted to obtain (S) cyano-(3-phenoxy-4-fluoro-phenyl)-methyl (1R, cis, ΔZ) 2,2-dimethyl-3-(3-cyclopropylmethoxy-3-oxo-1-propenyl)-cyclopropane-carboxylate with a specific rotation of $[\alpha]_D^{20} = +53°$ (c=0.25% in chloroform).

EXAMPLE 68

Using the procedure of Example 9, (1R, cis, ΔZ) 2,2-dimethyl-3-(3-tert.-butoxy-3-oxo-1-propenyl)-cyclopropane-carboxylic acid and 2,3,4,5,6-pentafluorobenzyl alcohol were reacted to obtain 2,3,4,5,6-pentafluorobenzyl (1R, cis, ΔZ) 2,2-dimethyl-3-(3-tert.-butoxy-3-oxo-1-propenyl)-cyclopropane-carboxylate with a specific rotation of $[\alpha]_D^{20} = +37.5° \pm 1.5°$ (c=1% in chloroform).

EXAMPLE 69

Using the procedure of Example 9, (1R, cis, ΔZ) 2,2-dimethyl-3-(3-tert.-butoxy-3-oxo-1-propenyl)-cyclopropane-carboxylic acid and (3-phenoxy-4-fluoro-phenyl)-methanol were reacted to obtain (3-phenoxy-4-fluoro-phenyl)-methyl (1R, cis, ΔZ) 2,2-dimethyl-3-(3-tert.-butoxy-3-oxo-1-propenyl)-cyclopropane-carboxylate with a specific rotation of $[\alpha]_D^{20} = +55.5° \pm 2.5°$ (c=0.5% in chloroform).

EXAMPLE 70

Using the procedure of Example 9, (1R, cis, ΔZ) 2,2-dimethyl-3-(3-methoxy-3-oxo-1-propenyl)-cyclopropane-carboxylic acid and (3-phenoxy-4-fluoro-phenyl)-methanol were reacted to obtain (3-phenoxy-4-fluoro-phenyl)-methyl (1R, cis, ΔZ) 2,2-dimethyl-3-(3-methoxy-3-oxo-1-propenyl)-cyclopropane-carboxylate with a specific rotation of $[\alpha]_D^{20} = +50.5° \pm 2.5°$ (c=0.75% in chloroform).

EXAMPLE 71

Using the procedure of Example 9 (1R, cis, ΔZ) 2,2-dimethyl-3-(3-tert.-butoxy-3-oxo-1-propenyl)-cyclopropane-carboxylic acid and (1R,S)-(3-phenoxy-4-fluoro-phenyl)-ethanol were reacted to obtain (1R,S)-(3-phenoxy-4-fluoro-phenyl)-ethyl (1R, cis, ΔZ) 2,2-dimethyl-3-(3-tert.-butoxy-3-oxo-1-propenyl)-cyclopropane-carboxylate.

NMR Spectrum (deuterochloroform): Peaks at 1.19 to 1.28 ppm (hydrogens of geminal methyls); at 1.48-1.5 ppm (hydrogens of tert.-butyl); at 1.41 to 1.53 ppm (hydrogens of COO—CH—CH₃); at 1.85-1.99 ppm and 3.07 to 3.38 ppm (1- and 3-hydrogens of cyclopropyl); at 5.58 to 6 ppm and 6.27 to 6.7 ppm (ethylenic hydrogens); at 6.27 to 6.7 ppm (hydrogen of —COOCH₂—); at 6.92 to 7.53 ppm (aromatic hydrogens).

EXAMPLE 72

Using the procedure of Example 9, (1R, cis, ΔZ) 2,2-dimethyl-3-(3-methoxy-3-oxo-1-propenyl)-cyclopropane-carboxylic acid and (1R,S) (3-phenoxy-4-fluoro-phenyl)-ethanol were reacted to obtain (1R,S) (3-phenoxy-4-fluoro-phenyl)-ethyl (1R, cis, ΔZ) 2,2- dimethyl-3-(3-methoxy-3-oxo-1-propenyl)-cyclopropane-carboxylate.

NMR Spectrum (deuterochloroform): Peaks at 1.19 to 1.29 ppm (hydrogens of geminal methyls); at 1.41 to 1.54 ppm (hydrogens of —COOCH—CH$_3$); at 1.87–2.02 ppm and 3.07 to 3.22 ppm (1- and 3-hydrogens of cyclopropyl; at 5.82 to 6.17 ppm (hydrogen of COO—CH$_2$—); at 5.93 to 6.2 ppm and 6.58 to 7 ppm (ethylenic hydrogens); at 7.03 to 7.72 ppm (aromatic hydrogens).

Preparation of 3-phenoxy-4-fluoro-methyl benzylic alcohol 15.8 cm3 of a 2.6M solution of methyl magnesium iodide in ethyl ether are added at 20° C. to a mixture containing 8 g of 3-(4-fluorophenoxy) benzaldehyde in 50 cm3 of ethyl ether. The mixture is maintained at ambiant temperature during one hour, then is poured in an aqueous solution of ammonium chloride, decanted, extracted with ethyl ether, the expected product is obtained and then is cristallized in isopropyl ether. M Pt: 64° C.

EXAMPLE 73

Using the procedure of Example 9, (1R, cis, ΔZ) 2,2-dimethyl-3-(3-tert.-butoxy-3-oxo-1-propenyl)-cyclopropane-carboxylic acid and 5-benzyl-3-furyl-methanol were reacted to obtain 5-benzyl-3-furyl-methyl (1R, cis, ΔZ) 2,2-dimethyl-3-(3-tert.-butoxy-3-oxo-1-propenyl)-cyclopropane-carboxylate with a specific roation of $[\alpha]_D^{20} = +54.5° \pm 1.5°$ (c=1% in chloroform).

EXAMPLE 74

Using the procedure of Example 9, (1R, cis, ΔZ) 2,2-dimethyl-3-(3-tert.-butoxy-3-oxo-1-propenyl)-cyclopropane-carboxylic and (1S) 2-methyl-4-oxo-3-(2-propenyl)-cyclopenten-1-yl alcohol were reacted to obtain (1S) 2-methyl-4-oxo-3-(2-propenyl)-cyclopenten-1-yl (1R, cis, ΔZ) 2,2-dimethyl-3-(3-tert.-butoxy-3-oxo-1-propenyl)-cyclopropane-carboxylate with a specific rotation of $[\alpha]_D^{20} = +73°$ (c=0.25% in chloroform).

EXAMPLE 75

(2-phenoxy-5-thiazolyl)-methyl (1R, cis, ΔZ) 2,2-dimethyl-3-(3-methoxy-3-oxo-1-propenyl)-cyclopropane-carboxylate STEP A: Ethyl 2-phenoxy-thiazole-5-carboxylate A mixture of 2 g of ethyl 2-chloro-thiazole-5-carboxylate, 50 ml of dimethylformamide, 2.5 ml of hexamethylphosphorotriamide and 1.5 g of sodium iodide was heated at 100° C. for one hour and was then cooled to 20° C. after which 1.32 g of potassium phenate were added portion wise. The mixture was refluxed for 90 minutes and another 0.66 g of potassium phenate were added thereto. The mixture was refluxed for 90 minutes and was cooled and water and ethyl acetate were added thereto. The mixture was extracted with ethyl acetate and the organic phase was washed with water and evaporated to dryness under reduced pressure. The residue was chromatographed over silica gel and was eluted with a 7-3-1 hexane-isopropyl ether triethylamine mixture to obtain 1.08 g of ethyl 2-phenoxythiazole-5-carboxylate melting at 67° C.

STEP B: (2-phenoxy-5-thiazolyl)-methanol 54 ml of a solution of 2 moles of diethyl sodium aluminate in toluene were slowly added at −10° C. to a solution of 12 g of the product of Step A in 60 ml of toluene and the mixture was stirred at −5° C. for one hour. The mixture was cooled to −20° C. while adding thereto 80 ml of a solution of aqueous 2N hydrochloric acid and the mixture was filtered. The filtrate was decanted and the organic phase was washed with water, with an aqueous 2N sodium hydroxide solution and then with water and was evaporated to dryness under reduced pressure. The residue was chromatographed over silica gel and was eluted with an 8-2 methylene chloride-ethyl acetate mixture to obtain 8.15 g of (2-phenoxy-5-thiazolyl)-methanol.

IR Spectrum (chloroform): Absorption at 3590 cm$^{-1}$ (OH); at 1551, 1530, 1503 and 1486 cm$^-$ (aromatic ring and thiazolyl); at 690 cm$^{-1}$ (phenyl)-deformation).

NMR Spectrum (deuterochloroform): Peaks at 4.5 ppm (hydrogens of —CH$_2$O—); at 3.5 ppm (—OH hydrogen); at 6.66 ppm (thiazolyl); at 7.10 to 7.50 ppm (aromatic hydrogens).

STEP C: (2-phenoxy-5-thiazolyl)-methyl (1R, cis, ΔZ) 2,2-dimethyl-3-(3-methoxy-3-oxo-1-phenyl)-cyclopropane-carboxylate Using the procedure of Example 9, the product of Step B and (1R, cis ΔZ) 2,2-dimethyl-3-(3-methoxy-3-oxo-1-propenyl)cyclopropane-carboxylic acid were reacted to obtain (2-phenoxy-5-thiazolyl)-methyl (1R, cis, ΔZ) 2,2-dimethyl-3-(3-methoxy-3-oxo-1-propenyl)-cyclopropane-carboxylate melting at 62° C. and havng a specific rotation of $[\alpha]_D^{20} = +60.5° \pm 1.5°$ (c=1.5% in benzene).

EXAMPLE 76

(R,S) (thiamido-phenoxy-phenyl)-methyl (1R, cis, ΔZ) 2,2-dimethyl-3-(3-methoxy-3-oxo-1-propenyl)-cyclopropane-carboxylate STEP A: 3-phenoxy-2-hydroxy-benzene-ethanethioamide Hydrogen sulfide was bubbled through a solution of 20 g of α-cyano-3-phenoxy-benzyl alcohol, 200 ml of toluene and 4.5 ml of triethylamine for 22 hours and the mixture was then poured into aqueous N hydrochloric acid. The decanted organic phase was washed with water, dried and evaporated to dryness under reduced pressure and the residue was chromatographed over silica gel. Elution with an 8-2 benzene-ethyl acetate mixture and cyrstallization from isopropyl ether yielded 18.5 g of 3-phenoxy-2-hydroxy-benzene-ethanethioamide melting at 70° C.

IR Spectrum (chloroform): Absorption at 3600 cm$^{-1}$ (free and associated OH); at 3478 and 3360 cm$^{-1}$ (—NH$_2$); at 1670, 1578 and 1477 cm$^{-1}$ (aromatic rings and

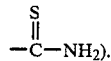

NMR Spectrum (chloroform): Peaks at 3.97–4.03 ppm (hydrogen of —OH); at 5.18–5.25 ppm (hydrogen on carbon attached αto

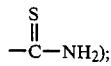

at 6.92 to 7.58 ppm (aromatic hydrogens); at 7.5 ppm (hydrogens of —NH$_2$).

STEP B: (R,S) (thioamido-phenoxy-phenyl)-methyl (1R, cis, ΔZ) 2,2-dimethyl-3-(3-methoxy-3-oxo-1-propenyl)-cyclopropane-carboxylate Using the procedure of Example 9, the product of Step A and (1R, cis ΔZ) 2,2-dimethyl-3-(3-methoxy-3-oxo-1-propenyl)-cyclopropane-carboxylic acid were reacted to obtain (R,S) (thioamido-phenoxy-phenyl)-methyl (1R, cis, ΔZ) 2,2-dimethyl-3-(3-methoxy-3-oxo-1-propenyl)-cyclopropane-carboxylate.

IR Spectrum (chloroform): Absorption at 1632 cm$^{-1}$ (C=C); at 3475-3365 cm$^{-1}$

at 1713-1736 cm$^{-1}$ (C=O).

NMR Spectrum (deuterochloroform): Peaks at 1.25-1.27-1.30 ppm (hydrogens of geminal methyls); at 1.97-2.11 ppm (1-hydrogen of cyclopropyl); at 3.08-3.43 ppm (3-hydrogen of cyclopropyl); at 3.69-3.72 ppm (hydrogens of CH$_3$O); at 5.73-5.92 ppm and 5.8-5.99 ppm (ethylenic hydrogen α to —COOCH$_3$); at 6.32-6.66 ppm (ethylenic 1-hydrogen of COOCH$_3$); at 6.42 ppm (hydrogen on carbon attached to

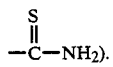

EXAMPLE 77

Using the procedure of Example 9, (1R, cis, ΔZ) 2,2-dimethyl-3-(3-tert.-butoxy-3-oxo-1-propenyl)-cyclopropane-carboxylic acid and (2-phenoxy-4-thiazolyl)-methanol were reacted to obtain (2-phenoxy-5-thiazolyl)-methyl (1R, cis, ΔZ) 2,2-dimethyl-3-(3-tert.-butoxy-3-oxo-1-propenyl)-cyclopropane-carboxylate with a specific rotation of $[\alpha]_D^{20} = +68° \pm 1.5°$ (c=1% in chloroform).

EXAMPLE 78

(R,S) cyano (2-phenoxy-5-thiazolyl)-methyl (1R, cis ΔZ) 2,2-dimethyl-3-(3-methoxy-b 3-oxo-1-propenyl)-cyclopropane-carboxylate STEP A: (2-phenoxy-5-thiazolyl)-methanol A mixture of 19.1 g of manganese dioxide and 4.6 g of (2-phenoxy-5-thiazolyl)-methanol was stirred at 40° C. for 17 hours and then at 60° C. for 3 hours and was then filtered. The filtrate was evaporated to dryness under reduced pressure and the residue was chromatographed over silica gel. Elution with 8-2 methylene chloride-ethyl acetate mixture yielded 2.6 g of (2-phenoxy-5-thiazolyl)-methanol with a melting point of 63° C.

STEP B: (R,S) α-cyano-(2-phenoxy-5-thiazolyl)-methanol

A solution of 2.4 g of the product of Step A in 10 ml of ether was added at 10° C. to a solution of 0.85 g of sodium cyanide in 5 ml of water and the mixture was stirred at 0° C. for 10 minutes. A mixture of 2 ml of aqueous concentrated sulfuric acid and 3 ml of water were added dropwise at 0° C. to the mixture which was then stirred at 0° C. for 2 hours. The decanted organic phase was washed with water, dried and evaporated to dryness under reduced pressure. The residue was added to isopropyl ether and the mixture was vacuum filtered. The product was dried to obtain 2.28 g 9f (R,S) α-cyano-(2-phenoxy-5-thiazolyl)-methanol.

IR Spectrum (chloroform): Absorption at 3580 cm$^{-1}$ (OH); at 3550 cm$^{-1}$ (associated OH); at 1590, 1504 and 1487 cm$^{-1}$ (aromatic ring and thiazolyl).

NMR Spectrum (deuterochloroform): Peaks at 4.08 ppm (hydrogen of —OH); at 5.41 ppm (hydrogen of CH—OH); at 7.33 ppm (aromatic hydrogens); at 7.0 ppm (thiazolyl hydrogen).

STEP C: (R, S) cyano-(2-phenoxy-5-thiazolyl)-methyl (1R, cis ΔZ) 2,2-dimethyl-3-(3-methoxy-3-oxo-1-propenyl)-cyclopropane-carboxylate Using the procedure of Example 9, the product of Step B and (1R, cis, ΔZ) 2,2-dimethyl-3-(3-methoxy-3-oxo-1-propenyl)-cyclopropane-carboxylic acid were reacted to obtain (R, S) cyano-(2-phenoxy-5-thiazolyl)-methyl (1R, cis, ΔZ) 2,2-dimethyl-3-(3-methoxy-3-oxo-1-propenyl)-cyclopropane-carboxylate with a specific rotation of $[\alpha]_D^{20} = +60° \pm 2°$ (c=1% chloroform).

EXAMPLE 79

Using the procedure of Example 9, (1R, cis, ΔZ) 2,2-dimethyl-3-(3-tert.-butoxy-3-oxo-1-propenyl)-cyclopropane-carboxylic acid and (R, S) cyano-(2-phenoxy-5-thiazolyl)-methanol were reacted to obtain (R, S) cyano-(2-phenoxy-5-thiazolyl)-methyl (1R, cis, ΔZ) . 2,2-dimethyl-3-(3-tert.-butoxy-3-oxo-1-propenyl)-cyclopropane-carboxylate with a specific rotation of $[\alpha]_D^{20} = +65° \pm 2°$ (c=0.5% in chloroform):

EXAMPLE 80

1R-(3-phenoxy-phenyl)-ethyl (1R, trans, ΔZ) 2,2-dimethyl-3-(-3-isopropoxy-3-oxo-1-propenyl)-cyclopropane-carboxylate STEP A: Tert.-butyl (1R, trans) 2,2-dimethyl-3-(3-hydroxy-3-oxo-1-propynyl)-cyclopropane-carboxylate Using the procedure of Step A of Example 2, 40 g of tert.-butyl (1R, trans) 2,2-dimethyl-3-(2,2-dibromovinyl)-cyclopropane-carboxylate were reacted and the product was chromatographed over silica gel. Elution with a 6-4-0.2 cyclohexane-ethyl acetate-acetic acid mixture yielded 19.2 g of tert.-butyl (1R, trans) 2,2-dimethyl-3-(3-hydroxy-3-oxo-1-propynyl)-cyclopropane-carboxylate STEP B: Tert.-butyl (1R, trans) 2,2-dimethyl-3-(3-isopropoxy-3-oxo-1-propynyl)-cyclopropane-carboxylate 3 g of 0-isopropyl-N,N'-diisopropyl-urea were added to a mixture of 3.6 g of the product of Step A in 20 ml of ethyl acetate and the mixture was refluxed with stirring for 16 hours and was then cooled to room temperature. The mixture was filtered and the filtrate was evaporated to dryness under reduced pressure to obtain 2.7 g of tert.-butyl (1R, trans) 2,2-dimethyl-3-(3-isopropoxy-3-oxo-1-propynyl)-cyclopropane-carboxylate.

STEP C: Tert.-butyl (1R, trans, ΔZ) 2,2-dimethyl-3-dimethyl-3-(3-isopropoxy-3-oxo-1-propenyl)-cyclopropane-carboxylate A mixture of 2.7 g of the product of Step B, 0.55 g of 10% palladium hydroxide on barium sulfate, 0.55 ml of quinolin and 50 ml of ethyl acetate was hydrogenated and the mixture was filtered. The filtrate was washed with N hydrochloric acid, then with water until the wash water was neutral, dried and evaporated to dryness under reduced pressure to obtain 2.18 g of tert.- butyl (1R, trans, ΔZ) 2,2-dimethyl-3-(3-isopropoxy-3-oxo-1-propenyl-cyclopropane-carboxylate.

STEP D: (1R, trans, ΔZ) 2,2-dimethyl-3-(3-isopropoxy-3-oxo-1-propenyl)-cyclopropane-carboxylic acid A mixture of 2.18 g of the product of Step C, 20 ml of toluene and 0.2 ml of p-toluene sulfonic acid was refluxed and then cooled to room temperature. The organic phase was washed with water, dried and evaporated to dryness under reduced pressure to obtain 1.6 g of (1R, trans, ΔZ) 2,2-dimethyl-3-(3-isopropoxy-3-oxo-1-propenyl)-cyclopropane-carboxylic acid.

STEP E: (1R) (3-phenoxy-phenyl)-ethyl (1R, trans, ΔZ) 2,2-dimethyl-3-(3-isopropoxy-3-oxo-1-propenyl)-cyclopropane-carboxylate Using the procedure of Example 9, the product of Step D and (1R)-(3-phenoxy-phenyl)-ethanol were reacted to obtain (1R) (3-phenoxy-phenyl)-ethyl (1R, trans, ΔZ) 2,2-dimethyl-3-(3-isopropoxy-3-oxo-1-phenyl)-cyclopropane-carboxylate with a specific rotation of $[\alpha]_D^{20} = +59.°\pm1.5°$ (c=1% in chloroform).

EXAMPLE 81

(1R)-(3-phenoxy-phenyl)-ethyl (1R, cis, ΔZ) 2,2-dimethyl-3-(3-allyloxy-3-oxo-1-propenyl)-cyclopropane-carboxylate STEP A: Tert.-butyl (1R, cis) 2,2-dimethyl-3-(3-trichloro-ethoxy-3-oxo-1-propynyl)-cyclopropane-carboxylate A mixture of 6.2 g of dicyclohexylcarbodiimide, 7.15 g of tert.-butyl (1R, cis) 2,2-dimethyl-3-(3-hydroxy-3-oxo-1-propynyl)-cyclopropane-carboxylate, 80 mg of 4-dimethylaminopyridine and 35 ml of methylene chloride was stirred for 10 minutes and 4.5 g of 2,2,2-trichloroethanol were added thereto. The mixture was stirred for one hour and was filtered and the filtrate was washed with N hydrochloric acid and then with water until the wash water was neutral, was dried and evaporated to dryness. The 14 g of oil residue was chromatographed over silica gel and were eluted with a 97-3 benzene-ethyl acetate mixture to obtain 9 g of tert.-butyl (1R, cis) 2,2-dimethyl-3-(3-trichloro-ethoxy-3-oxo-1-propynyl)-cyclopropane-carboxylate melting at 70°–71° C.

STEP B: (1R, cis) 2,2-dimethyl-3-(3-trichloroethoxy)-3-oxo-1-propynyl)-cyclopropane-carboxylic acid A mixture of 11.4 g of the product of Step A, 120 ml of toluene and 300 mg of p-toluene sulfonic acid was refluxed for one hour and was cooled to room temperature. The mixture was washed with water, dried and evaporated to dryness under reduced pressure to obtain 9.5 g of (1R, cis) 2,2-dimethyl-3-(3-trichloroethoxy)-3-oxo-1-propynyl)-cyclopropane-carboxylic acid which has used as is for the next step.

STEP C: 1R-(3-phenoxy-phenyl)-ethyl (1R, cis) 2,2-dimethyl-3-(3-trichloroethoxy-3-oxo-1-propynyl)-cyclopropane-carboxylate 3.95 g of dicyclohexylcarbodiimide were added to 0° C. with stirring to a solution of 6 g of Step B, 600 mg of 4-dimethylamino-pyridine and 30 ml of methylene chloride and the mixture was stirred at 0° C. for 30 minutes. A solution of 4.1 g of 1(R)-(3-phenoxy-phenyl)-ethanol in 12 ml of methylene chloride was added dropwise to the mixture of 0° C. and the mixture was stirred at room temperature for 17 hours and was filtered. The filtrate was evaporated to dryness under reduced pressure and the oil residue was chromatographed over silica gel. Elution with an 8-2 cyclohexane-ethyl acetate mixture yielded 4.4 g of 1R-(3-phenoxy-phenyl)-ethyl (1R, cis) 2,2-dimethyl-3-(3-trichloroethoxy-3-oxo-1-propynyl)-cyclopropane-carboxylate.

STEP D: 1R-(3-phenoxy-phenyl)-ethyl (1R, cis) 2,2-dimethyl-3-(3-hydroxy-3-oxo-1-propynyl)-cyclopropane-carboxylate 0.53 g of powdered zinc were added with stirring to a solution of 4.16 g of the product of Step C in 4 ml of methylene chloride and 45 ml of acetic acid and the mixture was stirred at room temperature for 30 minutes. Another 0.53 g of powdered zinc were added thereto and the operation was reported twice more. The mixture was filtered to remove residual zinc and the filter was rinsed with 40 ml of water and 100 ml of methylene chloride. The filtrate was extracted with methylene chloride and the organic phase was washed, dried and evaporated to dryness under reduced pressure to obtain 3.05 g of 1R-(3-phenoxy-phenyl)-ethyl (1R, cis) 2,2-dimethyl-3-(3-hydroxy-3-oxo-1-propynyl)-cyclopropane-carboxylate.

STEP E: 1R-(3-phenoxy-phenyl)-ethyl (1R, cis, ΔZ) 2,2-dimethyl-3-(3-hydroxy-3-oxo-1-propynyl)-cyclopropane-carboxylate A mixture of 3 g of the product of Step D, 500 mg of 10% palladium hydroxide on barium sulfate, 0.9 ml of quinoline and 80 ml of ethyl acetate was hydrogenated and the mixture was filtered. The filtrate was washed with hydrochloric acid and with water, dried and evaporated to dryness under reduced pressure to obtain 2.9 g of 1R-(3-phenoxy-phenyl)-ethyl (1R, cis, ΔZ) 2,2-dimethyl-3-(3-hydroxy-3-oxo-1-propynyl)-cyclopropane-carboxylate.

STEP F: 1R-(3-phenoxy-phenyl)-ethyl (1R, cis, ΔZ) 2,2-dimethyl-3-(3-allyloxy-3-oxo-1-propenyl)-cyclopropane-carboxylate 760 mg of dicyclohexylcarbodiimide were added with stirring at 0° C. to a mixture of 1.4 g of the product of Step E, 7 ml of methylene chloride and 0.14 g of 4-dimethylaminopyridine and the mixture was stirred at 0° C. for 20 minutes. A solution of 0.26 ml of allyl chloride in 2 ml of methylene chloride was added at 0° C. to the mixture and the mixture was stirred at room temperature for one hour and was filtered. The filtrate was evaporated to dryness under reduced pressure and the oil residue was chromatographed over silica gel. Elution with 8-2 hexane-isopropyl ether yielded 570 mg of 1R-(3-phenoxy-phenyl)-ethyl (1R, cis, ΔZ) 2,2-dimethyl-3-(3-allyloxy-3-oxo-1-propenyl)-cyclopropane-carboxylate with a specific rotation of $[\alpha]_D^{20} = +109.5°\pm2°$ (c=1% in chloroform).

EXAMPLE 82

1R-(3-phenoxy-phenyl)-ethyl (1R, cis, ΔZ) 2,2-dimethyl-3-(3-tert.-butoxy-3-oxo-1-propenyl)-cyclopropane-carboxylate 1.4 g of 0-tert.-butyl-N,N'-diisopropyl-urea were added with stirring at room temperature to a solution of 1.74 g of the product of Step E of Example 81 in 8 ml of ethyl acetate and the mixture was stirred for 4 hours and was filtered. The filtrate was evaporated to dryness under reduced pressure and the residue was chromatographed over silica gel. Elution with an 8-2 hexane-ether mixture yielded 930 mg of 1R-(3-phenoxy-phenyl)-ethyl (1R, cis, ΔZ) 2,2-dimethyl-3-(3-tert.-butoxy-3-oxo-1-propenyl)-cyclopropane-carboxylate melting at 80° C. and having a specific rotation of $[\alpha]_D^{20} = +125°\pm2°$ (c=1% in chloroform).

EXAMPLE 83 m-phenoxy-benzyl (1R, cis, ΔZ), 2,2-dimethyl-3-(3-tert.-butoxy-3-oxo-1-propenyl)-cyclopropane-carboxylate STEP A: m-phenoxy-benzyl (1R, cis) 2,2-dimethyl-3-(3-trichloroethoxy-3-oxo-propynyl)-cyclopropane-carboxylate A solution of 4.5 g of m-phenoxy-benzyl alcohol in 5 ml of methylene chloride was added with stirring at 0° C. to a mixture of 6.7 g of the product of Step B of Example 81, 67 ml of methylene chloride and 200 mg of 4-dimethylamino-pyridine and then a solution of 4.4 g of dicyclohexylcarbodiimide in 5 ml of methylene chloride was added thereto. The mixture was stirred at room temperature for 3 hours and was filtered and the filtrate was evaporated to dryness under reduced pressure. The 11.5 g of oil residue were chromatographed over silica gel and eluted with an 85-15 cyclohexane-ethyl acetate mixture to obtain 7.1 g of m-phenoxy-benzyl (1R, cis) 2,2-dimethyl-3-(3-trichloroethoxy)-3-oxo-propynyl)-cyclopropane-carboxylate STEP B: m-phenoxy-benzyl (1R, cis) 2,2-dimethyl-3-(3-hydroxy-3-oxo-1-propynyl)-cyclopropane-carboxylate 5 g of powdered zinc were added with stirring to a solution of 5 g of the product of Step A in 18 ml of acetic acid and 2 ml of water and the mixture was stirred at room temperature for 2 hours and was then filtered. The filter was rinsed with water and then with methylene chloride and the organic phase of the filtrate was washed with water, dried and evaporated to dryness under reduced pressure. The residue was taken up in toluene and the solution was evaporated to dryness under reduced pressure. This operation was repeated 3 times to obtain 3.6 g of m-phenoxy-benzyl (1R, cis) 2,2-dimethyl-3-(3-hydroxy-3-oxo-1-propynyl)-cyclopropane-carboxylate which was used as is for the next step.

STEP C: m-phenoxy-benzyl (1R, cis) 2,2-dimethyl-3-(3-tert.-butoxy-3-oxo-1-propynyl)-cyclopropane-carboxylate 4 ml of O-tert.-butyl-N,N'-diisopropyl-urea were added dropwise with stirring at room temperature to 2 g of the product of Step B and after the addition of 25 ml of ethyl acetate, the mixture was stirred for one hour. 2 ml of acetic acid were added to the mixture to destroy excess reagent and the mixture was stirred for 15 minutes and was filtered. The filter was rinsed with ethyl acetate and the filtrate was evaporated to dryness under reduced pressure. The 2.8 g of oil residue were chromatographed over silica gel and eluted with an 8-2 cyclohexane-ethyl acetate mixture to obtain 1.4 g of m-phenoxy-benzyl (1R, cis) 2,2-dimethyl-3-(3-tert.-butoxy-3-oxo-1-propynyl)-cyclopropane-carboxylate.

STEP D: m-phenoxy-benzyl (1R, cis, ΔZ) 2,2-dimethyl-3-(3-tert.-butoxy-3-oxo-1-propenyl)-cyclopropane-carboxylate A mixture of 1.4 g of the product of Step C, 30 ml of ethyl acetate, 500 mg of 10% palladium hydroxide on barium sulfate and 0.7 ml of quinoline was hydrogenated and the mixture was filtered. The filtrate was washed with 2N hydrochloric acid and with water, was dried and evaporated to dryness under reduced pressure. The oil residue was chromatographed over silica gel and was eluted with a 9-1 cyclohexane-ethyl acetate mixture and then with a 95-5 cyclohexane-ethyl acetate mixture to obtain 1 g of m-phenoxy-benzyl (1R, cis, ΔZ) 2,2-dimethyl-3-(3-tert.-butoxy-3-oxo-1-propenyl)-cyclopropane-carboxylate with a specific rotation of $[\alpha]_D^{20} = +38.5° \pm 2.5°$ (c=0.5% in benzene)

EXAMPLE 84

(R, S) cyano-2-(6-phenoxy-2-pyridyl)-methyl (1R, cis, ΔZ) 2,2-dimethyl-3-(3-ethoxy-3-oxo-1-propenyl)-cyclopropane-carboxylate STEP A: (1R, cis) 2,2-dimethyl-3-(3-methoxy-3-oxo-1-propynyl)-cyclopropane-carboxylic acid A solution of 2.6 g of tert.-butyl (1R, cis) 2,2-dimethyl-3-(3-methoxy-3-oxo-propynyl)-cyclopropane-carboxylate 25 ml of toluene and 100 mg of p-toluene sulfonic acid was refluxed for 90 minutes and then cooled to room temperature and stirred for 20 hours. The mixture was evaporated to dryness under reduced pressure to obtain 1.95 g of (1R, cis) 2,2-dimethyl-3-(3-methoxy-3-oxo-1propynyl)-cyclopropane-carboxylic acid.

STEP B: (R, S) cyano-2-(6-phenoxy-pyridyl)-methyl (1R, cis) 2,2-dimethyl-3-(3-methoxy-3-oxo-propynyl)-cyclopropane-carboxylate A solution of 21.6 g of the product of Step A in 75 ml of methylene chloride was added with stirring under an inert atmosphere to a solution of 19.9 g of (R, S) cyano-2-(6-phenoxypyridyl)-methanol in 75 ml of methylene chloride and then 1 g of 4-dimethylamino-pyridine was dissolved therein at 0° C. 21 g of dicyclohexylcarbodiimide were added to the mixture which was then stirred at room temperature for 4 hours and was then filtered. The filtrate was evaporated to dryness under reduced pressure at 40° C. and the residue was chromatographed over silica gel. Elution with a 7-3 cyclohexane-ethyl acetate mixture yielded 35.4 g of (R, S) cyano-2-(6-phenoxy-pyridyl)-methyl (1R, cis) 2,2-dimethyl-3-(3-methoxy-3-oxo-propynyl)-cyclopropane-carboxylate.

STEP C: (R, S) cyano-2-(6-phenoxy-pyridyl)-methyl (1R, cis) 2,2-dimethyl-3-(3-hydroxy-3-oxo-propynyl)-cyclopropane-carboxylate A mixture of 35.4 g of the product of Step B, 175 ml of dioxane, 35 ml of water and 5 g of p-toluene sulfonic acid was refluxed for 24 hours and was then evaporated to dryness under reduced pressure. The residue was taken up in 250 ml of methylene chloride and 100 ml of water and the organic phase was washed with water, dried and evaporated to dryness under reduced pressure. The residue was chromatographed over silica gel and was eluted with a 6-4 cyclohexane-ethyl acetate mixture containing 0.1% of acetic acid to obtain 17.7 g of (R; S) cyano 2-(6-phenoxy-pyridyl)-methyl (1R, cis) 2,2-dimethyl-3-(3-hydroxy-3-oxo-propynyl)-cyclopropane-carboxylate.

STEP D: (R, S) cyano-2-(6-phenoxy-pyridyl)-methyl (1R, cis, ΔZ) 2,2-dimethyl-3-(3-hydroxy-3-oxo-1-propenyl)-cyclopropanecarboxylate A mixture of 17.7 g of the product of Step C, 200 ml of ethyl acetate, 2.5 g of 10% palladium hydroxide on barium sulfate and 2.5 ml of quinoline was hydrogenated at 20° C. and was filtered. The filrate was dried and evaporated to dryness under reduced pressure. The residue was chromatographed over silica gel and was eluted with a 6-4-0.1 cyclohexane-ethyl acetate-acetic acid mixture to obtain 15 g of (R, S) cyano-2-(6-phenoxy-pyridyl)-methyl (1R, cis, ΔZ) 2,2-dimethyl-3-(3-hydroxy-3-oxo-1-propenyl)-cyclopropane-carboxylate.

STEP E: (R, S) cyano-2-(6-phenoxy-pyridyl)-methyl (1R, cis, ΔZ) 2,2-dimethyl-3-(3-ethoxy-3-oxo-1-propenyl)-cyclopropane-carboxylate First 70 mg of 4-dimethylamino-pyridine and then 1.13 g of dicyclohexylcarbodiimide were added with stirring under a nitrogen atmosphere to a solution of 1.95 g of the product of Step D in 10 ml of methylene chloride and 2 ml of ethanol cooled to 0° C. and the mixture was stirred at room temperature for 90 minutes and was filtered. The filter was washed with methylene chloride and the filtrate was evaporated to dryness under reduced pressure. The residue was chromatographed over silica gel and was eluted with first 8-2 cyclohexane-ethyl acetate mixture and then with an 85-15 cyclohexane-ethyl acetate mixture to obtain 1.4 g of (R, S) cyano-2-(6-phenoxypyridyl)-methyl (1R, cis, ΔZ) 2,2-dimethyl-3-(3-ethoxy-3-oxo-1-propenyl)-cyclopropane-carboxylate with a specific rotation of $[\alpha]_D^{20} = +48° \pm 2°$ (c=0.5% in chloroform).

EXAMPLE 85

(R, S) cyano-2-(6-phenoxy-pyridyl)-methyl (1R, cis, ΔZ) 2,2-dimethyl-3-(3-isopropoxy-3-oxo-1-propenyl)-cyclopropane-carboxylate Using the procedure of Example 84, 1.95 g of (R, S) cyano-2-(6-phenoxy-pyridyl)-methyl (1R, cis, ΔZ) 2,2-dimethyl-3-(3-hydroxy-3-oxo-1-propenyl)-cyclopropane-carboxylate and 2 ml of isopropanol were reacted and the oil residue was chromatographed over silica gel. Elution with a 9-1 cyclohexane-ethyl acetate mixture yield 1.7 g of (R, S) cyano-2-(6-phenoxy-pyridyl)-methyl (1R, cis, ΔZ) 2,2-dimethyl-3-(3-isopropoxy-3-oxo-1-propenyl)-cyclopropane-carboxylate with a specific rotation of $[\alpha]_D^{20} = +53° \pm 2°$ (c=0.75% in chloroform).

EXAMPLE 86

(R, S) cyano-2-(6-phenoxy-pyridyl)-methyl (1R, cis, ΔZ) 2,2-dimethyl-3-(3-cyclobutoxy-3-oxo-1-propenyl)-cyclopropane-carboxylate Using the procedure of Example 84, 2.1 g of (R, S) cyano-2-(6-phenoxy-pyridyl)-methyl (1R, cis, ΔZ) 2,2-dimethyl-3-(3-hydroxy-3-oxo-1-propenyl)-cyclopropane-carboxylate and 1 ml of cyclobutanol were reacted and the oil residue was chromatographed over silica gel. Elution with an 8-1 cyclohexane-ethyl acetate mixture yielded 1.6 g of (R, S) cyano-2-(6-phenoxy-pyridyl)-methyl (1R, cis, ΔZ) 2,2-dimethyl-3-(3-cyclobutoxy-3-oxo-1-propenyl)-cyclopropane-carboxylate with a specific rotation of $[\alpha]_D^{20} = +44.5° \pm 2°$ (c=0.5% in benzene).

EXAMPLE 87

(R, S) cyano-2-(6-phenoxy-pyridyl)-methyl (1R, cis, ΔZ) 2,2-dimethyl-3-(3-n-butoxy-3-oxo-1-propenyl)-cyclopropane-carboxylate Using the procedure of Example 84, 2.1 g of (R, S) cyano-2-(6-phenoxy-pyridyl)-methyl (1R, cis, ΔZ) 2,2-dimethyl-3-(3-hydroxy-3-oxo-propenyl)-cyclopropane-carboxylate and 1 ml of n-butanol were reacted and the oil residue was chromatographed over silica gel. Elution with a 9-1 n-hexane-ethyl acetate mixture yield 1.55 g of (R, S) cyano-2-((6-phenoxy-pyridyl)-methyl (1R, cis, ΔZ) 2,2-dimethyl-3-(3-n-butoxy-3-oxo-1-propenyl)- cyclopropane-carboxylate with a specific rotation of $[\alpha]_D^{20} = +52° \pm 2.5°$ (c=0.5% in chloroform).

EXAMPLE 88

(R, S) cyano-2-(6-phenoxy-pyridyl)-methyl (1R, cis, ΔZ) 2,2-dimethyl-3-(3-allyloxy-3-oxo-1-propenyl)-cyclopropane-carboxylate Using the procedure of Example 84, 2.1 g of (R, S) cyano-2-(6-phenoxy-pyridyl)-methyl (1R, cis, ΔZ) 2,2-dimethyl-3-(3-hydroxy-3-oxo-1-propenyl)-cyclopropane-carboxylate and 0.8 ml of allyl alcohol were reacted and the oil residue was chromatographed over silica gel. Elution with an 85-15 n-hexane-ethyl acetate mixture yielded 1.55 g of (R, S) cyano-2-(6-phenoxy-pyridyl)-methyl (1R, cis, ΔZ) 2,2-dimethyl-3-(3-allyloxy-3-oxo-1-propenyl)-cyclopropane-carboxylate with a specific rotation of $[\alpha]_D^{20} = +53° \pm 3°$ (c=0.3% in chloroform).

EXAMPLE 89

3-phenoxy-benzyl (1R, cis, ΔZ) 2,2-dimethyl-3-[3(1,1-dimethylpropoxy)-3-oxo-1-propenyl]-cyclopropane-carboxylate STEP A: 3-phenoxy-benzyl (1R, cis) 2,2-dimethyl-3-[3-(1,1-dimethyl-propoxy)-3-oxo-1-propynyl]-cyclopropane-carboxylate A mixture of 3 g of the product of Step B of Example 83, 3 ml of methylene chloride, 1 ml of tert-amyl alcohol and 0.1 ml of 4-dimethylamino-pyridine was stirred at 5° C. while adding a mixture of 1.75 g of dicyclohexylcarbodiimide in 1 ml of methylene chloride and the mixture was returned to room temperature and was stirred for 4½ hours and was filtered. The filtrate was evaporated to dryness and the residue was chromatographed over silica gel. Elution with an 8-2 hexane-ethyl acetate mixture yielded 1.05 g of 3-phenoxy-benzyl (1R, cis, ΔZ) 2,2-dimethyl-3-[3-(1,1-dimethyl-propoxy)-3-oxo-1-propynyl]-cyclopropane-carboxylate.

STEP B: 3-phenoxy-benzyl (1R, cis, ΔZ) 2,2-dimethyl-3-[3-(1,1-dimethyl-propoxy)-3-oxo-1-propenyl]-cyclopropane-carboxylate A mixture of 1.05 g of the product of Step A, 20 ml of ethyl acetate, 0.2 g of 10% palladium hydroxide on barium sulfate and 0.2 ml of quinoline was hydrogenated and was filtered. The filtrate was washed with 0.1N hydrochloric acid then with water, was dried and evaporated to dryness under reduced pressure. The residue was chromatographed over silica gel and eluted with a 95-5-hexane-ethyl acetate mixture to obtain 0.756 g of 3-phenoxy-benzyl (1R, cis, ΔZ) 2,2-dimethyl-3-[3-(1,1-dimethyl-propoxy)-3-oxo-1-propenyl]-cycolopropane-carboxylate with a specific rotation of $[\alpha]_D^{20} = +56.5° \pm 2.5°$ (c=1% of chloroform).

EXAMPLE 90

(R,S) 1,1,1-trifluoro-2-(6-phenoxy-pyridyl)-ethyl (1R,cis,ΔZ) 2,2-dimethyl-3-(3-oxo-3-methoxy-1-propenyl)-cyclopropane-carboxylate STEP A: Ortho 6-phenoxy-picolinaldehyde 650 g of a toluene solution of 435 g of sodium di (methoxylethoxy) aluminum hydride as 70 g % and 1000 ml of toluene were admixed to obtain 1432.5 g of solution containing 432 g of the said hydride and 235 g of N-methyl-piperazine were added thereto at 0° C.

over 30 minutes. The temperature was allowed to return to 20° C. over 90 minutes to obtain 1,516 g of a reactant solution. A.1298 g of solution A were added over 45 minutes at 0° C. to a solution of 364 g of methyl 6-phenoxy-picolinate in 2,550 ml of tetrahydrofuran and after stirring at 0° C. for 30 minutes, 182 ml of water were added thereto. The temperature was allowed to rise to 20° C. over 90 minutes and the mixture was filtered. The organic filtrate was washed with water, with aqueous N hydrochloric acid and with water. The aqueous wash waters were extracted with toluene and the combined organic phases were washed with aqueous sodium bicarbonate solution, with water and were evaporated to dryness under reduced pressure to obtain 299 g of product which was crystallized from isopropyl ether to obtain 240 g of ortho 6-phenoxy-picolinaldehyde melting at 63° C. The mother liquors were evaporated to dryness and the residue was chromatographed over silica gel. Elution with a 50-30 benzene-isopropyl ether mixture yielded another 21.2 g of the product melting at 63° C.

STEP B: (R,S) 1,1,1-trifluoro-2-(6-phenoxy-pyridyl)-ethanol

A mixture of 6.76 g of the product of Step A, 7.4 g of electrolytic zinc and 10 ml of dimethylformamide was admixed at 10° C. with 20 ml of 1.7M of trifluoromethyl iodide in dimethylformamide and the mixture was subjected to ultrasonic irradiation for 15 minutes. The mixture was poured into an ice-N hydrochloric acid solution and the mixture was extracted with isopropyl ether. The organic phase was evaporated to dryness under reduced pressure and the residue was chromatographed over silica gel. Elution with an 8-2 hexane-ethyl acetate mixture yielded 5.5 g of (R,S) 1,1,1-trifluoro-2-(6-phenoxy-pyridyl)-ethanol melting at 70° C.

STEP C: (R,S) 1,1,1-trifluoro-2-(6-phenoxy-pyridyl)-ethyl (1R,cis,ΔZ) 2,2-dimethyl-3-(3-oxo-3-methoxy-1-propenyl)-cyclopropane-carboxylate 50 mg of 4-dimethylamino-pyridine and 1.3 g of dicyclohexylcarbodiimide were added at 0° C. to a mixture of 1.5 g of (R,S) 1,1,1-trifluoro-2-(6-phenoxy-pyridyl)-ethanol, 25 ml of methylene chloride and 1.3 g of (1R,cis,ΔZ), 2,2-dimethyl-3-(3-oxo-3-methoxy-1-propenyl)-cyclopropane-carboxylic acid and the temperature was allowed to rise to 20° C. The mixture was stirred at 20° C. for 18 hours and then 1 ml of ethanol and 1 ml of acetic acid were added thereto with stirring. The mixture was filtered and the filtrate was evaporated to dryness under reduced pressure. The residue was chromatographed over silica gel and was eluted with a 9-1 hexane-ethyl acetate mixture to obtain 1.8 g of (R,S) 1,1,1-trifluoro-2-(6-phenoxy-pyridyl)-ethyl (1R,cis,ΔZ) 2,2-dimethyl-3-(3-oxo-3-methoxy-1-propenyl)-cyclopropane-carboxylate with a specific rotation of $[\alpha]_D^{20} = +84.5° \pm 3°$ (c=0.5% in chloroform).

EXAMPLE 91

Using the procedure of Example 90, there was obtained (R,S) 1,1,1-trifluoro-2-(6-phenoxy-pyridyl)-ethyl (1R,cis,ΔZ) 2,2-dimethyl-3-(3-oxo-3-tert.-butoxy-1-propenyl)-cyclopropanecarboxylate with a specific rotation of $[\alpha]_D^{20} = +94° \pm 3°$ (c=0.5% in chloroform).

EXAMPLE 92

Using the procedure of Example 90, there was obtained (R) m-phenoxy-phenethyl (1R,cis,ΔZ) 2,2-dimethyl-3-(3-oxo-3-cyclopropyloxy-1-propenyl)-cyclopropane-carboxylate with a specific rotation of $[\alpha]_D^{20} = +133.5°$ (c=0.7% in benzene).

EXAMPLE 93

Using the procedure of Example 90, there was obtained (R,S)α-trifluoromethyl-3-phenoxy-benzyl (1R,cis,ΔZ) 2,2-dimethyl-3-(3-oxo-3-methoxy-1-propenyl)-cyclopropane-carboxylate with a specific rotation of $[\alpha]_D^{20} = +64.5° \pm 3°$ (c=0.5% in chloroform).

EXAMPLE 94

Using the procedure of Example 90, there was obtained (R,S)α-(trifluoromethyl)-m-phenoxy-benzyl(1R,cis,ΔZ) 2,2-dimethyl-3-[3-oxo-3-tert.-butoxy-1-propenyl]-cyclopropane-carboxylate with a specific rotation of $[\alpha]_D^{20} = +68°$ (c=0.25% in chloroform).

EXAMPLE 95

Using the procedure of Example 90, there was obtained (R,S)α-trifluoromethyl-3-phenoxy-4-fluoro-benzyl (1R,cis,ΔZ) 2,2-dimethyl-3-[3-oxo-3-methoxy-1-propenyl]-cyclopropane-carboxylate with a specific rotation of $[\alpha]_D^{20} = 60° \pm 2.5°$ (c=0.5% in chloroform).

EXAMPLE 96

Using the procedure of Example 90, there was obtained (R,S)α-trifluoromethyl-3-phenoxy-4-fluoro-benzyl (1R,cis,ΔZ) 2,2-dimethyl-3-[3-oxo-3-tert.-butoxy-1-propenyl]-cyclopropane-carboxylate with a specific rotation of $[\alpha]_D^{20} = +66° \pm 4°$ (c=0.25% in chloroform).

EXAMPLE 97

Using the procedure of Example 90, there was obtained (R,S)α-cyano-2-(6-phenoxy-pyridyl)-methyl (1R,cis,ΔZ) 2,2-dimethyl-3-[3-oxo-3-cyclopropyloxy-1-propenyl]-cyclopropane-carboxylate with a specific rotation of $[\alpha]_D^{20} = +26.5°$ (c=0.6% in benzene).

EXAMPLE 98

Using the procedure of Example 90, there was obtained 3-phenoxy-benzyl (1R,cis,ΔZ) 2,2-dimethyl-3-[3-oxo-3-cyclobutyloxy-1-propenyl]-cyclopropane-carboxylate with a specific rotation of $[\alpha]_D^{20} = +46.5° \pm 1.5°$ (c=1.4% in chloroform).

EXAMPLE 99

Using the procedure of Example 90, there was obtained 3-phenoxy-benzyl (1R,cis,ΔZ) 2,2-dimethyl-3-[3-oxo-3-cyclopropyloxy-1-propenyl]-cyclopropane-carboxylate with a specific rotation of $[\alpha]_D^{20} = +41° \pm 1°$ (c=1.5% in chloroform).

EXAMPLE 100

Using the procedure of Example 90, there was obtained (1R) (3-phenoxyphenyl)-propyne (1R,cis,ΔZ) 2,2-dimethyl-3-[3-oxo-3-cyclopropyloxy-1-propenyl]-cyclopropane-carboxylate with a specific rotation of $[\alpha]_D^{20} = +46.5° \pm 2.5°$ (c=0.5% in chloroform).

EXAMPLE 101

Using the procedure of Example 90, there was obtained (R,S)α-cyano-3-benzyloxybenzyl (1R,cis,ΔZ) 2,2-dimethyl-3-[3-oxo-methoxy-1-propenyl]-cyclopropane-carboxylate with a specific rotation of $[\alpha]_D^\circ = +43.5°$ (c=0.8% in methylene chloride).

EXAMPLE 102

Using the procedure of Example 90, there was obtained (R,S)α-cyano-2-phenoxy-2-propenyl (1R,cis,ΔZ) 2,2-dimethyl-3-[3-oxo-3-methoxy-1-propenyl]-cyclopropane-carboxylate with a specific rotation of $[\alpha]_D^{20} = +61°\pm 2.5°$ (c=0.55% in chloroform).

EXAMPLE 103

Using the procedure of Example 90, there was obtained 4-indolyl-methyl (1R,cis,ΔZ) 2,2-dimethyl-3-[3-oxo-3-methoxy-1-propenyl]-cyclopropane-carboxylate.

NMR Spectrum (deuterochloroform): Peaks at 1.25–1.32 ppm (hydrogens of geminal methyls); at 3.7 ppm (hydrogens of CH₃O—); at 5.44 ppm (hydrogen of —COO—CH₂—); at 5.8–6.0 ppm (hydrogen on carbon α- to —COOCH₃); at 8.4 ppm (hydrogen of —NH—).

EXAMPLE 104

Using the procedure of Example 90, there was obtained (R,S) cyano-(4-indolyl)-methyl (1R,cis,ΔZ) 2,2-dimethyl-3-[3-oxo-3-methoxy-1-propenyl]-cyclopropane-carboxylate.

NMR Spectrum (deuterochloroform): Peaks at 1.23–1.25–1.32–1.37 ppm (hydrogens of geminal methyls); at 1.92–1.95 ppm (1-hydrogen of cyclopropyl); at 3.15–3.53 ppm (3-hydrogen of cyclopropyl); at 3.7–3.8 ppm (hydrogens of CH₃O—); at 5.9–6.1 ppm and 5.9–6.1 ppm (hydrogen on carbon α- to —COOCH₃); at 6.7 ppm (hydrogen

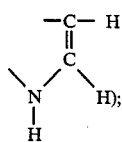

at 6.8 ppm (hydrogen on carbon α- to —CN); at 7.2–7.7 ppm (hydrogen of

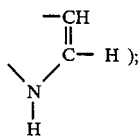

at 7.2–7.77 ppm (hydrogens of benzene ring); at 8.3 ppm (hydrogen of —NH—)

EXAMPLE 105

Using the procedure of Example 90, there was obtained (R,S) 4-chromanol (1R,cis,ΔZ) 2,2-dimethyl-3-[3-oxo-3-methoxy-1-propenyl]-cyclopropane-carboxylate with a specific rotation of $[\alpha]_D^{20} = +52°$ (c=0.3% in chloroform).

EXAMPLE 106

Using the procedure of Example 90 there was obtained 2-phenoxy-2-propenyl (1R,cis,ΔZ) 2,2-dimethyl-3-[3-oxo-3-methoxy-1-propenyl]-cyclopropane-carboxylate with a specific rotation of $[\alpha]_D^{20} = +50°$ (c=0.18% in chloroform) and having a melting point of <50° C.

EXAMPLE 107

Using the procedure of Example 90, there was obtained (R,S)α-cyano-2-phenoxy-2-propenyl (1R,cis,ΔZ) 2,2-dimethyl-3-[3-oxo-3-tert-butoxy-1-propenyl]-cyclopropane-carboxylate with a specific rotation of $[\alpha]_D^{20} = +72.5°\pm 2.5°$ (c=0.5% in chloroform).

EXAMPLE 108

Using the procedure of Example 90, there was obtained (R,S)1-(5-phenyl-isoxazol-3-yl)-ethyl (1R,cis,ΔZ) 2,2-dimethyl-3-[3-oxo-3-methoxy-1-propenyl]-cyclopropane-carboxylate.

NMR Spectrum (deuterochloroform): Peaks at 1.29–1.33 ppm (hydrogens of geminal methyls); at 1.58–1.69 ppm and 1.60–1.70 ppm (hydrogens of methyl of

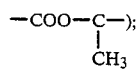

at 1.95–2.09 ppm (1-hydrogen of cyclopropyl); at 3.1–3.44 ppm (3-hydrogen of cyclpropane); at 3.70–3.72 ppm (hydrogens of CH₃O—); at 5.8–5.9 ppm (hydrogen of

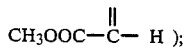

at 5.9–6.0–6.1–6.2 ppm (hydrogen of

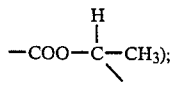

at 6.4–6.8 ppm (hydrogen of

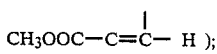

at 6.4–6.5 ppm (hydrogen of

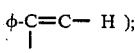

at 7.3–7.8 ppm (hydrogens of benzene ring).

EXAMPLE 109

(1R) (3-phenoxy-phenyl)-ethyl (1R,cis,ΔZ) 2,2-dimethyl-3-(3-oxo-3-tertamyloxy-1-propenyl)-cyclopropane-carboxylate A mixture of 4 g of (1R) (3-phenoxy-phenyl)-ethyl (1R,cis,ΔZ) 2,2-dimethyl-3-(3-oxo-3-hydroxy-1-propenyl)-cyclopropane-carboxylate, 8 ml of methylene chloride and 8 ml of thionyl chloride was stirred at 20° C. for one hour and was then evaporated to dryness under reduced pressure. The residue was added to 20 ml of methylene chloride and 3.7 g of tert.-amyl alcohol were added dropwise to the mixture at 5° C. The mixture was stirred at 20° C. for 17 hours and was evaporated to dryness under reduced pressure. The residue was chromatographed over silica gel and was eluted with an 8-2 hexane-isopropyl ether mixture to obtain 0.8 g of (1R) (3-phenoxy-phenyl)-ethyl (1R,cis, ΔZ) 2,2-dimethyl-3-(3-oxo-3-tertamyloxy-1-propenyl)-cyclopropane-carboxylate with a specific rotation of $[\alpha]_D^{20} = +123°$ (c=0.8% in chloroform).

EXAMPLE 110

Using the procedure of Example 109 there was obtained (1R) (3-phenoxyphenyl)-ethyl (1R,cis,ΔZ) 2,2-dimethyl-3-[3-oxo-3-(1-methylcyclobutoxy)-1-propenyl]-cyclopropane-carboxylate with a specific rotation of $[\alpha]_D^{20} = +125.5°\pm2°$ (c=0.65% in chloroform).

EXAMPLE 111

(S)α-cyano-3-phenoxy-4-fluoro-benzyl (1R,cis,ΔZ) 2,2-dimethyl-3-(3-oxo-3-propoxy-1-propenyl)-cyclopropane-carboxylate 1.6 ml of n-propanol were added at 20° C. to a solution of 2.31 g of (S) α-cyano-3-phenoxy-4-fluorobenzyl (1R,cisΔZ) 2,2-dimethyl-3-(3-oxo-3-chloro-1-propenyl)-cyclopropane-1-carboxylate in 10 ml of methylene chloride and the mixture was stirred at 20° C. for 90 minutes and was then poured into a monosodium phosphate solution. The mixture was extracted with methylene chloride and the organic phase was washed with water and evaporated to dryness under reduced pressure. The residue was chromatographed over silica gel and was eluted with a 9-1 cyclohexane-ethyl acetate mixture to obain 1.31 g of (S) α-cyano-3-phenoxy-4-fluoro-benzyl (1R,cis,ΔZ) 2,2-dimethyl-3-(3-oxo-3-propoxy-1-propenyl)-cyclopropane-carboxylate melting at 60° C. and having a specific rotation of $[\alpha]_D^{20} = +51.5°\pm1.5°$ (c=1.5% in chloroform).

EXAMPLE 112

Using the procedure of Example 111, there was obtained (S)α-cyano-3-phenoxy-4-fluoro-benzyl (1R,cis,ΔZ) 2,2-dimethyl-3-[3-oxo-3-(R,S-2-butoxy)-1-propenyl]-cyclopropane-carboxylate with a specific rotation of $[\alpha]_D^{20} = +53°\pm1.5°$ (c=1% in chloroform) and melting at 74° C.

EXAMPLE 113

(S)α-cyano-3-phenoxy-4-fluoro-benzyl (1R,cis,ΔZ) 2,2-dimethyl-3-(3-oxo-3-tert.-amyloxy-1-propenyl)-cyclopropane-carboxylate 61 g of calcium carbonate and then 62 ml of tert.-amyl alcohol were added to a solution of 41.8 g of (S)α-cyano-3-phenoxy-4-fluoro-benzyl (1R,cis,ΔZ) 2,2-dimethyl-3-(3-oxo-3-chloro-1-propenyl)-cyclopropane-carboxylate in 300 ml of methylene chloride and the mixture was stirred at 20° C. for 16 hours and was filtered. The filtrate was washed with aqueous monsodium phosphate solution, with water and was evaporated to dryness under reduced pressure. The residue was chromatographed over silica gel and was eluted with methylene chloride. The product was empasted with n-hexane and dried to obtain 29 l g of (S)α-cyano-3-phenoxy-4-fluorobenzyl (1, R, cis, ΔZ) 2,2-dimethyl-3-(3-oxo-3-tert.-amyloxy-1-propenyl)-cyclopropane-carboxylate melting at 83° C. and having a specific rotation of $[\alpha]_D^{20} = +58°\pm2.5°$ (c=0.8% in toluene).

EXAMPLE 114

3-phenoxy-benzyl (1R, cis, ΔZ) 2,2-dimethyl-3-[3-oxo-3-(1-methyl-cyclobutoxy)-1-propenyl]-cyclopropane-carboxylate A mixture of 0.25 g of 10% palladium hydroxide on barium sulfate and 3 ml of ethyl acetate were added to a balloon flask attached to a hydrogenation apparatus and the flask was purged. The catalyst was hydrogenated at 20° C. under normal pressure and the flask was purged. A mixture of 0.25 ml of quindine, 1.33 g of 3-phenoxy-benzyl (1R, cis, ΔZ) 2,2-dimethyl-3-[3-oxo-3-(1-methyl-cyclobutoxy)-1-propynyl]-cyclopropane-carboxylate and 22 ml of ethyl acetate was added to the flask which was purged. Hydrogenation was effected at 20° C. under atmospheric pressure until 65 ml of hydrogen was absorbed (68.3 ml was theoretical) and the flask was purged. The mixture was filtered and the filtrate was washed with aqueous 0.1N hydrochloric acid, water and evaporated to dryness under reduced pressure. The residue was chromatographed over silica gel and was eluted with a 9-1 cyclohexane-ethyl acetate mixture to obtain 1.04 g of 3-phenoxy-benzyl (1R, cis, ΔZ) 2,2-dimethyl-3-[3-oxo-3-(1-methyl-cyclobutoxy)-1-propenyl]-cyclopropane-carboxylate with a specific rotation of $[\alpha]_D^{20} = +45.5°\pm2°$ (c=0.75% in chloroform).

EXAMPLE 115

Using the procedure of Example 114 there was obtained 4-cyano-benzyl (1R, cis, ΔZ) 2,2-dimethyl-3-[3-oxo-3-methoxy-1-propenyl]-cyclopropane-carboxylate with a specific rotation of $[\alpha]_D^{20} = +69°$ (c=0.5% in chloroform).

EXAMPLE 116

Using the procedure of Example 114 there was obtained benzyl (1R, cis, ΔZ) 2,2-dimethyl-3-[3-oxo-3-ethoxy-1-propenyl]-cyclopropane-carboxylate with a specific rotation of $[\alpha]_D^{20} = +50.5°$ (c=0.6% in chloroform).

PREPARATION A (S)α-cyano-3-phenoxy-4-fluoro-benzyl (1R, cis, ΔZ) 2,2-dimethyl-3-(3-oxo-3-hydroxy-1-propenyl)-cyclopropane-carboxylate A mixture of 16.4 g of (S)α-cyano-3-phenoxy-4-fluorobenzyl (1R, cis, ΔZ) 2,2-dimethyl-3-(3-oxo-3-tert.-butoxy-1-propenyl)-cyclopropane-carboxylate, 1.6 g of p-toluene sulfonic acid monohydrate and 160 ml of toluene was rapidly heated to reflux at 120° C. and held there until isobutylene gas formation ceased. The mixture was cooled to 0° C. and was filtered and the filtrate was evaporated to dryness under reduced pressure. The residue was chromatographed over silica gel and was eluted with a 70-30-1 n-hexane-ethyl acetate-acetic acid mixture to obtain 13.3 g of (S)α-cyano-3-phenoxy-4-fluoro-benzyl (1R, cis, ΔZ) 2,2-dimethyl-3-(3-oxo-3-hydroxy-1-propenyl)-cyclopropane-carboxylate melting at 99° C. and having a specific rotation of $[\alpha]_D^{20} = +52.5°$ (c=0.5% in chloroform).

PREPARATION B (R, S) 1-(m-phenoxy-phenyl)-2,2,2-trifluoro-ethanol

STEP A: 1-(m-phenoxy-phenyl)-2,2,2-trifluoro-ethanone

A few drops of m-phenoxy-bromobenzene were added to a mixture of 16.6 g of magnesium (50% turnings) in 53 ml of tetrahydrofuran and the mixture was heated to 40°–45° C. Crystallization began and the rest of 62.2 g of m-phenoxy-bromobenzene was added dropwise at reflux over 45 minutes. 183 ml of tetrahydrofuran were added and the mixture was refluxed for one hour and was cooled to 0° C. to obtain a solution of a magnesium compound. The said solution was then added at 0° C. over 40 minutes to a mixture of 40.8 g of sodium trifluoroacetate in 240 ml of tetrahydrofuran and the mixture was stirred for two hours and was poured into aqueous 0.1N hydrochloric acid solution. The mixture was extracted with ether and the ether phase was washed with water, with aqueous N sodium hydroxide and with water. The ether phase was added to two liters of methylene chloride and the mixture was evaporated to dryness under reduced pressure to obtain 56.2 g of raw 1-(m-phenoxy-phenyl)-2,2,2-trifluoro-ethanone which was used as is for the next step.

STEP B: (R, S) 2,2,2-trifluoro-1-(m-phenoxy-phenyl)-ethanol 2.71 g of sodium borohydride were added in small fractions over 35 minutes at 0° C. to a solution of 56.1 g of the raw product of Step A in 235 ml of methanol and the mixture was stirred for 25 minutes while allowing the temperature to rise to room temperature. The mixture was added to aqueous 1N hydrochloric acid solution and water was added with stirring. The decanted aqueous phase was extracted with methylene chloride and the organic phase was washed with water and evaporated to dryness under reduced pressure. The residue was chromatographed over silica gel and was eluted with methylene chloride to obtain 13.3 g of (R, S) 2,2,2-trifluoro-1-(m-phenoxy-phenyl)-ethanol.

PREPARATION C 1-(4-fluoro-3-phenoxy-phenyl)-2,2,2-trifluoro-ethanol

A mixture of 2 g of 4-fluoro-3-phenoxy-benzaldehyde, 5 ml of dimethylforomamide, 2 g of electrolytic zinc and 15 ml of a solution of 13.5 mmols of trifluoromethyl iodide in dimethylformamide was ultrasonically irradiated for 15 minutes and the mixture was poured into aqueous N hydrochloric acid. The mixture was extracted with isopropyl ether and the organic phase was evaporated to dryness under reduced pressure. The residue was chromatographed over silica gel and was eluted with a 1-1 methylene chloride-hexane mixture to be obtain 1.5 g of 1-(4-fluoro-3-phenoxy-phenyl)-2,2,2-trifluoroethanol.

NMR Spectrum (deuterochloroform): Peaks at 4.03–4.12 ppm (hydrogen of —OH); at 7.4 ppm (hydrogen of

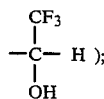

at 10.3–11.1 ppm (hydrogens of aromatic ring).

PREPARATION D (S)α-cyano-3-phenoxy-4-fluoro-benzyl (1R, cis, ΔZ) 2,2-dimethyl-3-(3-oxo-3-chloro-1propenyl)-cyclopropane-carboxylate 10 ml of thionyl chloride were added at 20° C. to a mixture of 4.5 g of (S)α-cyano-3-phenoxy-4-fluoro-benzyl (1R, cis, ΔZ) 2,2-dimethyl-3-(3-oxo-3-hydroxy-1-propenyl)-cyclopropane-carboxylate in 20 ml of methylene chloride and the mixture was stirred for 105 minutes and was evaporated to dryness under reduced pressure to obtain 4.7 g of (S)α-cyano-3-phenoxy-4-fluoro-benzyl (1R, cis, ΔZ) 2,2-dimethyl-3-(3-oxo-3-chloro-1-propenyl)-cyclopropane-carboxylate.

PREPARATION E (R, S)α-cyano-3-benzyloxy-benzyl alcohol 2.7 g of sodium cyanide were added at 0° C. to a mixture of 5.85 g of 3-benzyloxy-benzaldehyde, 20 ml of distilled water and 70 ml of methanol and the mixture was stirred at 20° C. for 3 hours and was filtered. The methanol was distilled from the filtrate under reduced pressure and distilled water was added thereto. The mixture was extracted with ether and the organic phase was washed with water and evaporated to dryness under reduced pressure to obtain 6 g of (R, S)α-cyano-3-benzyloxy-benzyl alcohol.

PREPARATION F 3-(1R, S-hydroxyethyl)-5-phenyl-isoxazole 382 mg of sodium borohydride were added at 0° C. to a mixture of 3.78 g of 3-acetyl-5-phenyl-isoxazole [prepared by Synthesis, (1980), p. 877] in 50 ml of methanol and the mixture was stirred at 0° C. for 30 minutes and was poured into a mixture of ice and water. The mixture was extracted with methylene chloride and the organic phase was evaporated to dryness under reduced pressure to obtain 3.24 g of 3-(1R, S-hydroxyethyl)-5-phenyl-isoxazole melting at <50° C.

PREPARATION G (R, S)α-cyano-(4-indolyl)-methanol 6.5 ml of acetic acid were added dropwise at 0° C. to a mixture of 7.15 g of indole-4-carboxaldehyde [J. Org. Chem., Vol. 45, No. 16 (1980), p. 3351] in 30 ml of methanol and 39 ml of water and 4.9 g of sodium cyanide were added thereto. The mixture was stirred at 20° C. for 4 hours and the methanol was distilled under reduced pressure. The mixture was extracted with ether and the organic phase was washed with water and evaporated to dryness under reduced pressure to obtain 8 g of (R, S)α-cyano-(4-indolyl)-methanol.

PREPARATION H 2-phenoxy-1R, S-cyano-2-propen-1-ol

STEP A: 2-pheoxy-2-propenol

A mixture of 7.75 g of a complex of pyridine and chromic oxide, 2.25 g of 2-phenoxy-2-propenol [prepared by Kushch et al, Vusokomol Soedin Ser. B, Vol. 21 (1979), p. 708–13] and 20 ml of methylene chloride was stirred at 20° C. for 16 hours and was filtered. The filtrate was evaporated to dryness under reduced pressure and the residue was chromatographed over silica gel. Elution with an 8-2 hexane-ethyl acetate mixture yielded 1.1 g of 2-phenoxy-2-propenol.

NMR Spectrum (deuterochloroform): Peaks at 5.26–5.3 ppm and 5.37–5.4 ppm (hydrogens of methylene); at 7.0–7.5 ppm (hydrogens of aromatic ring); at 9.5 ppm (hydrogen of

STEP B: 2-phenoxy-1RS-cyano-2-propen-1-ol 700 mg of sodium cyanide were added at 0° C. to a mixture of 1 g of the product of Step A, 10 ml of water, 5 ml of methanol and 1 ml of acetic acid and the mixture was stirred at 0° C. for 25 minutes and the temperature rose to 20° C. The mixture was stirred at 20° C. for one hour and was extracted with ether. The organic phase was evaporated to dryness under reduced pressure and the residue was added to toluene. The mixture was evaporated to dryness under reduced pressure to obtain 900 mg of 2-phenoxy-1RS-cyano-2-propen-1-ol.

IR Spectrum (chloroform): Absorption at 3580 cm$^{-1}$ and 3560 cm$^{-1}$ (associated OH); at 1660 cm$^{-1}$ (asymetric C=C); at 1595-1495 cm$^{-1}$ (aromatic ring); at 860 cm$^{-1}$ (=CH$_2$).

EXAMPLE A

A soluble concentrate was prepared by homogenously mixing 0.25 g of the product of Example 1 or of Example 91. 1 g of piperonyl butoxide, 0.25 g of Tween 80, 0.1 g of Topanol A and 98.4 g of water.

EXAMPLE B

An emulsifiable concentrate was prepared by intimately mixing 0.015 g of the product of Example 1 or of Example 100, 0.5 of piperonyl butoxide, 0.1 g of Topanol A, 3.5 g of Tween 80 and 95.885 g of xylene.

EXAMPLE C

An emulsifiable concentrate was prepared by homogenously mixing 1.5 g of the product of Example 1 or of Example 96, 20 g of Tween 80, 0.1 g of Topanol A and 78.4 g of xylene.

EXAMPLE D

A fumigant composition was prepared by homogenously mixing 0.25 g of the product of Example 1 or of Example 90, 25 g of tabu powder, 40 g of cedar needle powder, 33.75 g of pine-wood powder, 0.5 g of brilliant green and 0.5 g of p-nitrophenol.

PARASITIC STUDY

A. Lethal effect on houseflies

The test insects were female houseflies sensitive to pyrethrinoids elevated at 22°-23° C. and 60 to 65% relative humidity and 4 to 5 days old. One μl of an acetone solution of the test compound was topically applied to the dorsal thorax of the insects with an Arnold micro-manipulator using 50 insects for each dose. The number of dead was determined 24 hours later and the compounds of Examples 1 to 8 showed a very good lethal activity in this test. The compounds of Examples 100, 111 and 112 had a DL$_{50}$ in ng per insect of 3.68, 0.85 and 3.98, respectively.

B. Lethal effect on larvae of *Spodoptera littoralis*

The test was effected by a topical application of an acetone solution of the test compound with an Arnold micro-manipulator to the dorsal thorax of larvae of *Spodoptera littoralis* in the 4th larvae stage using 15 insects per dose. The larvae were 10 days old having been kept at 24° C. and a 65% relative humidity and the larvae, after treatment, were placed in an artifical nutritive medium (Poitout media) and the number of dead was determined after 48 hours. The compounds of Examples 1 to 8 showed a good lethal activity in this test and the compounds of Examples 92, 97 and 99 had a DL$_{50}$ in ng per insect of 18.96 12.9 and 11.67, respectively.

C. Activity against larvae of *Epilachna varivestris*

The test was similar to test B applying topically an acetone solution of the test compound using larvae of *Epilachna varivestris* in the last stage of development and after treatment, the larvae were placed on bean plants. The number of dead was determined after 72 hours and the compounds of Examples 1 to 8 showed a good lethal activity.

D. Knockdown power against houseflies 50 female houseflies 4 to 5 days old per dose were subjected to a direct spray in a Kearns and March cylinder using as the solvent a mixture of 5% acetone and Isopar L (petroleum solvent) at a dose of 2 ml in one second. Readings were taken every minute for 10 minutes and then at 15 minutes to determine the KT$_{50}$ by the usual method. The products of Examples 1 to 8 have a good activity and the results are reported in Table I.

TABLE I

| Compound of Example | Dose in g/l | KT$_{50}$ in minutes |
|---|---|---|
| 1 | 1 | 0.4 |
|   | 0.5 | 1.26 |
|   | 0.25 | 2.02 |
| 90 | 0.25 | 2.78 |
| 92 | 0.25 | 4.72 |
| 97 | 0.25 | 1.71 |
| 99 | 0.25 | 3.00 |
| 100 | 0.25 | 4.97 |
| 101 | 0.25 | 4.02 |
| 105 | 0.25 | 3.61 |
| 111 | 0.25 | 4.98 |
| 112 | 0.25 | 2.83 |

E. Activity against *Tetranychus urticae*

Bean plants having 2 leaves were treated by a Fisher pistol with different doses of the test compound and after drying, the plants were infested with 25 female *Tetranychus urticae* per leaf and were held at 22°-23° C. and a relative humidity of 65%. The number of living and dead acariens was determined after 24 and 48 hours and the products of Examples 1 to 8 showed a good adulticidal activity. The compound of Examples 98, 110, 111 and 112 had a CL$_{50}$ in mg/hl of 2,087, 1,204, 1,342 and 1,718, respectively.

F. Insecticidal activity against *Culex pipiens*

Neutral fumigant serpentine supports were impregnated with an acetone solution of the test compound and 20 female mosquitoes 4 to 5 days old were placed in a closed cylinder with a volume of 13.50 dm$^3$. Over 2 minutes, the fumigant serpentine coil was consumed at one end and the number of insects knocked down was determined every minutes for 5 minutes and then the number of dead insects was determined after 5 minutes. The results for the compounds of Example 1 was at a dose of 0.60% of active material by weight of the coil was a KT$_{50}$ of 5.42 mn and thelethal effect was 98.3%.

G. Lethal effect against beetles

The test was effected by contact with a film after depositing with a pipette acetone solutions of different concentrations on the bottom of a glass Petri bottle. The edges were coated with talc to prevent the escape of the insects and the 50% lethal concentration was determined. The compounds of Examples 97, 100, 111 and 112 had a CL$_{50}$ in mg/m$^2$ of 0.22, 0.09, 0.11 and 0.14 respectively.

H. Lethal effect on *Acanthocelides obtectus*

Using the test procedure of B, one μl of an acetone solution of the test compound was topically applied to the thorax of the insect to determine the DL$_{50}$ in ng per insect. The results with the compounds of Examples 100 and 111 were 17.33 and 15.13, respectively.

I. Lethal effect on *Aphis cracivora*

10 adult *Aphis cracivora* more than 7 days old were used for each test concentration in a contact-ingestion method. A bean leaf placed on a damp paper circle on the bottom of a plastic Petri dish was sprayed with a Fischer pistol with 2 ml of an acetone solution of test product with one ml of each side and the leaf was dried. The insects were placed in the dish in contact with the leaf for one hour and the percent of dead insects after 24 hours was compared with untreated leaves. The DL$_{50}$ in ng per insect was 0.80 for the compounds of Examples 91 and 96.

From the above testes, it can be concluded that the compounds of the application have a good insecticidal and acaricidal activity.

Various modifications of the compounds and methods of the invention may be made without departing from the spirit or scope thereof and it is to be understood that the invention is intended to be limited only as defined in the appended claims.

What we claim is:

1. A compound selected from the group consisting of a (1R, cis) compound of the formula

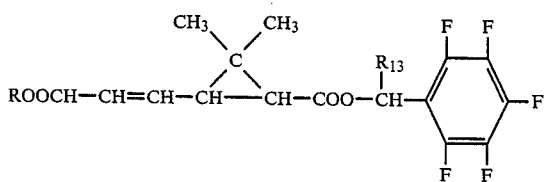

wherein R$_{13}$ is selected from the group consisting of hydrogen and cyano and R is selected from the group consisting of alkyl of 1 to 18 carbon atoms, alkenyl and alkynyl of 2 to 18 carbon atoms, cycloalkyl of 3 to 6 carbon atoms optionally substituted with at least one lower alkyl and alkyl of 1 to 8 carbon atoms substituted with cycloalkyl of 3 to 6 carbon atoms and the geometry of the double bond is Z.

2. A compound of claim 1 wherein R is methyl and R$_{13}$ is hydrogen.

3. A compound of claim 1 wherein R is methyl and R$_{13}$ is cyano.

4. A compound of claim 1 wherein R is tert.-butyl and R$_{13}$ is hydrogen.

5. A compound of claim 1 wherein R is methyl.

6. A compound of claim 1 wherein R is selected from the group consisting of ethyl, n-propyl, isopropyl, tert.-butyl and cyclopropylmethyl.

7. A method of combatting insects, comprising contacting the insects with an insecticidally effective amount of at least one compound of claim 1.

8. A method of claim 7 wherein R is selected from the group consisting of methyl, ethyl, n-propyl, isopropyl, tert.-butyl and cyclopropylmethyl.

9. An insecticidal composition comprising an insecticidally effective amount of at least one compound of claim 1 and an inert carrier.

10. A composition of claim 9 wherein R is selected from the group consisting of methyl, ethyl, n-propyl, isopropyl, tert.-butyl and cyclopropylmethyl.

11. A composition of claim 1 comprising at least one second active ingredient which is a pyrethrinoid ester selected from the group consisting of esters of allethrolone, of 3,4,5,6-tetrahydrophthalimidomethyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols and 2,2-dimethyl-3-(2,2-dichlorovinyl)-cyclopropane-1-carboxylic acids, esters of α-cyano-3-phenoxy-benzyl alcohols and 2,2-dimethyl-3-(2,2-dibromovinyl)-cyclopropane-1-carboxylic acids, esters of 3-phenoxy-benzyl alcohol and 2-p-chlorophenyl-2-isopropyl-acetic acids, esters of allethrolones, 3,4,5,6-tetrahydrophthalimido-methyl alcohol, 5-benzyl-3-furyl-methyl alcohol, 3-phenoxybenzyl alcohol or α-cyano-3-phenoxy-benzyl alcohols and 2,2-dimethyl-3-(1,2,2,2-tetrahaloethyl)-cyclopropane-1-carboxylic acids where halo is fluorine, chlorine and bromine wherein the compounds of formula I are in all possible stereoisomer forms of the acids and alcohols of the pyrethrinoid esters.

* * * * *